(12) United States Patent
Pinna et al.

(10) Patent No.: US 11,266,663 B2
(45) Date of Patent: Mar. 8, 2022

(54) TREATMENT OF NEUROPSYCHIATRIC DISORDERS WITH NEUROSTEROIDS AND ANALOGUES THEREOF

(71) Applicants: THE BOARD OF TRUSTEES OF THE UNIVERSITY OF ILLINOIS, Urbana, IL (US); Ayikoe-Guy Mensah-Nyagan, Strasbourg (FR)

(72) Inventors: Graziano Pinna, Chicago, IL (US); Andrea Locci, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 58 days.

(21) Appl. No.: 16/626,017

(22) PCT Filed: Jun. 22, 2018

(86) PCT No.: PCT/US2018/039027
§ 371 (c)(1),
(2) Date: Dec. 23, 2019

(87) PCT Pub. No.: WO2018/237282
PCT Pub. Date: Dec. 27, 2018

(65) Prior Publication Data
US 2020/0121694 A1 Apr. 23, 2020

Related U.S. Application Data

(60) Provisional application No. 62/523,917, filed on Jun. 23, 2017.

(51) Int. Cl.
| | | |
|---|---|---|
| *A61K 31/405* | (2006.01) | |
| *A61K 31/573* | (2006.01) | |
| *A61P 25/22* | (2006.01) | |
| *A61P 25/24* | (2006.01) | |
| *A61K 31/58* | (2006.01) | |

(52) U.S. Cl.
CPC ............ *A61K 31/573* (2013.01); *A61K 31/58* (2013.01); *A61P 25/22* (2018.01); *A61P 25/24* (2018.01)

(58) Field of Classification Search
CPC .................................................... A61K 31/573
USPC ............................................................ 514/172
See application file for complete search history.

(56) References Cited

U.S. PATENT DOCUMENTS

| | | | |
|---|---|---|---|
| 2009/0203658 A1* | 8/2009 | Marx ................... | A61P 25/00 514/171 |
| 2014/0058079 A1* | 2/2014 | Mensah-Nyagan ..... | A61P 25/04 540/100 |

OTHER PUBLICATIONS

Amin, Pharmacology, Biochemistry and Behavior 84 (2006) 635-643.*
Vallee Journal of Steroid Biochemistry & Molecular Biology 160 (2016) 78-87.*
Pinna, Frontier in Cellular Neuroscience, vol. 8, Sep. 11, 2014.*
Brown, Neuropsychopharmacology, vol. 39, No. 12,Jun. 11, 2014, pp. 2867-2873.*
Balboa, Psychopharmacology, vol. 231, No. 17, Apr. 30, 2014, pp. 3569-3580.*

* cited by examiner

*Primary Examiner* — Nizal S Chandrakumar
(74) *Attorney, Agent, or Firm* — Thomas | Horstemeyer, LLP

(57) ABSTRACT

Described herein are neurosteroids and analogues thereof and derivatives thereof, including, but not limited to, allopregnanolone, allopregnanolone analogues, and derivatives thereof that can be used for treatment of a neuropsychiatric disorder and/or symptom thereof. Also described herein are pharmaceutical formulations containing an effective amount of a neurosteroids and analogues thereof and derivatives thereof, where the effective amount can be effective for treating a neuropsychiatric disorder and/or symptom thereof. Also described herein are methods of treating a neuropsychiatric disorder and/or a symptom thereof in a subject in need thereof.

15 Claims, 20 Drawing Sheets

Early SI mice

- GABA
 Steroidogenic Acute Regulatory Protein
- Glutamate
 Peroxisome Proliferator-Activated Receptor
 Allopregnanolone
 Retinoid X Receptor
 Pregnanolone
 Translocator Protein
 Pregnenolone
 Synaptic GABA Receptor
 Allopregnanolone Sulfate
 Extrasynaptic GABA Receptor
 Pregnanolone Sulfate
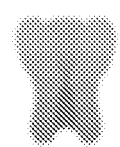 NMDA Receptor
 Palmitoylethanolamide
FIG. 11 (ctnd.)

TREATMENT OF NEUROPSYCHIATRIC DISORDERS WITH NEUROSTEROIDS AND ANALOGUES THEREOF

CROSS-REFERENCE TO RELATED APPLICATIONS

This application claims the benefit of and priority to U.S. Provisional Patent Application No. 62/523,917, filed on Jun. 23, 2017, entitled "Therapeutic molecules with applications for anxiety, depression, and aggression," the contents of which is incorporated by reference herein in its entirety.

BACKGROUND

Neuropsychiatric disorders are generally diseases, conditions, and disorders of affect, cognition, and/or behavior that can arise from an overt disorder in cerebral function or from indirect effects of extracerebral diseases and disorders. Neuropsychiatric disorders are a significant burden on society and can impair the health of those affected, as well as their ability to learn and work. They also can burden those not afflicted in that those affected often must rely on caregivers or other forms of assistance due to their inability to fully engage and function in normal work and life activities. As such, there exists a need for the development of improved treatments for neuropsychiatric disorders.

SUMMARY

Described in some aspects herein are methods of treating a neuropsychiatric disorder or a symptom thereof in a subject in need thereof that can include the step of administering an effective amount of a neurosteroid or an analogue thereof or a derivative of a neruosteroid or a derivative of a neurosteroid analogue to the subject in need thereof. The neurosteroid or analogue thereof or a derivative of a neruosteroid or an analogue thereof can be allopregnanolone or an analogue thereof or a derivative of allopregnanolone or a derivative of an allopregnanolone analogue. The neuruosteroid or the analogue thereof or the derivative of the neruosteroid or the derivative of a neurosteroid analogue has a formula according to Formula (I)

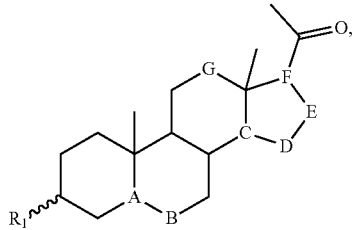

Formula (I)

wherein $R_1$ is selected from the group of: 3-alpha or 3-beta hydroxy groups, 3-alpha or 3-beta O-allyl groups, 3-alpha or 3-beta O-propargyl groups, 3-alpha or 3-beta O-glycol groups, 3-alpha or 3-beta O-PEG groups, 3-alpha or 3-beta O-glycol-allyl groups and 3-alpha or 3-beta O-PEG-allyl groups, wherein A can be a carbon atom substituted by an atom selected from the group of: 5-H alpha and 5-H beta, and wherein B is a methylene group, or wherein A and B are carbon atoms forming a 5,6-double bond;

wherein C can be a carbon atom substituted by an atom selected from the group consisting of: 14-H alpha, 14-H beta, 14-alpha OH group and 14-beta OH, and wherein D can be a methylene group; or wherein C and D can be carbon atoms forming a 14,15-double bond, wherein F is a carbon atom substituted by an atom selected from the group of: 17-H alpha and 17-H beta; and wherein E can be a methylene group or a carbon atom substituted by a group selected from the group of: 16-alkyl-alpha, 16-alkyl-beta, 16-$OR_2$-alpha and 16-$OR_2$-beta, wherein $R_2$ can be selected from the group of: an allyl, a propargyl, a glycol, a PEG, glycol-allyl, a PEG-allyl; or wherein F can be a carbon atom substituted by a group selected from the group of: 17-alkyl-alpha, 17-alkyl-beta, 17-$OR_2$-alpha and 17-$OR_2$-beta, wherein $R_2$ can be selected from the group of: an allyl, an O-propargyl, a glycol, a PEG, a glycol-allyl, a PEG-allyl; and wherein E can be a methylene group or a carbon atom substituted by group selected from the group of: 16-alkyl-alpha, 16-alkyl-beta, 16-$OR_2$-alpha and 16-$OR_2$-beta, where $R_2$ can be an allyl, propargyl, a glycol, a PEG, a glycol-allyl, a PEG-allyl; or wherein E and F together can form an epoxy cycle or a cyclopropyl and can be selected from the group of: 16,17-epoxy-alpha, 16,17-epoxy-beta, 16,17-methylene-alpha and 16,17-methylene-beta; or E and F can be carbon atoms forming a 16,17-double bond;

and wherein G can be a carbonyl, a methylene or a carbon atom substituted by a 12-$OR_3$-alpha or 12-$OR_3$-beta group, wherein $R_3$ can be an H atom or a group selected from the group consisting of: acetyl, alkyl and aryl groups. The neurosteroid or the analogue thereof or the derivative of the neruosteroid or the derivative of a neurosteroid analogue can be selected from the group of: compound (1), compound (2), compound (3), compound (4), compound (5), compound (6), compound (7), compound (8), compound (9), BR053, BR338, BR297, BR351, ganaxolone, and any combination thereof. The effective amount can range from about 0.325 mg/kg to about 15 mg/mg. The neuropsychiatric disorder can be an anxiety disorder. The neuropsychiatric disorder can be a post-traumatic stress disorder. The neuropsychiatric disorder can be a depression disorder. The depression disorder can be major depressive disorder. In some aspects, the subject in need there of has not responded to treatment with one or more selective-serotonin reuptake inhibitors.

The method can further include the step of detecting a biomarker for post-traumatic stress disorder (PTSD) in a sample from the subject in need thereof. The biomarker for PTSD is the amount of allopregnanolone in a bodily fluid sample of the subject in need thereof. The method can further include the step of deteing a biomarker for major depressive disorder in a bodily fluid sample of the subject in need thereof. The biomarker for major depressive disorder can be the amount of allopregnanolone in a bodily fluid sample of the subject in need thereof.

Also described herein are pharmaceutical formulations that can be composed of a therapeutically effective amount of a neurosteroid or an analogue thereof or a derivative of a neruosteroid or a derivative of a neurosteroid analogue effective to treat a neuropsychiatric disorder in a subject in need thereof; and a pharmaceutically acceptable carrier. The neurosteroid or the analogue thereof or the derivative of the neruosteroid or the derivative of a neurosteroid analogue can have a formula according to Formula (I)

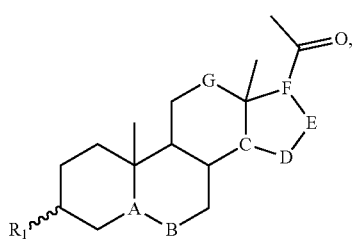

Formula (I)

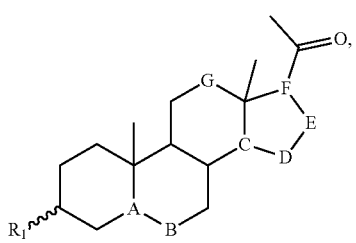

Formula (I)

wherein $R_1$ is selected from the group of: 3-alpha or 3-beta hydroxy groups, 3-alpha or 3-beta O-allyl groups, 3-alpha or 3-beta O-propargyl groups, 3-alpha or 3-beta O-glycol groups, 3-alpha or 3-beta O-PEG groups, 3-alpha or 3-beta O-glycol-allyl groups and 3-alpha or 3-beta O-PEG-allyl groups, wherein A can be a carbon atom substituted by an atom selected from the group of: 5-H alpha and 5-H beta, and wherein B is a methylene group, or wherein A and B are carbon atoms forming a 5,6-double bond;

wherein C can be a carbon atom substituted by an atom selected from the group consisting of: 14-H alpha, 14-H beta, 14-alpha OH group and 14-beta OH, and wherein D can be a methylene group; or wherein C and D can be carbon atoms forming a 14,15-double bond, wherein F is a carbon atom substituted by an atom selected from the group of: 17-H alpha and 17-H beta; and wherein E can be a methylene group or a carbon atom substituted by a group selected from the group of: 16-alkyl-alpha, 16-alkyl-beta, 16-$OR_2$-alpha and 16-$OR_2$-beta, wherein $R_2$ can be selected from the group of: an allyl, a propargyl, a glycol, a PEG, glycol-allyl, a PEG-allyl; or wherein F can be a carbon atom substituted by a group selected from the group of: 17-alkyl-alpha, 17-alkyl-beta, 17-$OR_2$-alpha and 17-$OR_2$-beta, wherein $R_2$ can be selected from the group of: an allyl, an O-propargyl, a glycol, a PEG, a glycol-allyl, a PEG-allyl; and wherein E can be a methylene group or a carbon atom substituted by group selected from the group of: 16-alkyl-alpha, 16-alkyl-beta, 16-$OR_2$-alpha and 16-$OR_2$-beta, where $R_2$ can be an allyl, propargyl, a glycol, a PEG, a glycol-allyl, a PEG-allyl; or wherein E and F together can form an epoxy cycle or a cyclopropyl and can be selected from the group of: 16,17-epoxy-alpha, 16,17-epoxy-beta, 16,17-methylene-alpha and 16,17-methylene-beta; or E and F can be carbon atoms forming a 16,17-double bond; and wherein G can be a carbonyl, a methylene or a carbon atom substituted by a 12-$OR_3$-alpha or 12-$OR_3$-beta group, wherein $R_3$ can be an H atom or a group selected from the group consisting of: acetyl, alkyl and aryl groups. The neurosteroid or the analogue thereof or the derivative of the neruosteroid or the derivative of a neurosteroid analogue can be selected from the group of: compound (1), compound (2), compound (3), compound (4), compound (5), compound (6), compound (7), compound (8), compound (9), BR053, BR338, BR297, BR351, ganaxolone, and any combination thereof. The effective amount can range from about 0.325 mg/kg to about 15 mg/mg.

Also described herein are kits for treating a neuropsychiatric disorder in a subject in need thereof, that in some aspects can include a pharmaceutical formulation comprising an effective amount of a compound according to Formula (I)

wherein $R_1$ is selected from the group of: 3-alpha or 3-beta hydroxy groups, 3-alpha or 3-beta O-allyl groups, 3-alpha or 3-beta O-propargyl groups, 3-alpha or 3-beta O-glycol groups, 3-alpha or 3-beta O-PEG groups, 3-alpha or 3-beta O-glycol-allyl groups and 3-alpha or 3-beta O-PEG-allyl groups, wherein A can be a carbon atom substituted by an atom selected from the group of: 5-H alpha and 5-H beta, and wherein B is a methylene group, or wherein A and B are carbon atoms forming a 5,6-double bond;

wherein C can be a carbon atom substituted by an atom selected from the group consisting of: 14-H alpha, 14-H beta, 14-alpha OH group and 14-beta OH, and wherein D can be a methylene group; or wherein C and D can be carbon atoms forming a 14,15-double bond, wherein F is a carbon atom substituted by an atom selected from the group of: 17-H alpha and 17-H beta; and wherein E can be a methylene group or a carbon atom substituted by a group selected from the group of: 16-alkyl-alpha, 16-alkyl-beta, 16-$OR_2$-alpha and 16-$OR_2$-beta, wherein $R_2$ can be selected from the group of: an allyl, a propargyl, a glycol, a PEG, glycol-allyl, a PEG-allyl; or wherein F can be a carbon atom substituted by a group selected from the group of: 17-alkyl-alpha, 17-alkyl-beta, 17-$OR_2$-alpha and 17-$OR_2$-beta, wherein $R_2$ can be selected from the group of: an allyl, an O-propargyl, a glycol, a PEG, a glycol-allyl, a PEG-allyl; and wherein E can be a methylene group or a carbon atom substituted by group selected from the group of: 16-alkyl-alpha, 16-alkyl-beta, 16-$OR_2$-alpha and 16-$OR_2$-beta, where $R_2$ can be an allyl, propargyl, a glycol, a PEG, a glycol-allyl, a PEG-allyl; or wherein E and F together can form an epoxy cycle or a cyclopropyl and can be selected from the group of: 16,17-epoxy-alpha, 16,17-epoxy-beta, 16,17-methylene-alpha and 16,17-methylene-beta; or E and F can be carbon atoms forming a 16,17-double bond;

and wherein G can be a carbonyl, a methylene or a carbon atom substituted by a 12-$OR_3$-alpha or 12-$OR_3$-beta group, wherein $R_3$ can be an H atom or a group selected from the group consisting of: acetyl, alkyl and aryl groups; and a pharmaceutically acceptable carrier.

The neurosteroid or the analogue thereof or the derivative of the neruosteroid or the derivative of a neurosteroid analogue can be selected from the group of: compound (1), compound (2), compound (3), compound (4), compound (5), compound (6), compound (7), compound (8), compound (9), BR053, BR338, BR297, BR351, ganaxolone, and any combination thereof. The effective amount can range from about 0.325 mg/kg to about 15 mg/mg. The neuropsychiatric disorder can be post-traumatic stress disorder or major depressive disorder.

BRIEF DESCRIPTION OF THE DRAWINGS

Further aspects of the present disclosure will be readily appreciated upon review of the detailed description of its various aspects, described below, when taken in conjunction with the accompanying drawings.

Allo and its stereoisomer pregnanolone (PA) are primarily synthesized in glutamatergic neurons and play a central neuromodulatory role in facilitating the action of GABA at $GABA_A$ receptors (a primary target of anxiolytics) and in the fine-tuning of the receptor for agonists and GABA mimetic agents. The finding that Allo facilitates the efficacy of $GABA_A$ receptor allosteric modulators substantiates its endogenous physiological relevance. Neurosteroids can act on $GABA_A$ receptor or on NMDA receptor (sulfated steroids). Allo and PA binding at $GABA_A$ receptors result in behavioral responses, including anti-aggressive, anxiolytic and anti-fear actions; the binding of sulfated Allo and PA inhibit tonic-activated NMDA neurotransmission which result in important repercussions on neuroplasticity, memory formation and learning processes.

The right panel shows the peripheral alterations of eCBs and neurosteroids in patients. It is evident that the modified concentrations of eCBs and neurosteroids present common alterations. The endocannabinoid and neurosteroid system interface, including the action at their receptors (e.g., PPAR-α, CB1 and GABAA and NMDA receptors) may provide an important biomarker axis to selectively predict, diagnose, and establish the best individualized treatment selection for MDD and PTSD patients.

Figure 10:
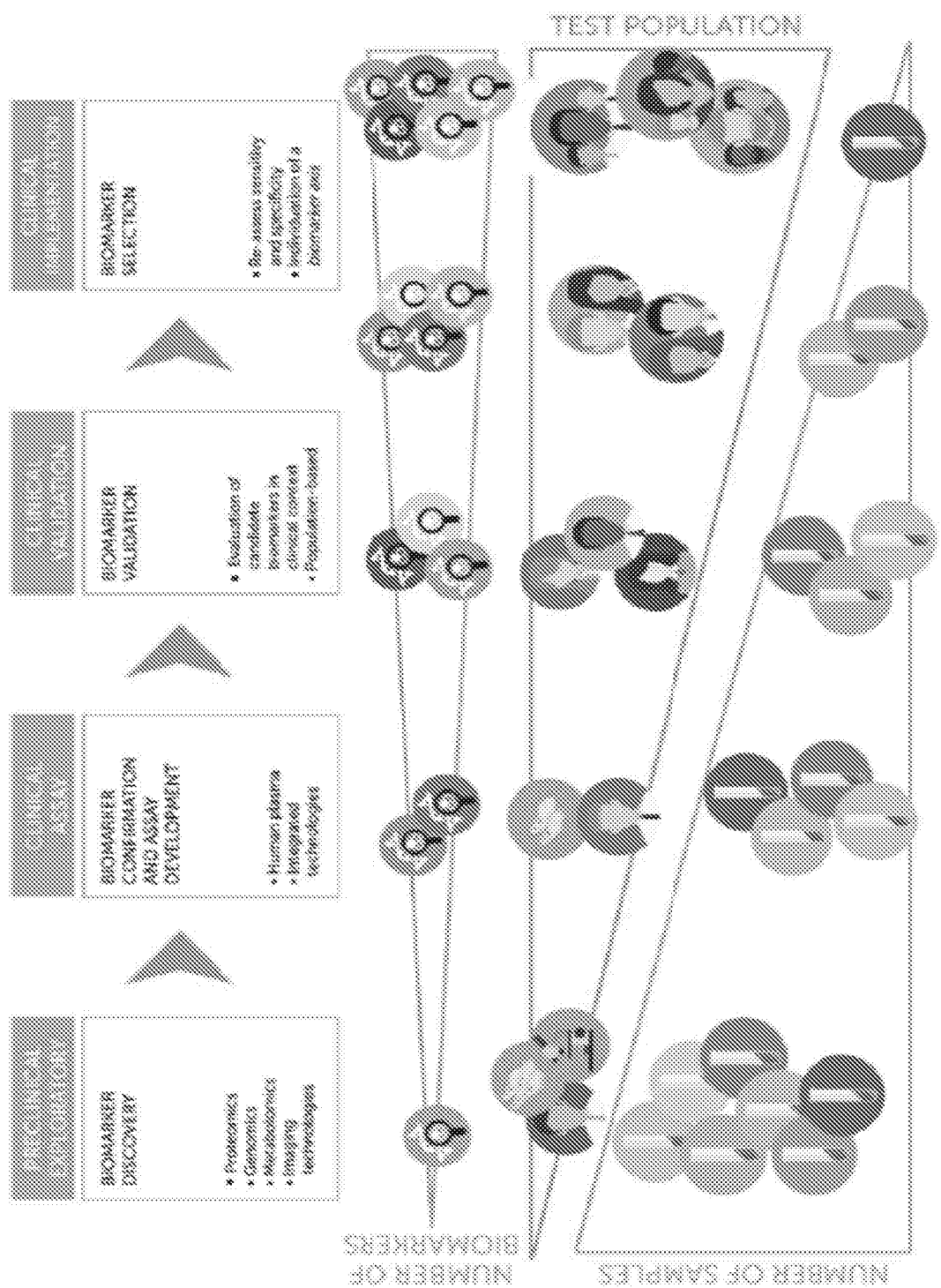

FIG. 10 shows a schematic that can illustrate the process of biomarker-based test assessment. The process that leads to the selection of a biomarker is useful to predict, diagnose and treat psychiatric disorders or test individual susceptibility is articulated in several phases. From the preclinical search to the final selection the number of samples necessary diminishes and assessment of biomarkers becomes available for a large number of individual. Biomarker discovery for potential biomarkers, mainly on animal models, is a long process that requires validation on human samples through different sophisticated technologies, such as gas chromatography-mass spectrometry (GC-MS). Once the biomarker has been established, it has to be validated with a clinical procedure on the population. After this phase, the biomarker selected will go through clinical implementation that improves the specificity and sensitivity of the marker. When more biomarkers are confirmed, it is possible to identify a biomarker axis that allows a precise diagnosis and individualized treatments.

Figure 11:
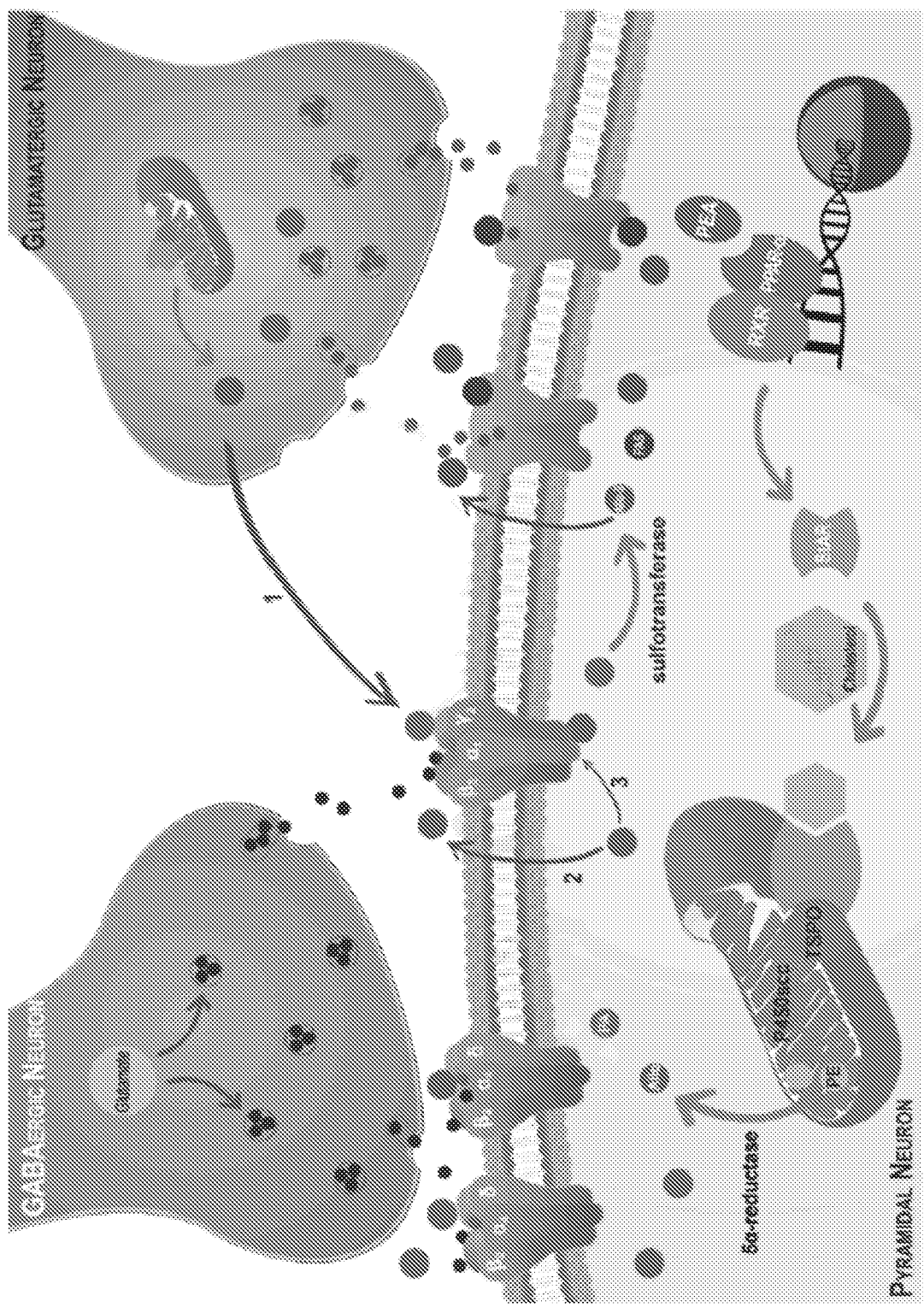

FIG. 11 shows a schematic that can demonstrate the regulation of emotional behavior via endocannabinoid and neurosteroid systems cross-talk.

Figure 12:
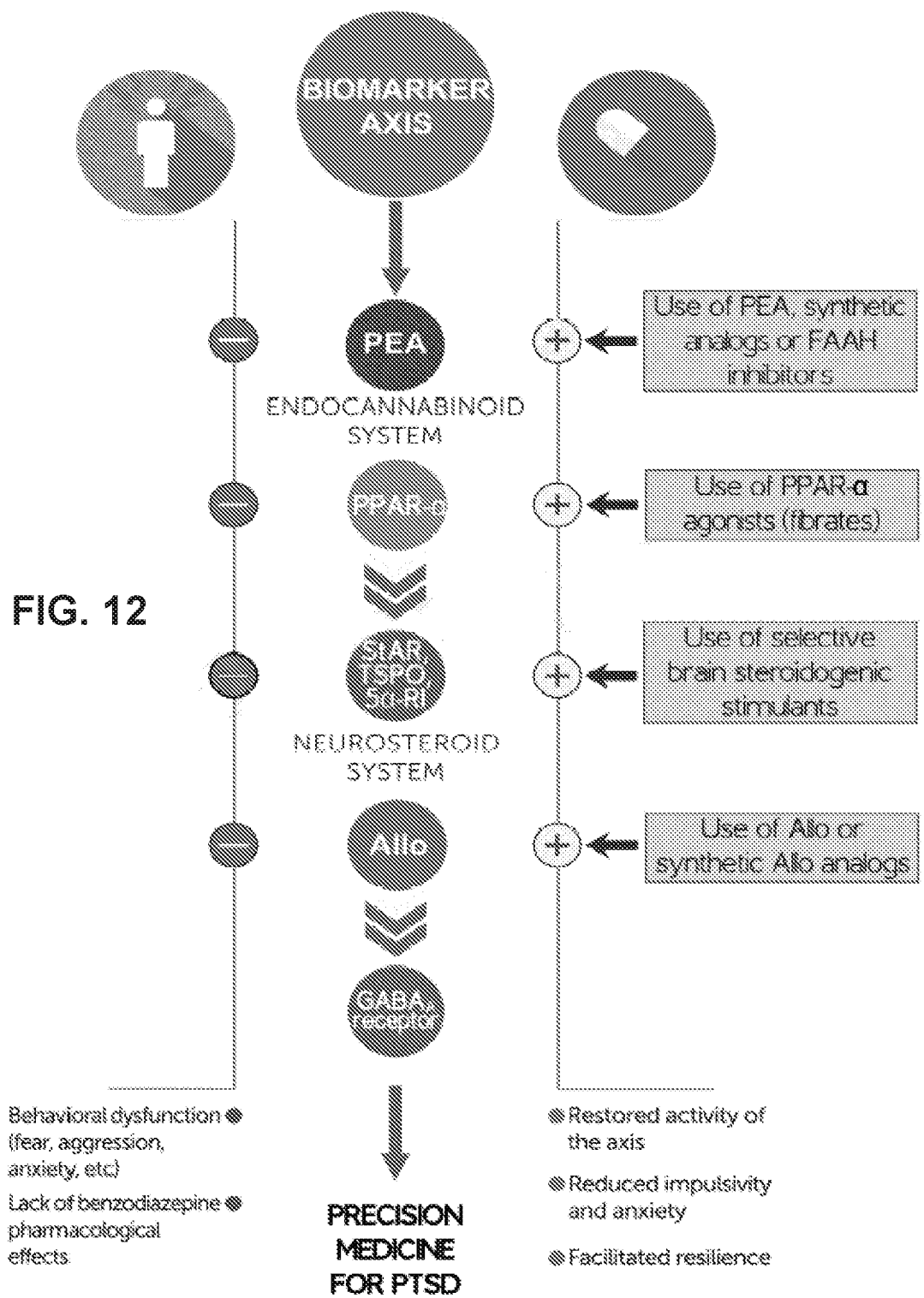

FIG. 12 shows a schematic that can demonstrate the biomarker axis at the interface of the endocannabinoid and neurosteroid systems.

DETAILED DESCRIPTION

Before the present disclosure is described in greater detail, it is to be understood that this disclosure is not limited to particular aspects described, and as such may, of course, vary. It is also to be understood that the terminology used herein is for the purpose of describing particular aspects only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual aspects described and illustrated herein has discrete components and features which may be readily separated from or combined with the features of any of the other several aspects without departing from the scope or spirit of the present disclosure. Any recited method can be carried out in the order of events recited or in any other order that is logically possible.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, "about," "approximately," "substantially," and the like, when used in connection with a numerical variable, can generally refers to the value of the variable and to all values of the variable that are within the experimental error (e.g., within the 95% confidence interval for the mean) or within +/−10% of the indicated value, whichever is greater. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

Aspects of the present disclosure will employ, unless otherwise indicated, techniques of molecular biology, microbiology, organic chemistry, biochemistry, physiology, cell biology, cancer biology, and the like, which are within the skill of the art. Such techniques are explained fully in the literature.

Definitions

As used herein, "active agent" or "active ingredient" can refer to a substance, compound, or molecule, which is biologically active or otherwise, induces a biological or physiological effect on a subject to which it is administered to. In other words, "active agent" or "active ingredient" refers to a component or components of a composition to which the whole or part of the effect of the composition is attributed.

As used herein, "administering" can refer to an administration that is oral, topical, intravenous, subcutaneous, transcutaneous, transdermal, intramuscular, intra-joint, parenteral, intra-arteriole, intradermal, intraventricular, intraosseous, intraocular, intracranial, intraperitoneal, intralesional, intranasal, intracardiac, intraarticular, intracavernous, intrathecal, intravireal, intracerebral, and intracerebroventricular, intratympanic, intracochlear, rectal, vaginal, by inhalation, by catheters, stents or via an implanted reservoir or other device that administers, either actively or passively (e.g. by diffusion) a composition the perivascular space and adventitia. For example a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, "agent" can refer to any substance, compound, molecule, and the like, which can be biologically active or otherwise can induce a biological and/or physiological effect on a subject to which it is administered to. An agent can be a primary active agent, or in other words, the component(s) of a composition to which the whole or part of the effect of the composition is attributed. An agent can be a secondary agent, or in other words, the component(s) of a composition to which an additional part and/or other effect of the composition is attributed.

As used herein, "active agent" or "active ingredient" can refer to a substance, compound, or molecule, which is biologically active or otherwise, induces a biological or physiological effect on a subject to which it is administered to. In other words, "active agent" or "active ingredient" refers to a component or components of a composition to which the whole or part of the effect of the composition is attributed.

As used herein, "control" can refer to an alternative subject or sample used in an experiment for comparison purpose and included to minimize or distinguish the effect of variables other than an independent variable.

As used herein, "dose," "unit dose," or "dosage" can refer to physically discrete units suitable for use in a subject, each unit containing a predetermined quantity of the self-assembling cyclopeptide-dye compounds and/or a formulation thereof calculated to produce the desired response or responses in association with its administration.

As used herein, "derivative" can refer to any compound having the same or a similar core structure to the compound but having at least one structural difference, including substituting, deleting, and/or adding one or more atoms or functional groups. The term "derivative" does not mean that the derivative is synthesized from the parent compound either as a starting material or intermediate, although this may be the case. The term "derivative" can include prodrugs, or metabolites of the parent compound. Derivatives include compounds in which free amino groups in the parent compound have been derivatized to form amine hydrochlorides, p-toluene sulfoamides, benzoxycarboamides, t-butyloxycarboamides, thiourethane-type derivatives, trifluoroacetylamides, chloroacetylamides, or formamides. Derivatives include compounds in which carboxyl groups in the parent compound have been derivatized to form methyl and ethyl esters, or other types of esters or hydrazides. Derivatives include compounds in which hydroxyl groups in the parent compound have been derivatized to form O-acyl or O-alkyl derivatives. Derivatives include compounds in which a hydrogen bond donating group in the parent compound is replaced with another hydrogen bond donating group such as OH, NH, or SH. Derivatives include replacing a hydrogen bond acceptor group in the parent compound with another hydrogen bond acceptor group such as esters, ethers, ketones, carbonates, tertiary amines, imine, thiones, sulfones, tertiary amides, and sulfides. "Derivatives" also includes extensions of the replacement of the cyclopentane ring with saturated or unsaturated cyclohexane or other more complex, e.g., nitrogen-containing rings, and extensions of these rings with side various groups.

As used herein, "effective amount" can refer to the amount of a compound provided herein that is sufficient to effect beneficial or desired biological, emotional, medical, or clinical response of a cell, tissue, system, animal, or human. An effective amount can be administered in one or more administrations, applications, or dosages. The term cam also include within its scope amounts effective to enhance or restore to substantially normal physiological function. The "effective amount" can refer to the amount of the neurosteroid or analogue thereof described herein or formulation thereof described herein that can treat and/or prevent a neuropsychiatric disorder or a symptom thereof. In some aspects, the "effective amount" can refer to the amount of the neurosteroid or analogue thereof described herein or formulation thereof described herein that can treat and/or prevent post-traumatic stress disorder or a symptom thereof. In some aspects, the "effective amount" can refer to the amount of the neurosteroid or analogue thereof described herein or formulation thereof described herein that can treat and/or prevent anxiety in a subject.

The term "molecular weight", as used herein, can generally refer to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

As used herein, "organism", "host", "patient", and "subject" refers to any living entity comprised of at least one cell. A living organism can be as simple as, for example, a single isolated eukaryotic cell or cultured cell or cell line, or as complex as a mammal, including a human being, and animals (e.g., vertebrates, amphibians, fish, mammals, e.g., cats, dogs, horses, pigs, cows, sheep, rodents, rabbits, squirrels, bears, primates (e.g., chimpanzees, gorillas, and humans).

As used herein "peptide" can refer to chains of at least 2 amino acids that are short, relative to a protein or polypeptide.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo. Pharmaceutical formulation includes any acceptable pharmaceutically acceptable salts of the active ingredient(s).

As used herein, "pharmaceutically acceptable carrier or excipient" can refer to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used herein, "pharmaceutically acceptable salt" can refer to any acid or base addition salt whose counter-ions are non-toxic to the subject to which they are administered in pharmaceutical doses of the salts.

As used herein, "preventative" and "prevent" can refer to hindering or stopping a disease or condition before it occurs, even if undiagnosed, or while the disease or condition is still in the sub-clinical phase.

As used herein, "substantially pure" can mean an object species is the predominant species present (i.e., on a molar basis it is more abundant than any other individual species in the composition), and preferably a substantially purified fraction is a composition wherein the object species comprises about 50 percent of all species present. Generally, a substantially pure composition will comprise more than about 80 percent of all species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single species.

As used interchangeably herein, the terms "sufficient" and "effective," can refer to an amount (e.g. mass, volume, dosage, concentration, and/or time period) needed to achieve one or more desired result(s). For example, a therapeutically effective amount refers to an amount needed to achieve one or more therapeutic effects.

As used herein, "therapeutic" can refer to treating, healing, and/or ameliorating a disease, disorder, condition, or side effect, or to decreasing in the rate of advancement of a disease, disorder, condition, or side effect. A "therapeutically effective amount" can therefore refer to an amount of a compound that can yield a therapeutic effect.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as a neuropsychiatric disorder (including, but not limited to, PTSD, or a symptom thereof. Others are described elsewhere herein). The effect can be therapeutic in terms of a partial or complete cure of a disease, condition, symptom or adverse effect attributed to the disease, disorder, or condition. The term "treatment" as used herein covers any treatment of a neuropsychiatric disorder (including, but not limited to, PTSD or a symptom thereof), in a subject, particularly a human, and can include any one or more of the following: (a) preventing the disease from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic (preventative) treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

As used herein, "alkyl" and "alkylene" refer to a saturated hydrocarbon chain having the specified number of member atoms.

The term "alkyl" can also refer to the radical of saturated aliphatic groups (i.e., an alkane with one hydrogen atom removed), including straight-chain alkyl groups, branched-chain alkyl groups, cycloalkyl (alicyclic) groups, alkyl-substituted cycloalkyl groups, and cycloalkyl-substituted alkyl groups. "Alkyl" also refers to a saturated hydrocarbon chain having the specified number of atoms.

The term "alkyl" (or "lower alkyl") as used herein can include both "unsubstituted alkyls" and "substituted alkyls," the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein can refer to an alkyl group, as defined above, but having from one to ten carbons in its backbone structure. Likewise, "lower alkenyl" and "lower alkynyl" have similar chain lengths.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF$_3$, —CN and the like. Cycloalkyls can be substituted in the same manner.

As used herein, "C$_{1-6}$alkyl" can refer to an alkyl group having any number of member atoms from 1 to 6 member atoms, such as for example 1 to 4 atoms. Other alkyl groups may have any number of member atoms as indicated by the numbers given in the formula, which, like the previous example, can refer to an alkyl group having any number of member atoms within the specified range of member atoms. Alkyl groups may be straight or branched. Representative branched alkyl groups have one, two, or three branches. Alkyl includes methyl, ethyl, propyl (n-propyl and isopropyl), butyl (n-butyl, isobutyl, and t-butyl), pentyl (n-pentyl, isopentyl, and neopentyl), and hexyl.

As used herein, "heterocyclic group" can refer to a non-aromatic ring and having the specified number of member atoms being saturated or having one or more degrees of unsaturation and, unless otherwise specified, containing one or more heteroatoms.

As used herein, "heteroaryl" can refer to an aromatic ring having the specified number of member atoms and, unless otherwise specified, containing one or more heteroatoms. Bicyclic and other polycyclic ring systems having a heteroaryl ring are described as fused systems.

The term "heteroalkyl," as used herein, can refer to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "heteroalkyl," as used herein, can refer to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

As used herein, "alkoxyl" or "alkoxy," as used herein, can refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl is an ether or resembles an alkoxyl, such as can be represented by one of —O-alkyl, —O— alkenyl, and —O-alkynyl. The terms "aroxy" and "aryloxy", as used interchangeably herein, can be represented by —O-aryl or O-heteroaryl, wherein aryl and heteroaryl are as defined below. The alkoxy and aroxy groups can be substituted as described above for alkyl.

As used herein, "amine" and "amino" (and its protonated form) are art-recognized and refer to both unsubstituted and substituted amines, e.g., a moiety that can be represented by the general formula:

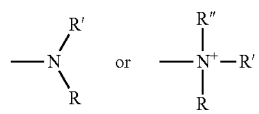

wherein R, R', and R" each independently represent a hydrogen, an alkyl, an alkenyl, —(CH$_2$)$_m$—R$_c$ or R and R' taken together with the N atom to which they are attached complete a heterocycle having from 4 to 8 atoms in the ring structure; R$_c$ represents an aryl, a cycloalkyl, a cycloalkenyl, a heterocycle or a polycycle; and m is zero or an integer in the range of 1 to 8. In some aspects, only one of R or R' can be a carbonyl, e.g., R, R' and the nitrogen together do not form an imide. In other aspects, the term "amine" does not encompass amides, e.g., wherein one of R and R' represents a carbonyl. In further aspects, R and R' (and optionally R") each independently represent a hydrogen, an alkyl or cycloakyl, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of R and R' is an alkyl group.

As used herein, "amido" is art-recognized as an amino-substituted carbonyl and includes a moiety that can be represented by the general formula:

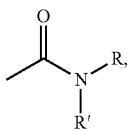

wherein R and R' are as defined above.

As used herein, "Aryl" can refer to $C_5$-$C_{10}$-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine, pyrimidine, and the like. Those aryl groups having heteroatoms in the ring structure may also be referred to as "aryl heterocycles" or "heteroaromatics." The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, and combinations thereof.

The term "aryl" can also include polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. One or more of the rings can be substituted as defined above for "aryl."

As used herein, "aralkyl," can refer to an alkyl group substituted with an aryl group (e.g., an aromatic or heteroaromatic group).

As used herein, "aralkyloxy" can be represented by —O-aralkyl, wherein aralkyl is as defined above.

As used herein, "carbocycle," can refer to an aromatic or non-aromatic ring(s) in which each atom of the ring(s) is carbon.

As used herein, "heterocycle" or "heterocyclic" can refer to a monocyclic or bicyclic structure containing 3-10 ring atoms, and in some aspects, containing from 5-6 ring atoms, wherein the ring atoms are carbon and one to four heteroatoms each selected from the following group of non-peroxide oxygen, sulfur, and N(Y) wherein Y is absent or is H, O, ($C_1$-$C_{10}$) alkyl, phenyl or benzyl, and optionally containing 1-3 double bonds and optionally substituted with one or more substituents. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. Heterocyclic groups can optionally be substituted with one or more substituents at one or more positions as defined above for alkyl and aryl, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbonyl" is art-recognized and includes such moieties as can be represented by the general formula:

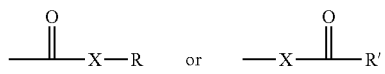

wherein X is a bond or represents an oxygen or a sulfur, and R and R' are as defined above. Where X is an oxygen and R or R' is not hydrogen, the formula represents an "ester". Where X is an oxygen and R is as defined above, the moiety is referred to herein as a carboxyl group, and particularly when R is a hydrogen, the formula represents a "carboxylic acid." Where X is an oxygen and R' is hydrogen, the formula represents a "formate." In general, where the oxygen atom of the above formula is replaced by sulfur, the formula represents a "thiocarbonyl" group. Where X is a sulfur and R or R' is not hydrogen, the formula represents a "thioester." Where X is a sulfur and R is hydrogen, the formula represents a "thiocarboxylic acid." Where X is a sulfur and R' is hydrogen, the formula represents a "thioformate." On the other hand, where X is a bond, and R is not hydrogen, the above formula represents a "ketone" group. Where X is a bond, and R is hydrogen, the above formula represents an "aldehyde" group.

As used herein, "heteroatom" as used herein can refer to an atom of any element other than carbon or hydrogen. Exemplary heteroatoms include, but are not limited to, boron, nitrogen, oxygen, phosphorus, sulfur, silicon, arsenic, and selenium.

As used herein, "nitro" can refer to $-NO_2$; the term "halogen" designates $-F$, $-Cl$, $-Br$, or $-I$; the term "sulfhydryl" refers to $-SH$; the term "hydroxyl" refers to $-OH$; and the term "sulfonyl" refers to $-SO_2-$.

The term "substituted" as used herein, can refer to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, e.g. 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups.

Heteroatoms, such as nitrogen, can have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e., a compound that does not spontaneously undergo transformation such as by rearrangement, cyclization, elimination, etc.

As used herein, "suitable substituent" can refer to a chemically and pharmaceutically acceptable group, i.e., a moiety that does not significantly interfere with the preparation of or negate the efficacy of the inventive compounds. Such suitable substituents may be routinely chosen by those skilled in the art. Suitable substituents include but are not limited to the following: a halo, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, $C_2$-$C_6$ alkynyl, $C_3$-$C_8$ cycloalkenyl, ($C_3$-$C_8$ cycloalkyl)$C_1$-$C_6$ alkyl, ($C_3$-$C_8$ cycloalkyl)$C_2$-$C_6$ alkenyl, ($C_3$-$C_8$ cycloalkyl) $C_1$-$C_6$ alkoxy, $C_3$-$C_7$ heterocycloalkyl, ($C_3$-$C_7$ heterocycloalkyl) $C_1$-$C_6$ alkyl, ($C_3$-$C_{07}$ heterocycloalkyl)$C_2$-$C_6$ alkenyl, ($C_3$-$C_7$ heterocycloalkyl)$C_1$-$C_6$ alkoxyl, hydroxy, carboxy, oxo, sulfanyl, $C_1$-$C_6$ alkylsulfanyl, aryl, heteroaryl, aryloxy, heteroaryloxy, arylalkyl, heteroaralkyl, arylalkoxy, heteroaralkoxy, nitro, cyano, amino, $C_1$-$C_6$ alkylamino, di-($C_1$-$C_6$ alkyl)amino, carbamoyl, ($C_1$-$C_6$ alkyl)carbonyl, ($C_1$-$C_6$ alkoxy)carbonyl, ($C_1$-$C_6$ alkyl)aminocarbonyl, di-($C_1$-$C_6$ alkyl)aminocarbonyl, arylcarbonyl, aryloxycarbonyl, ($C_1$-$C_6$ alkyl)sulfonyl, and arylsulfonyl. The groups listed above as suitable substituents are as defined hereinafter except that a suitable substituent may not be further optionally substituted.

As used herein, "optionally substituted" can indicate that a group may be unsubstituted or substituted with one or more substituents as defined herein.

Discussion

Neuropsychiatric disorders are generally diseases, conditions, and disorders of affect, cognition, and/or behavior that can arise from an overt disorder in cerebral function or from indirect effects of extracerebral diseases and disorders. Neuropsychiatric disorders are a significant burden on society and can impair the health of those affected, as well as their ability to learn, work, and/or emotionally cope. They also can burden those not afflicted in that those affected often must rely on caregivers or other forms of assistance due to their inability to fully engage and function in normal work and life activities. Non-limiting examples of neuropsychiatric disorders include addiction, developmental conditions (e.g. attention deficit hyperactivity disorder (ADHD), autism, fetal alcohol syndrome, and tic disorders), eating disorders, degenerative disease (e.g. dementia, Parkinson's disease, and Alzheimer's disease), mood/affect disorders (e.g. bipolar disorder, depressions, and mania), neurotic disorders (e.g. obsessive compulsive disorder, trichotillomania, and anxiety disorders (including post-traumatic stress disorder (PTSD)), psychosis (e.g. schizophrenia), and sleep disorders (e.g. sleep apnea, narcolepsy, insomnia, and parasomnia).

Anxiety disorders, including PTSD, affect 8-13% of the population and as much as 25% of soldiers who have spent time in war zones, with an additional 30% have had partial PTSD at some point in their lives. PTSD is marked by clear biological changes as well as psychological symptoms. PTSD is complicated by the fact that people having PTSD often have or develop co-disorders such as depression, substance abuse, problems with memory and cognition, and other problems of physical and mental health. It is reported that up to 80% of Vietnam veterans seeking PTSD treatment abuse alcohol. PTSD is also associated with impairment of the person's ability to function in normal social and/or family live, including occupational instability, marital problems and divorces, family discord, and difficulties parenting.

The benefits and health care costs associated with just veterans affected by PTSD are enormous. The U.S. Congressional Budget Office shows that since Sep. 11, 2001, more than 2.2 million US service members have been deployed to war zones. Among them 1.4 million Afghan and Iraq war veterans are eligible for VA healthcare. About 712,000 patients are treated by the VA and about half of them (about 367,000) are treated for mental healthcare conditions. Patients that have been treated for PTSD account for more than half (about 212,000) of those being treated for mental healthcare conditions. According to the Veteran Health Administration, there are about 10,000 new veteran patients each month.

Benzodiazepines are the most used anxiolytics, but their use is associated with sedation, tolerance, dependence, and severe withdrawal symptoms. Further they are ineffective in those with PTSD. Conventional PTSD treatments include exposure-based therapy (EBT). EBT involves the exposure of the patient to the feared context without any danger, in order to allow the patient to overcome the motivation of their anxiety. This is similar to the procedure used to simulate and study fear responses and fear extinction learning in PTSD mouse models. Generally, psychological therapy has been effective both to treat PTSD and prevent the progression of the event sequelae that leads to the consolidation of fear memories resulting from an acute stress and the development of PTSD.

Despite the reported success of psychological therapy, there are challenges associated with the treatment of PTSD with this modality of treatment. One of the challenges associated with PTSD psychological therapy is the spontaneous recovery of fear that often reemerges a time after conclusion of successful EBT. As such, pharmacological treatment can be advantageous alone or in combination with psychological therapy such as EBT.

Major depressive (MDD) disorder is the most common neuropsychiatric disease worldwide and is often comorbid with other neuropsychiatric conditions such as generalized anxiety and substance abuse disorder. Exposure to traumatic conditions, including abuse, combat situations, or sexual assault can result in a particularly serious form of PTSD that is often comorbid with MDD.

Selective serotonin reuptake inhibitors (SSRIs) are the class of drugs that are conventionally used for treating anxiety and depression disorders. SSRIs can be effective in facilitating and restoring the neurobiological changes altered in PTSD and depressed patients and are typically devoid of the unwanted side effects that plague the benzodiazepines. SSRIs are can be useful for the treatment of patients with PTSD where benzodiazepines have failed to be beneficial. However, currently available SSRIs are not without their drawbacks. Some SSRIs have significant and intolerable side effects. Further, SSRIs have been reported to have varying benefit and can be ineffective in some patients.

With that said, described herein neurosteroids, including but not limited to allopregnanolone ("Allo") and analogues thereof and derivatives thereof that can be administered to a subject in need thereof to treat and/or prevent a neuropsychiatric disorder in the subject. The neuropsychiatric disorder can be an anxiety disorder, including but not limited to, PTSD or MDD. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description and be within the scope of the present disclosure.

Neurosteriods, Anoloques Thereof, Derivatives Thereof and Pharmaceutical Formulations Thereof Neurosteroids are steroids that can alter neuronal excitability through non-genomic actions (e.g. action at membrane surface receptors and ligand gated ion channels). Allopregnanolone (abbreviated as "Allo" elsewhere herein) is an example neurosteroid that is endogenously synthesized by post-synaptic neurons from progesterone and can act via retrograde synaptic action at pre-synaptic $GABA_A$ receptors. In the brain, Allo can be synthesized from progesterone by the sequential action of 5alpha-reductase type I (5α-RI), which can reduces progesterone into 5alpha-dihydro-progesterone (5alpha-DHP); 3alpha-hydroxyseroid-dehydrogenase (3alpha-HSD) then converts 5alpha-DHP into Allo via a reduction reaction. 3alpha-HSD can also convert Allo into and 5alpha-DHP via an oxidation reaction. Allo and 5alpha-DHP are unevenly distributed in the mouse brain. Despite the neurotransmitter phenotype (glutamatergic or GABAergic), 5α-RI and 3alpha-HSD are highly expressed in pyramidal, granular cells, reticulo-thalamic medium spiny neurons, and Purkinje neurons and are absent in interneurons and glial cells.

Allo's action is dependent on neuron-type. In glutamatergic nerons, upon secretion, Allo can act in a paracrine fashion at $GABA_A$ receptors located on cell bodies or dendrites of distal pyramidal neurons. Allo can act in an autocrine manner at $GABA_A$ receptors located on glutamatergic neurons dendrites or cell bodies. Allo can access and act at the intracellular sites of $GABA_A$ receptors. Decreased Allo levels and/or reduced Allo biosynthesis can be observed to result in a GABAnergic neurotransmission dysfunction as characterized by a weaker response to the pharmacological action of muscimol, alcohol, pentobarbital, or BDZ, anxiety, and exaggerated contextual fear responses.

Described herein are neurosteroids and analogues thereof, such as Allo (compound (1)) and analogues thereof, and pharmaceutical formulations of these compounds that can be capable treating a neuropsychiatric disorder in a subject to which it is administered. Those neuropsychiatric disorders, including but not limited to anxiety disorders (e.g. PTSD) and depression disorders (such as MDD).

In some aspects, the neurosteroid or analogue or derivative thereof can have a formula according to Formula I

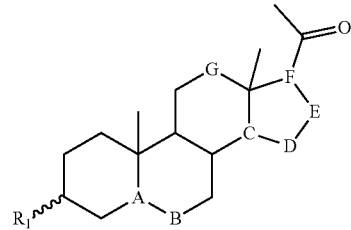

Formula (I)

where $R_1$ can be a group chosen among the following: 3-alpha or 3-beta hydroxy groups, 3-alpha or 3-beta O-allyl groups, 3-alpha or 3-beta O-propargyl groups, 3-alpha or 3-beta O-glycol groups, 3-alpha or 3-beta O-PEG groups, 3-alpha or 3-beta O-glycol-allyl groups and 3-alpha or 3-beta O-PEG-allyl groups, A can be a carbon atom that can be substituted by an atom chosen among 5-H alpha and 5-H beta and B can be a methylene group; or A and B can be carbon atoms forming a 5,6-double bond;

C can be a carbon atom substituted by an atom chosen among 14-H alpha, 14-H beta, 14-alpha OH group and 14-beta OH and D is a methylene group; or C and D can be carbon atoms forming a 14,15-double bond;

F can be a carbon atom substituted by an atom chosen among 17-H alpha and 17-H beta and E can be a methylene group or a carbon atom substituted by a group chosen among 16-alkyl-alpha, 16-alkyl-beta, 16-$OR_2$-alpha and 16-$OR_2$- beta, where R₂ can be chosen among an allyl, a propargyl, a glycol, a PEG, glycol-allyl, a PEG-allyl; or F can be a carbon atom substituted by a group chosen among 17-alkyl-alpha, 17-alkyl-beta, 17-OR₂-alpha and 17-OR₂-beta, where R₂ can be chosen among an allyl, an O-propargyl, a glycol, a PEG, a glycol-allyl, a PEG-allyl, and E can be a methylene group or a carbon atom substituted by group chosen among 16-alkyl-alpha, 16-alkyl-beta, 16-OR₂-alpha and 16-OR₂-beta, where R₂ can be an allyl, propargyl, a glycol, a PEG, a glycol-allyl, a PEG-allyl; or E and F are involved in an epoxy cycle or a cyclopropyl and are chosen among 16,17-epoxy-alpha, 16,17-epoxy-beta, 16,17-methylene-alpha and 16,17-methylene-beta; or E and F can be carbon atoms forming a 16,17-double bond;

G can be a carbonyl, a methylene or a carbon atom substituted by a 12-OR₃-alpha or 12-OR₃-beta group where R₃ can be a H atom or a group chosen among the acetyl, alkyl and aryl groups. In some aspects, R₃ can be chosen among ci-c6-alkyl, benzyl, p-methoxybenzyl, benzoyl, tigloyl, angeloyl, 2,2,2-trichloroethoxycarbonyl, o-aminobenzoyl, nicotinoyl, 2-methylbutyryl, isovaleryl, cinnamoyl, coumaroyl, o-hydroxybenzoyl and anthraniloyl.

In some aspects, the neurosteroid or analogue or derivative thereof can be according to Formula (I), wherein R₁ is a group chosen among the following: 3-alpha or 3-beta O-allyl groups, the 3-alpha or 3-beta O-propargyl groups, the 3-alpha or 3-beta O-glycol groups, the 3-alpha or 3-beta O-PEG groups, the 3-alpha or 3-beta O-glycol-allyl groups and 3-alpha or 3-beta O-PEG-allyl groups, A can be a carbon atom substituted by an atom chosen among 5-H alpha and 5-H beta and B is a methylene group; or A and B can be carbon atoms forming a 5,6-double bond;

C can be a carbon atom substituted by an atom chosen among 14-H alpha, 14-H beta, 14-alpha OH and 14-beta OH and D is a methylene group; or C and D can be carbon atoms forming a 14,15-double bond;

F can be a carbon atom substituted by an atom chosen among 17-H alpha and 17-H beta, and E can be a methylene group or a carbon atom substituted by a group chosen among 16-alkyl-alpha, 16-alkyl-beta, 16-OR₂-alpha and 16-OR₂-beta, where R₂ can be chosen among an allyl, a propargyl, a glycol, PEG, a glycol-allyl, a PEG-allyl; or F can be a carbon atom substituted by a group chosen among 17-alkyl-alpha, 17-alkyl-beta, 17-OR₂-alpha and 17-OR₂-beta, where R₂ can be chosen among an allyl, a propargyl, a glycol, a PEG, a glycol-allyl, a PEG-allyl, and E can be a methylene group or a carbon atom substituted by a group chosen among 16-alkyl-alpha, 16-alkyl-beta, 16-OR₂-alpha and 16-OR₂-beta, where the R₂ can be chosen among an allyl, a propargyl, a glycol, a PEG, a glycol-allyl, a PEG-allyl; or E and F are involved in an epoxy cycle or a cyclopropyl and can be chosen among 16,17-epoxy-alpha, 16,17-epoxy-beta, 16,17-methylene-alpha and 16,17-methylene-beta; or E and F can be carbon atoms forming a 16,17-double bond; and G can be a carbonyl, a methylene or a carbon atom substituted by a 12-OR₃ alpha or 12-OR₃ beta group, where R₃ can be a H atom or a group chosen among the following: acetyl, alkyl and aryl groups, In some aspects, R₃ can be chosen among ci-c6-alkyl, benzyl, p-methoxybenzyl, benzoyl, tigloyl, angeloyl, 2,2,2-trichloroethoxycarbonyl, o-aminobenzoyl, nicotinoyl, 2-methylbutyryl, isovaleryl, cinnamoyl, coumaroyl, o-hydroxybenzoyl and anthraniloyl.

In some aspects, the neurosteroid or analogue or derivative thereof can be according to Formula (I), where R₁ is a group chosen among the 3-beta O-allyl, 3-beta O-propargyl, 3-beta O-glycol, 3-beta O-PEG, 3-beta O-glycol-allyl and 3-beta O-PEG-allyl groups and/or G is a methylene.

In some aspects, the neurosteroid or analogue or derivative thereof can be Compound Allo (1).

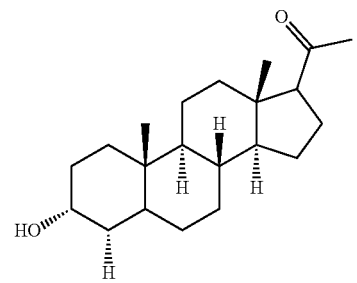

(1)

In some aspects, the neurosteroid or analogue or derivative thereof can be Compound BR053.

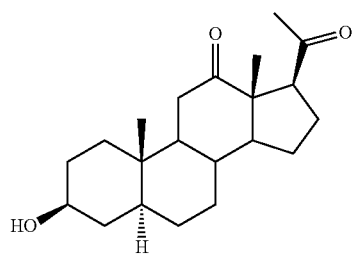

BR053

In some aspects, the neurosteroid or analogue or derivative thereof can be Compound BR338.

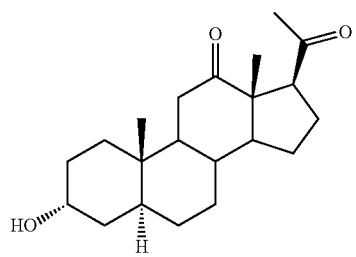

BR338

In some aspects, the neurosteroid or analogue or derivative thereof can be Compound BR297.

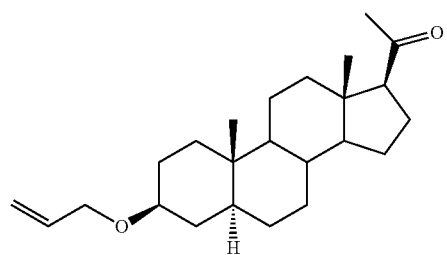

BR297

In some aspects, the neurosteroid or analogue or derivative thereof can be Compound BR351.

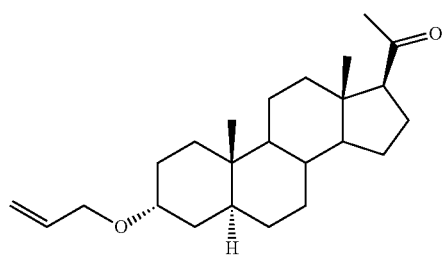

BR351

In some aspects, the neurosteroid or analogue or derivative thereof can be Compound (2).

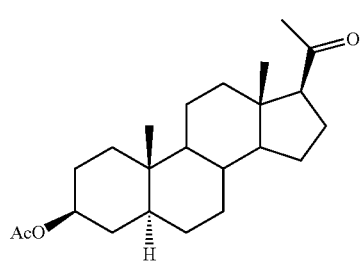

(2)

In some aspects, the neurosteroid or analogue or derivative thereof can be Compound (3).

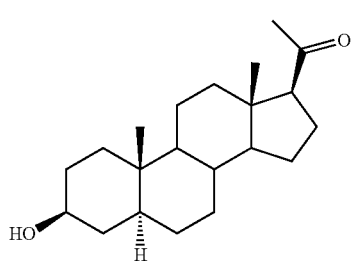

(3)

In some aspects, the neurosteroid or analogue or derivative thereof can be Compound (4).

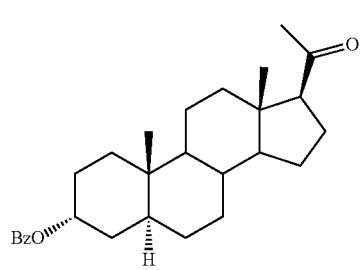

(4)

In some aspects, the neurosteroid or analogue or derivative thereof can be Compound (5).

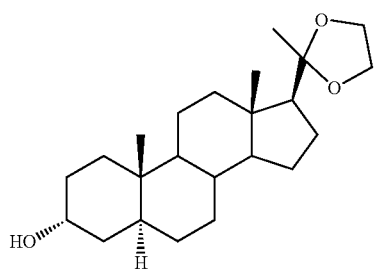

(5)

In some aspects, the neurosteroid or analogue or derivative thereof can be Compound (6).

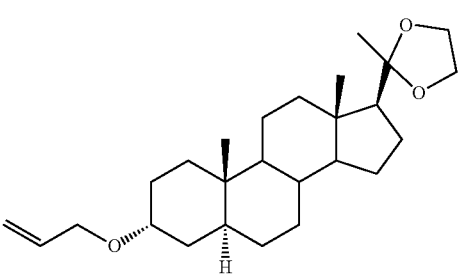

(6)

In some aspects, the neurosteroid or analogue or derivative thereof can be Compound (7).

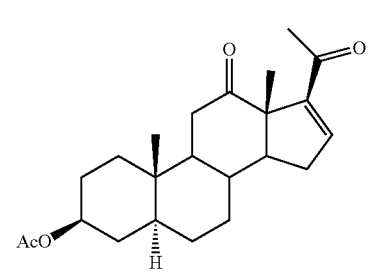

(7)

In some aspects, the neurosteroid or analogue or derivative thereof can be Compound (8).

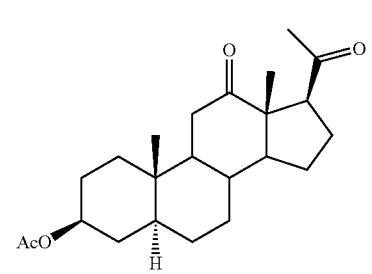

(8)

In some aspects, the neurosteroid or analogue or derivative thereof can be Compound (9).

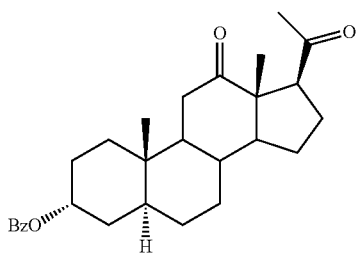

(9)

Synthesis of the neurosteroid(s) and analogue(s) or derivative(s) thereof can be as described in U.S. Pat. Pub. 2014/0058079, which is incorporated by reference as if expressed in its entirety herein.

The neruosteroid(s) and analogue(s) and/or derivative(s) thereof described herein can be included in a pharmaceutical formulation that, in addition to the compound, can further include a pharmaceutically acceptable carrier. The formulation can be a pharmaceutical formulation. The neruosteroid(s) and analogue(s) and/or derivative(s) thereof described herein can be administered to a subject in need thereof. The subject in need thereof can have, be suspected of having, and/or be at risk for developing a neuropsychiatric disorder. Neuropsychiatric disorders include, but are not limited to addiction, developmental conditions (e.g. attention deficit hyperactivity disorder (ADHD), autism, fetal alcohol syndrome, and tic disorders), eating disorders, degenerative disease (e.g. dementia, Parkinson's disease, and Alzheimer's disease; amyotrophic lateral sclerosis (ALS), multiple sclerosis), mood/affect disorders (e.g. bipolar disorder, depressions, premenstrual syndrome, impulsivity, aggressiveness, and mania, anxiety spectrum disorders), neurotic disorders (e.g. obsessive compulsive disorder, trichotillomania, and anxiety disorders)), post-traumatic stress disorder (PTSD), psychosis (e.g. schizophrenia), and sleep disorders (e.g. sleep apnea, narcolepsy, insomnia, and parasomnia), epilepsy, suicide, traumatic brain injury (TBI), chronic pain, alcohol and other substance addiction.

In some aspects, the neuropsychiatric disorder can be an anxiety and/or depression disorder. In some aspects, the neuropsychiatric disorder can be an anxiety disorder. In some aspects, the neuropsychiatric disorder can be PTSD. In some aspects, the neuropsychiatric disorder can be a depression disorder. In some aspects, the depression disorder can be MDD. The compounds and formulations described herein can be administered by a suitable route, such as but not limited to oral, infusion, epidural, subarachnoid, intracerebroventricular, and intravenous. Other suitable routes are described elsewhere herein.

The neurosteriods, analogues thereof, and derivatives of the neurosteroids or analogues thereof can be used in the manufacture of a medicament for treatment of a neuropsychiatric disorder, including but not limited to PTSD and/or MDD.

Parenteral Formulations

The neruosteroid(s) and analogue(s) and/or derivative(s) thereof described herein can be formulated for parenteral delivery, such as injection or infusion, in the form of a solution or suspension. The formulation can be administered via any route, such as, the blood stream or directly to the organ or tissue to be treated.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the neruosteroid(s) and/or analogue(s) thereof described herein can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants can be anionic, cationic, amphoteric or nonionic surface active agents. Suitable anionic surfactants include, but are not limited to, those containing carboxylate, sulfonate and sulfate ions. Suitable anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Suitable cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Suitable nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation can also contain an antioxidant to prevent degradation of the self-assembling cyclopeptide-dye compound(s).

The formulation can be buffered to a pH of 3-8 for parenteral administration upon reconstitution. Suitable buffers include, but are not limited to, phosphate buffers, acetate buffers, and citrate buffers.

Water-soluble polymers can be used in the formulations for parenteral administration. Suitable water-soluble polymers include, but are not limited to, polyvinylpyrrolidone, dextran, carboxymethylcellulose, and polyethylene glycol. Sterile injectable solutions can be prepared by incorporating the neruosteroid(s) and/or analogue(s) thereof in the desired amount in the appropriate solvent or dispersion medium with one or more of the excipients listed above, as required, followed by filtered sterilization. Dispersions can be prepared by incorporating the various sterilized neruosteroid(s) and/or analogue(s) thereof into a sterile vehicle which contains the basic dispersion medium and the required other ingredients from those listed above. Sterile powders for the preparation of sterile injectable solutions can be prepared by vacuum-drying and freeze-drying techniques, which yields a powder of the neruosteroid(s) and/or analogue(s) thereof with or without any additional desired ingredient from a previously sterile-filtered solution thereof. The powders can be prepared in such a manner that the particles are porous in nature, which can increase dissolution of the particles. Methods for making porous particles are well known in the art.

Pharmaceutical formulations for parenteral administration can be in the form of a sterile aqueous solution or suspension of the neruosteroid(s) and analogue(s) and/or derivative(s) thereof. Acceptable solvents include, for example, water, Ringer's solution, phosphate buffered saline (PBS), and isotonic sodium chloride solution. The formulation can also be a sterile solution, suspension, or emulsion in a nontoxic, parenterally acceptable diluent or solvent such as 1,3-butanediol.

In some instances, the formulation can be distributed or packaged in a liquid form. In other aspects, formulations for parenteral administration can be packed as a solid, obtained, for example by lyophilization of a suitable liquid formulation. The solid can be reconstituted with an appropriate carrier or diluent prior to administration.

Solutions, suspensions, or emulsions for parenteral administration can be buffered with an effective amount of buffer necessary to maintain a pH suitable for ocular administration. Suitable buffers include, but are not limited to, acetate, borate, carbonate, citrate, and phosphate buffers.

Solutions, suspensions, or emulsions for parenteral administration can also contain one or more tonicity agents to adjust the isotonic range of the formulation. Suitable tonicity agents include, but are not limited to, glycerin, mannitol, sorbitol, sodium chloride, and other electrolytes.

Solutions, suspensions, or emulsions for parenteral administration can also contain one or more preservatives to prevent bacterial contamination of the ophthalmic preparations. Suitable preservatives include, but are not limited to, polyhexamethylenebiguanidine (PHMB), benzalkonium chloride (BAK), stabilized oxychloro complexes (otherwise known as Purite®), phenylmercuric acetate, chlorobutanol, sorbic acid, chlorhexidine, benzyl alcohol, parabens, thimerosal, and mixtures thereof.

Solutions, suspensions, or emulsions, including nanoformulations for parenteral administration can also contain one or more excipients, such as dispersing agents, wetting agents, and suspending agents.

Topical Formulations

The neruosteroid(s) and/or analogue(s) and/or derivative(s) thereof can be formulated for topical administration. Suitable dosage forms for topical administration include creams, ointments, salves, sprays, gels, lotions, emulsions, liquids, and transdermal patches. The formulation can be formulated for transmucosal, transepithelial, transendothelial, or transdermal administration. The topical formulations can contain one or more chemical penetration enhancers, membrane permeability agents, membrane transport agents, emollients, surfactants, stabilizers, and combination thereof.

In some aspects, neruosteroid(s) and/or analogue(s) and/or derivative(s) thereof can be administered as a liquid formulation, such as a solution or suspension, a semi-solid formulation, such as a lotion or ointment, or a solid formulation. The neruosteroid(s) and/or analogue(s) and/or derivative(s) thereof can be formulated as liquids, including solutions and suspensions, such as eye drops or as a semi-solid formulation, such as ointment or lotion for topical application to the skin, to the mucosa, such as the eye, to the vagina, or to the rectum.

The formulation can contain one or more excipients, such as emollients, surfactants, emulsifiers, penetration enhancers, and the like.

Suitable emollients include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In some aspects, the emollients can be ethylhexylstearate and ethylhexyl palmitate.

Suitable surfactants include, but are not limited to, emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In some aspects, the surfactant can be stearyl alcohol.

Suitable emulsifiers include, but are not limited to, acacia, metallic soaps, certain animal and vegetable oils, and various polar compounds, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxpropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In some aspects, the emulsifier can be glycerol stearate.

Suitable classes of penetration enhancers include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocylic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols).

Suitable emulsions include, but are not limited to, oil-in-water and water-in-oil emulsions. Either or both phases of the emulsions can include a surfactant, an emulsifying agent, and/or a liquid non-volatile non-aqueous material. The surfactant can be a non-ionic surfactant. The emulsifying agent can be an emulsifying wax. In further aspects, the liquid non-volatile non-aqueous material is a glycol. In some aspects, the glycol is propylene glycol. The oil phase can contain other suitable oily pharmaceutically acceptable excipients. Suitable oily pharmaceutically acceptable excipients include, but are not limited to, hydroxylated castor oil or sesame oil can be used in the oil phase as surfactants or emulsifiers.

Lotions containing the neruosteroid(s) and/or analogue(s) thereof are also described herein. The lotion can be in the form of an emulsion having a viscosity of between 100 and 1000 centistokes. The fluidity of lotions can permit rapid and uniform application over a wide surface area. Lotions can be formulated to dry on the skin leaving a thin coat of their medicinal components on the skin's surface.

Creams containing the neruosteroid(s) and/or analogue(s) and/or derivative(s) thereof are also described herein. The cream can contain emulsifying agents and/or other stabilizing agents. The cream can be in the form of a cream having a viscosity of greater than 1000 centistokes, typically in the range of 20,000-50,000 centistokes. Creams, as compared to ointments, can be easier to spread and easier to remove.

One difference between a cream and a lotion is the viscosity, which is dependent on the amount/use of various oils and the percentage of water used to prepare the formulations. Creams can be thicker than lotions, can have various uses, and can have more varied oils/butters, depending upon the desired effect upon the skin. In some aspects of a cream formulation, the water-base percentage can be about 60% to about 75% and the oil-base can be about 20% to about 30% of the total, with the other percentages being the emulsifier agent, preservatives and additives for a total of 100%.

Ointments containing the neruosteroid(s) and/or analogue(s) and/or derivative(s) thereof and a suitable ointment base are also provided. Suitable ointment bases can include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

Also described herein are gels that can contain the neruosteroid(s) and/or analogue(s) and/or derivative(s) thereof, a gelling agent, and a liquid vehicle. Suitable gelling agents include, but are not limited to, modified celluloses, such as hydroxypropyl cellulose and hydroxyethyl cellulose; carbopol homopolymers and copolymers; thermoreversible gels and combinations thereof. Suitable solvents in the liquid vehicle can include, but are not limited to, diglycol monoethyl ether; alklene glycols, such as propylene glycol; dimethyl isosorbide; alcohols, such as isopropyl alcohol and ethanol. The solvents can be selected for their ability to dissolve the drug. Other additives, which can improve the skin feel and/or emolliency of the formulation, can also be incorporated. Such additives include, but are not limited, isopropyl myristate, ethyl acetate, $C_{12}$-$C_{15}$ alkyl benzoates, mineral oil, squalane, cyclomethicone, capric/caprylic triglycerides, and combinations thereof.

Also described herein are foams that can include the neruosteroid(s) and/or analogue(s) and/or derivative(s) thereof. Foams can be an emulsion in combination with a gaseous propellant. The gaseous propellant can include hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or can become approved for medical use are suitable. The propellants can be devoid of hydrocarbon propellant gases, which can produce flammable or explosive vapors during spraying. Furthermore, the foams can contain no volatile alcohols, which can produce flammable or explosive vapors during use.

Buffers can be used to control pH of a composition. The buffers can buffer the composition from a pH of about 4 to a pH of about 7.5, from a pH of about 4 to a pH of about 7, or from a pH of about 5 to a pH of about 7. In some aspects, the buffer can be triethanolamine.

Preservatives can be included to prevent the growth of fungi and microorganisms. Suitable preservatives can include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

The formulations can be provided via continuous delivery of one or more formulations to a subject in need thereof. For topical applications, repeated application can be done or a patch can be used to provide continuous administration of the noscapine analogs over an extended period of time.

Enteral Formulations

The neruosteroid(s) and/or analogue(s) and/or derivative(s) thereof can be prepared in enteral formulations, such as for oral administration. Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Formulations containing the neruosteroid(s) and/or analogue(s) and/or derivative(s) thereof can be prepared using pharmaceutically acceptable carriers. As generally used herein "carrier" includes, but is not limited to, diluents, preservatives, binders, lubricants, disintegrators, swelling agents, fillers, stabilizers, and combinations thereof. Polymers used in the dosage form include, but are not limited to, suitable hydrophobic or hydrophilic polymers and suitable pH dependent or independent polymers. Suitable hydrophobic and hydrophilic polymers include, but are not limited to, hydroxypropyl methylcellulose, hydroxypropyl cellulose, hydroxyethyl cellulose, carboxy methylcellulose, polyethylene glycol, ethylcellulose, microcrystalline cellulose, polyvinyl pyrrolidone, polyvinyl alcohol, polyvinyl acetate, and ion exchange resins. "Carrier" can also include all components of the coating composition which can include plasticizers, pigments, colorants, stabilizing agents, and glidants.

Formulations containing the neruosteroid(s) and/or analogue(s) and/or derivative(s) thereof can be prepared using one or more pharmaceutically acceptable excipients, including diluents, preservatives, binders, lubricants, disintegrators, swelling agents, fillers, stabilizers, and combinations thereof.

Delayed release dosage formulations containing the neruosteroid(s) and/or analogue(s) and/or derivative(s) thereof can be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment and process for preparing tablets and capsules and delayed release dosage forms of tablets, capsules, and granules. These references provide information on carriers, materials, equipment and process for preparing tablets and capsules and delayed release dosage forms of tablets, capsules, and granules.

The formulations containing the neruosteroid(s) and/or analogue(s) and/or derivative(s) thereof can be coated with a suitable coating material, for example, to delay release once the particles have passed through the acidic environment of the stomach. Suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings can be formed with a different ratio of water soluble polymer, water insoluble polymers and/or pH dependent polymers, with or without water insoluble/water soluble non polymeric excipient, to produce the desired release profile. The coating can be performed on a dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Additionally, the coating material can contain conventional carriers such as plasticizers, pigments, colorants, glidants, stabilization agents, pore formers and surfactants. Optional pharmaceutically acceptable excipients include, but are not limited to, diluents, binders, lubricants, disintegrants, colorants, stabilizers, and surfactants.

Diluents, also referred to as "fillers," can be used to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful.

Binders can impart cohesive qualities to a solid dosage formulation, and thus can ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders.

Lubricants can be included to facilitate tablet manufacture. Suitable lubricants include, but are not limited to, magnesium stearate, calcium stearate, stearic acid, glycerol behenate, polyethylene glycol, talc, and mineral oil. A lubricant can be included in a tablet formulation to prevent the tablet and punches from sticking in the die. The lubricant can be chosen from such slippery solids as talc, magnesium and calcium stearate, stearic acid and hydrogenated vegetable oils.

Disintegrants can be used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

Stabilizers can be used to inhibit or retard drug decomposition reactions which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

Kits Containing a Neruosteroid, Analogue(s) Thereof, or Pharmaceutical Formulation Thereof The neruosteroid(s) and/or analogue(s) and/or derivative(s) thereof, and/or pharmaceutical formulations thereof described herein can be presented as a combination kit. As used herein, the terms "combination kit" or "kit of parts" refers to the compounds, or pharmaceutical formulations and additional components that are used to package, sell, market, deliver, and/or administer the combination of elements or a single element, such as the active ingredient, contained therein. Such additional components include, but are not limited to, packaging, syringes, blister packages, bottles, and the like. When one or more of the components (e.g. active agents) contained in the kit are administered simultaneously, the combination kit can contain the active agents in a single pharmaceutical formulation (e.g. a tablet) or in separate pharmaceutical formulations. When one or more of the active agents are not administered simultaneously, the combination kit can contain each active agent in separate pharmaceutical formulations. The separate pharmaceutical formulations can be contained in a single package or in separate packages within the kit.

The kit can also include instructions printed on or otherwise contained in a tangible medium of expression. Instructions can be incorporated in labels, boxes, containers, syringes, delivery devices, insert sheets of paper, flash drives, CD-ROM, an internet website and the like. The instructions can provide information regarding the content of the compound or pharmaceutical formulations contained therein, safety information regarding the content of the compound(s) or pharmaceutical formulation(s) contained therein, information regarding the dosages, indications for use, and/or recommended treatment regimen(s) for the compound(s) and/or pharmaceutical formulations contained therein. In some aspects, the instructions provide directions for administering the compounds, compositions, pharmaceutical formulations, or salts thereof to a subject having, suspected of having, or predisposed to or at risk of developing a deuropsychiatric disorder including, but not limited to addiction, developmental conditions (e.g. attention deficit hyperactivity disorder (ADHD), autism, fetal alcohol syndrome, and tic disorders), eating disorders, degenerative disease (e.g. dementia, Parkinson's disease, and Alzheimer's disease; amyotrophic lateral sclerosis (ALS), multiple sclerosis), mood/affect disorders (e.g. bipolar disorder, depressions, premenstrual syndrome, impulsivity, aggressiveness, and mania, anxiety spectrum disorders), neurotic disorders (e.g. obsessive compulsive disorder, trichotillomania, and anxiety disorders)), post-traumatic stress disorder (PTSD), psychosis (e.g. schizophrenia), and sleep disorders (e.g. sleep apnea, narcolepsy, insomnia, and parasomnia), epilepsy, suicide, traumatic brain injury (TBI), chronic pain, alcohol and other substance addiction.

The instructions can provide directions for administering the neruosteroid(s) and/or analogue(s) thereof and/or pharmaceutical formulations thereof to a subject having, suspected of having, or predisposed to developing PTSD and/or MDD. The instructions can provide directions administering the neruosteroid(s) and/or analogue(s) and/or derivative(s) thereof and/or pharmaceutical formulations thereof to a subject in need thereof that is a non-responder to conventional neuropsychiatric therapies, including conventional pharmacological intervention including but not limited to benzodiazepines and/or SSRI's.

The instructions can provide directions for administering compounds, compositions, pharmaceutical formulations, or salts thereof to a subject having lower Allo levels in the brain, saliva, and/or CSF, as compared to a normal control and/or healthy subject. The instructions can provide directions for administering the neruosteroid(s) and/or analogue(s) thereof and/or pharmaceutical formulations thereof to a subject in need thereof when the subject in need thereof expresses a biomarker for a neuropsychiatric disorder (see e.g. Table 1). The instructions can provide directions for administering the neruosteroid(s) and/or analogue(s) thereof and/or pharmaceutical formulations thereof to a subject in need thereof when the subject in need thereof expresses a biomarker for PTSD and/or MDD (see e.g. Table 1).

Methods of Treating Neuropsychiatric Disorders Using a Neruosteroid and/or Analogue(s) Thereof or Pharmaceutical Formulation Thereof Also described herein are methods of treating a neuropsychiatric disorder in a subject in need thereof. The neruosteroid(s) and/or analogue(s) thereof and/or pharmaceutical formulation(s) thereof can be administered to a subject in need thereof. In some aspects the subject in need thereof can have, be suspected of having, and/or be predisposed to and/or at risk of developing a neuropsychiatric disorder. Neuropsychiatric disorders include, but are not limited to addiction, developmental conditions (e.g. attention deficit hyperactivity disorder (ADHD), autism, fetal alcohol syndrome, and tic disorders), eating disorders, degenerative disease (e.g. dementia, Parkinson's disease, and Alzheimer's disease; amyotrophic lateral sclerosis (ALS), multiple sclerosis), mood/affect disorders (e.g. bipolar disorder, depressions, premenstrual syndrome, impulsivity, aggressiveness, and mania, anxiety spectrum disorders), neurotic disorders (e.g. obsessive compulsive disorder, trichotillomania, and anxiety disorders)), post-traumatic stress disorder (PTSD), psychosis (e.g. schizophrenia), and sleep disorders (e.g. sleep apnea, narcolepsy, insomnia, and parasomnia), epilepsy, suicide, traumatic brain injury (TBI), chronic pain, alcohol and other substance addiction.

In some aspects, the neuropsychiatric disorder is characterized by low Allo levels, such as in the brain, CSF, blood, or other tissue or fluid sample. In some aspects the subject in need thereof is a non-responder to conventional therapies, including conventional pharmacological intervention including, but not limited to, benzodiazepines and/or SSRI's. In some aspects, the neuropsychiatric disorder can be PTSD and/or MDD. In some aspects, one or more of the biomarkers shown in Table 1 can be measured and detected in the subject in need thereof. Suitable methods for measuring or detecting a biomarker for a neuropsychiatric disorder can be PCR techniques, immunodetection techniques (e.g. ELISA, western blotting, ChiP, and immunohistochemistry), mass spectrometry, gas chromatography and other chromatography techniques (e.g. high performance liquid chromatography, other size exclusion chromatography techniques, other ion exchange chromatography techniques, affinity chromatography techniques, and other gel filtration chromatography techniques).

TABLE 1

Biomarkers for Neuropsychiatric Disorders

| Biomarker | Example Neuropsychiatric Disorders or symptom thereof | Reference |
| --- | --- | --- |
| polymorphisms in the dopamine D2 receptor gene (DRD2 gene) 957C > T | PTSD | Example 2, Voisey et al. Depress Anxiety. 2009; 26(1): 28-33 |
| polymorphism in the 5α-reductase type 2 | PTSD, depression | Example 2, Hellgren et al. Hormones and Behavior. 2017; 94: 106-113 |
| decreased expression of the FKB5 gene | PTSD, depression | Example 2, Menke et al. Neuropsychopharmacology. 2012. 37(6): 1455-64 |
| methylation status of the FKB5 gene | PTSD | See Example 2 |
| increased cortisol | PTSD | See Example 2 |
| increased methylation of exon 1 of the glucocorticoid receptor gene (leukocytes and hippocampus | PTSD | See Example 2 |
| methylation status of NPY | PTSD | See Example 2 |
| methylation status of brain-derived neurotropic factor (BDNF) | PTSD | See Example 2 |

TABLE 1-continued

Biomarkers for Neuropsychiatric Disorders

| Biomarker | Example Neuropsychiatric Disorders or symptom thereof | Reference |
| --- | --- | --- |
| methylation status of α-MSH | PTSD | See Example 2 |
| methylation status of enzymes involved in biosynthesis of neurohormones (e.g. GABAergic steroids) | PTSD | See Example 2 |
| increased C-reactive protein | PTSD, depression | See Example 2 |
| increased IL-6 (serum) | PTSD, a treatment (e.g. SSRI) non-responder | See Example 2 |
| decreased BNDF expression serum and brain (e.g. hippocampus) | PTSD, depression, can be indicative of effective response to treatment of SSRI | See Example 2 |
| decreased TrkB (BDNF receptor) | PTSD, depression | See Example 2 |
| polymorphisms in BDNF gene (rs6265 Val66Met substitution and others) | PTSD, affect disorders, depression | See Example 3 |
| decreased NPY (CSF and plasma) | PTSD | See Example 2 |
| SNP in NPY gene (rs16147) | PTSD, depression | See Example 2 |
| Decreased neurosteroids Allo and pregnanolone) (serum, plasma, CSF, brain) | PTSD, depression | See Example 2 |
| decreased 5α-reductase type 1 | PTSD, depression | Example 2 |
| SNP in 5α-reductase type 1 gene | PTSD, depression | Example 2 |
| Increased level of dehydroepiandrosterone (DHEA) and sulfate derivatives | PTSD | Example 2 |
| ratio of DHEA to Allo | PTSD | Example 2 |
| increased $GABA_A$ receptor subunits α4, α5, and δ | PTSD | See Examples 2 and 3 |
| reduced $GABA_A$ receptor subunits α1, α2, and γ2 | PTSD | See Example 3 |
| increased sensitivity for neurosteroids | PTSD | See Example 3 |
| failure to bind benzodiazepines and no clinical response to benzodiazepines | PTSD | See Examples 2 and 3 |
| increased cannabinoid receptor 1 ($CB_1$) | PTSD | See Example 2 |
| decreased serum AEA and 2-arachidonoylglycerol (2-AG) | PTSD, depression | See Example 2 |
| decreased PEA and OEA | PTSD, depression | See Example 2 |
| polymorphism in 5-HTT gene | depression | See Example 2 |
| SNP in the CRHR1 gene: 110402, patients homozygous for the TT allele | Major depressive disorder (MDD) | See Example 2 |
| increased corticotrophin releasing hormone in CSF | depression | See Example 2 |
| increased adrenocorticotrophic hormone | depression | See Example 2 |
| increased glucocorticoid synthesis | depression | See Example 2 |
| increased cortisol (saliva, urine, plasma) | PTSD, depression | See Example 2 |
| decreased sensitivity as determined by response to dexamethasone by the glucocorticoid receptor | depression | See Example 2 |
| polymorphisms in the FKB5 genes rs1360780 | depression | See Example 2 |
| increased tumor necrosis factor alpha (TNF-α) | Depression, PTSD, also can indicate an SSRI non-responder | See Example 2 |
| increased IL-1 | depression | See Example 2 |
| increased IL-6 | Depression, can also indicate an SSRI non-responder | See Example 2 |

TABLE 1-continued

Biomarkers for Neuropsychiatric Disorders

| Biomarker | Example Neuropsychiatric Disorders or symptom thereof | Reference |
| --- | --- | --- |
| Increased IL-1β | depression | See Example 2 |
| SNPs in IL-1β gene: rs16944, rs1143643 | Depression, also can be indicative of subjects non-responsive to anti-depressants | See Example 2 |
| IL-6 SNP rs 1800795 | depression | See Example 2 |
| decreased 3α-hydroxisteroid dehydrogenesis | Depression, PTSD | See Example 2 |
| SNPs cannabinoid receptor 1 (CB$_1$) | Depression | See Example 2 |

The method can include administering an amount of the neruosteroid(s) and/or analogue(s) and/or derivative(s) thereof and/or pharmaceutical formulation(s) the subject in need thereof. The amount can be an effective amount. As described above, the subject in need thereof can have, be suspected of having, be predisposed to, and/or at risk for developing a neuropsychiatric disorder. The effective amount can reduce or eliminate a symptom of a neuropsychiatric disorder. In some aspects, the effective amount can reduce or eliminate a symptom of PTSD and/or MDD in a subject in need thereof.

The neruosteroid(s) and/or analogue(s) and/or derivative(s) thereof and/or pharmaceutical formulation(s) can be co-administered or be a co-therapy as part of a treatment regimen with another active agent or ingredient that can be included in the formulation or provided in a dosage form separate from the n neruosteroid(s) and/or analogue(s) and/or derivative(s) thereof and/or pharmaceutical formulation(s) thereof. Other active agents or ingredients can include SSRI's (e.g. citalopram, escitalopram, fluoxetine, paroxetine, sertraline, and vilazodone). In some aspects, the SSRI's can be administered at low non-serotonergic doses and thus can act as selective brain steroidogenic stimulants. In some aspects, other active agents or ingredients can include a PPARα agonist. PPARα agonists can include, but are not limited to, endocannabinoids (e.g. AEA, PEA, and oleoyldopamine (OEA), stearoylethanolamide (SEA), 2-arachidonoylglycerol (2-AG)), fibrate compounds (e.g. clofibrate, gemfibrozil, ciprofibrate, bezafibrate, and fenofibrate), GW7647, GW6471, dual PPAR agonists (act at PPARα and γ: e.g. aleglitazar, muraglitazar, farglitazar, saroglitazar, chiglitazar and tesaglitazar) (act at PPARα and δ: e.g. GFT505), pan PPAR agonists (e.g. IVA337); phytol, and prinixic acid. The neruosteroid(s) and/or analogue(s) thereof and/or pharmaceutical formulation(s) can be included in a treatment regimen that includes psychotherapy.

The amount of the neruosteroid(s) and/or analogue(s) and/or derivative(s) thereof and/or pharmaceutical formulation(s) thereof administered can range from about 0.1 µg/kg to up to about 1000 mg/kg or more, depending on the factors mentioned elsewhere herein. In certain aspects, the amount can range from 0.1 µg/kg up to about 500 mg/kg, or 1 µg/kg up to about 500 mg/kg, 5 µg/kg up to about 500 mg/kg, 0.1 µg/kg up to about 100 mg/kg, or 1 µg/kg up to about 100 mg/kg, 5 µg/kg up to about 100 mg/kg.

In some aspects, the amount can range from about 1 mg/kg to about 5 mg/kg. In some aspects, the compound administered can be BR351 and the amount administered can range from about 1 mg/kg to about 5 mg/kg. The amount can range from about 0.325 mg/kg to about 2.5 mg/kg. In some aspects, the compound can be BR297 and the amount administered can range from about 0.325 mg/kg to about 2.5 mg/kg. The amount can range from about 5 mg/kg to about 15 mg/kg. In some aspects, the compound can be ganaxolone and the amount administered can range from about 5 mg/kg to about 15 mg/kg. In some aspects, the compound can be ganaxolone and the amount administered can be about 10 mg/kg.

In some aspects, the effective amount can range from about 1 mg/kg to about 5 mg/kg. In some aspects, the compound administered can be BR351 and the effective amount administered can range from about 1 mg/kg to about 5 mg/kg. The effective amount can range from about 0.325 mg/kg to about 2.5 mg/kg. In some aspects, the compound can be BR297 and the effective amount administered can range from about 0.325 mg/kg to about 2.5 mg/kg. The effective amount can range from about 5 mg/kg to about 15 mg/kg. In some aspects, the compound can be ganaxolone and the effective amount administered can range from about 5 mg/kg to about 15 mg/kg. In some aspects, the compound can be ganaxolone and the amount can be about 10 mg/kg.

Administration of the neruosteroid(s) and/or analogue(s) and/or derivative(s) thereof and/or pharmaceutical formulation(s) can be systemic or localized. The neruosteroid(s) and/or analogue(s) and/or derivative(s) thereof and/or pharmaceutical formulation(s) thereof can be administered to the subject in need thereof one or more times per hour or day. The neruosteroid(s) and/or analogue(s) and/or derivative(s) thereof and/or pharmaceutical formulation(s) thereof can be administered once daily. The neruosteroid(s) and/or analogue(s) and/or derivative(s) thereof and/or pharmaceutical formulation(s) thereof can be administered can be administered 2, 3, 4, 5, 6, 7, 8, 9, 10, 11, 12, or more times daily. When administered, an effective amount of the neruosteroid(s) and/or analogue(s) and/or derivative(s) thereof and/or pharmaceutical formulation(s) thereof can be administered to the subject in need thereof. The neruosteroid(s) and/or analogue(s) and/or derivative(s) thereof and/or pharmaceutical formulation(s) thereof can be administered one or more times per week. The neruosteroid(s) and/or analogue(s) and/or derivative(s) thereof and/or pharmaceutical formulation(s) thereof can be administered 1, 2, 3, 4, 5, 6 or 7 days per week. The neruosteroid(s) and/or analogue(s) and/or derivative(s) thereof and/or pharmaceutical formulation(s) thereof can be administered 1, 2, 3, 4, 5, 6, 7, 8, 9, 10, 11, 12, or more times per month. The neruosteroid(s) and/or analogue(s) and/or derivative(s) thereof and/or pharmaceutical formulation(s)

thereof can be administered 1, 2, 3, 4, 5, 6, 7, 8, 9, 10, 11, 12, 13, 14, 15, 16, 17, 18, or more time per year.

The neruosteroid(s) and/or analogue(s) and/or derivative(s) thereof and/or pharmaceutical formulation(s) thereof can be administered in a dosage form. The amount or effective amount of the neruosteroid(s) and/or analogue(s) and/or derivative(s) thereof and/or pharmaceutical formulation(s) thereof can be divided into multiple dosage forms. For example, the amount or effective amount can be split into two dosage forms and the one dosage forms can be administered, for example, in the morning, and the second dosage form can be administered in the evening. Although the amount can be given over two or more doses, in one day, the subject can receives the desired amount or effective amount when the total amount administered across all the doses is considered. The dosages can range from about 0.1 µg/kg to up to about 1000 mg/kg or more, depending on the factors mentioned above. In certain aspects, the dosage can range from 0.1 µg/kg up to about 500 mg/kg, or 1 µg/kg up to about 500 mg/kg, 5 µg/kg up to about 500 mg/kg, 0.1 µg/kg up to about 100 mg/kg, or 1 µg/kg up to about 100 mg/kg, 5 µg/kg up to about 100 mg/kg.

In some aspects, the dosage can range from about 1 mg/kg to about 5 mg/kg. In some aspects, the compound administered can be BR351 and the dosage can range from about 1 mg/kg to about 5 mg/kg. The dosage can range from about 0.325 mg/kg to about 2.5 mg/kg. In some aspects, the compound can be BR297 and the dosage can range from about 0.325 mg/kg to about 2.5 mg/kg. The dosage can range from about 5 mg/kg to about 15 mg/kg. In some aspects, the compound can be ganaxolone and the dosage can range from about 5 mg/kg to about 15 mg/kg. In some aspects, the compound can be ganaxolone and the dosage can be about 10 mg/kg.

In some aspects, the method can also include the step of measuring one or more biomarkers for a neuropsychiatric disorder. In some aspects the biomarker can be a biomarker shown in Table 1.

EXAMPLES

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of aspects of the present disclosure.

Example 1

Introduction:

Exposure to traumatic experiences is associated with a drastic increase in the risk of developing psychiatric disorders, including major depressive disorder (MDD) and post-traumatic stress disorder (PTSD). These debilitating conditions affect 8-16% of adult population in the United States and MDD alone is the most common neuropsychiatric disease worldwide (Kessler et al., 2005; Berton and Nestler, 2006; Whiteford et al., 2013).

Severe traumas, including abuse in women, child abuse and neglect, combat situations or sexual assault, result in a particularly serious form of chronic PTSD that is often comorbid with MDD and suicide (Prigerson et al., 2001), and is associated with a marked increase in vulnerability to substance and alcohol abuse as well as mood disorders such as bipolar disorder, generalized anxiety, and phobias (Famularo et al., 1992; Agid et al., 1999; Heim and Nemeroff, 2001; Kendler et al., 2004). Furthermore, a history of early-life trauma can predict a more severe and chronic depression and inadequate response to both pharmacological and psychotherapeutic treatments and even failure of treatment response in adulthood (Kessler, 1997; Zlotnick et al., 1997; Lanquillon et al., 2000; Wiersma et al., 2009; Shamseddeen et al., 2011; Nanni et al., 2012). For example, multiple childhood adverse experiences increased fourfold the risk of developing MDD during adult life (Felitti et al., 1998), and increased 2-5 times the risk of attempted suicide in childhood, adolescence, and adulthood (Dube et al., 2001). A study in women demonstrated a tight correlation between sexual or physical abuse in childhood and increased symptoms of anxiety, MDD, addiction and suicide in adulthood (McCauley et al., 1997). Of note, abuse in general but most notably, abuse occurring between 4 and 7 years of age predicted a lower response to 8 weeks of selective serotonin reuptake inhibitors (SSRIs) (Williams et al., 2016). SSRIs remain the most used antidepressants for decades, however, only 40-50% of MDD patients achieve remission, and more than ⅓ develop pharmacoresistance (Golden et al., 2002; Rush et al., 2006; Kemp et al., 2008). Likewise, for PTSD treatment, the only drugs approved by the FDA are the SSRIs sertraline and paroxetine but only 20% of SSRI-treated PTSD patients do not relapse (Westenberg, 1996; Walderhaug et al., 2010; Ipser and Stein, 2012). The reasons underlying SSRI-resistance can be multiple and can be found in genetic factors, pharmacokinetics, type of trauma, and comorbidity with other mental disorders (El-Hage et al., 2013; Willner et al., 2013). Failure to achieve full remission from MDD and PTSD symptoms in a large portion of patients indicates the need to develop alternative drugs for the treatment of non-responders. Both MDD and PTSD are associated with altered GABAergic neurotransmission. For example, adolescent as well as adult MDD patients show a reduction of plasma, CSF, and cerebral cortex GABA concentrations (Luscher et al., 2011). Moreover, the expression of several GABAA receptor subunits is altered in brain areas of MDD patients (Merali et al., 2004; Choudary et al., 2005; Klempan et al., 2009; Sequeira et al., 2009; Fatemi et al., 2013). Male Dutch veterans affected by PTSD show a significant reduction of benzodiazepine binding in cortex, hippocampus, and hypothalamus (Geuze et al., 2008), while male Viet Nam veterans show reduced binding in prefrontal cortex, Broadmann area 9 (Bremner et al., 2000). Furthermore, MDD and PTSD patients show low plasma, CSF, and brain levels of the GABAA receptor-active, neurosteroid allopregnanolone (Allo) (Romeo et al., 1998; van Broekhoven and Verkes, 2003; Uzunova et al., 2006; Agis-Balboa et al., 2014). Depression during pregnancy and post-partum is likewise associated with changes in Allo levels (Nemeroff, 2008). Importantly, treatment with SSRIs normalizes CSF, plasma, and brain Allo levels in MDD patients, an effect associated with improved symptoms, while patients who fail to respond to SSRIs also fail to increase Allo levels (Romeo et al., 1998; Uzunova et al., 2006). Mouse stress models are probably the best translational approach to reproduce some of the behavioral and neurochemical alterations observed in MDD and PTSD patients. For example, the socially isolated (SI) mouse, a putative rodent model of PTSD, shows a time-dependent downregulation of corticolimbic Allo levels associated with behavioral dysfunction, such as aggressive behavior, anxiety like behavior and altered contextual fear responses (Dong et al., 2001; Pinna et al., 2003; Pibiri et al., 2008; Nin et al., 2011a; Locci and Pinna, 2017a; Rasmusson et al., 2017). Furthermore, SI mice show changes in the expression of several $GABA_A$ receptor subunits, which similar to PTSD patients, result in resistance to benzodiazepine's pharmacological effects (Pinna et al., 2006b; Geuze et al., 2008; Pibiri et al., 2008; Nin et al., 2011b). Intriguingly, administration of low doses of SSRIs, acting as selective brain steroidogenic stimulants (SBSSs), normalize brain Allo levels and improve behavior in SI mice (Pinna et al., 2003, 2009). Likewise, administration of the Allo analog, ganaxolone (GNX), results in a dose-dependent improvement of emotional behavior (Pinna and Rasmusson, 2014).

Without being bound by theory, it is thought that early (PND 21) adolescence social isolation contributes to a more rapid and severe development of aggression and a lower pharmacological response to S-fluoxetine (S-FLX) than mice isolated in late adolescence (PND 45), which can be demonstrated by (i) a lower reduction in the rate of aggression, (ii) a lower duration of the drugs effect, and (iii) a higher percent of "non-responders." The pharmacological effect of S-FLX with that of neurosteroid-based treatments, including Allo analogs, GNX, BR351, and BR297, which can directly act at $GABA_A$ receptors.

This Example can demonstrate that a single dose treatment with S-FLX, GNX, BR351, and/or BR297, which can act directly at $GABA_A$ receptors. These compounds in general was observed to induce a stronger reduction of aggressive behavior in late than in early adolescent SI mice. Moreover, the rate of non-responders for these compounds was higher in early SI mice and the pharmacological effect of these compounds was more enduring in late than early adolescent SI mice. These data can show that early SI mice develop earlier and more severe aggression than late SI mice and compounds GNX, BR351, and/or BR297 are stronger agents in counteracting these behavioral deficits.

Materials and Methods.

Animals.

Male Swiss-Webster mice (Harlan Breeders) (18-30 g body weight), maintained under a 12-h dark/light cycle with food and water ad libitum were used for all experiments. Mice were housed individually in a cage of dimensions 24 cm×17 cm×12 cm. For these experiments, two mice experimental groups were used for the study of drug effect in different age conditions. The first group was isolated at 21 days ("early adolescent SI mice," PND 21), while the second group at 45 days ("late adolescent SI mice," PND 45). The animals were exposed to behavioral testing after 6 weeks of isolation. The vivarium temperature was kept at 24° C. and the humidity near 65%.

Drug Treatments.

S-fluoxetine (S-FLX) (0.375-1.5 mg/kg) was obtained from Eli Lilly and Company (Indianapolis, Ind., United States). GNX (10 mg/kg; EC50 dose, previously established in Pinna and Rasmusson, 2014) was obtained from Marinus Pharmaceuticals, Inc. (Boston, Mass., United States). BR351 (1-5 mg/kg) and BR297 (0.3125-2.5 mg/kg) were obtained from NeuroRhine Consortium (Strasbourgh, France). All the drugs were dissolved in saline solution containing 0.5% Tween-80 (Sigma Aldrich, St. Louis, Mo., United States), and were injected intraperitoneally (i.p.), 60 min before behavioral tests.

Resident-Intruder Test.

To test aggression, a male intruder mouse of the same strain as the resident mouse, was placed in a resident home cage (24 cm×17 cm×12 cm) and resident-intruder interactions were videotaped for 10 min. Aggressive behavior of SI mice was characterized by an initial pattern of exploratory activity around the intruder, followed by rearing and tail rattle, accompanied within a few seconds by wrestling and/or a violent biting attacks. The total number of wrestling and attacks during the 10 min observation period was measured as previously described (Pinna et al., 2003, 2005), 60 min after drug administration. For every drug studied, SI mice were first exposed to three behavioral sessions, and then the average of basal aggression level for every single SI mouse was calculated; 2 days later, aggression levels following treatment were tested. Treated animals showing a reduction of the number of attacks less than 30% vs. the respective basal control values were considered as "low- to non-responders."

Locomotor Activity.

A computerized AccuScan 12 Animal Activity Monitoring System (Columbus Instruments, Columbus, Ohio, United States) assisted by VERSAMAX software (AccuScan Instruments, Columbus, Ohio, United States) was used to quantify locomotor activity (Pinna et al., 1997, 2006a). Each activity cage was made of a 20 cm×20 cm×20 cm Perspex box surrounded by horizontal and vertical infrared sensor beams. Horizontal sensors' beam interruptions were taken as a measure of horizontal activity. Activity was recorded from SI mice for 10 min beginning 60 min after a single injection of the drug.

Statistical Analyses.

Results are presented as means±SEMs unless otherwise indicated. Student's t-test, one-way ANOVA and two-way ANOVA repeated measures followed by Bonferroni post hoc test were performed to analyze experimental data; significance was set at $p<0.05$. $EC_{50}$ values were calculated from dose-response curves analyzed by the "quantal dose-response: probits test" using the computer program of Tallarida and Murray equipped with a statistical package (Tallarida and Murray, 1987). Statistical comparisons among the different ECsos were performed with the "cohort package software." (available at cohort.com).

Results

Development of Aggressive Behavior in Late and Early SI Adolescent Mice.

Figure 1:
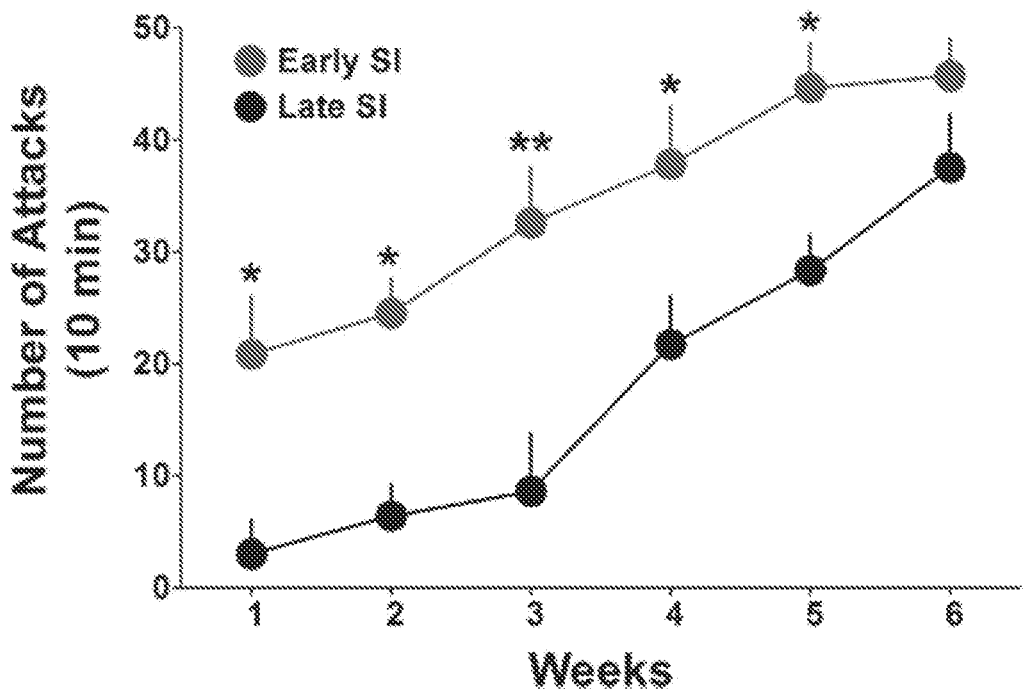
FIG. 1 shows a graph that can demonstrate onset of aggressive behavior in early and late adolescent SI mice. Representation of the development of the aggressive behavior in early (light grey) and late (black) adolescent SI mice from week 1 to 6 of social isolation. Early adolescent social isolation (started at day 21 of life, PND 21) induced a more severe development of aggression compared to late adolescent isolation (started at day 45 of life, PND 45). Data represent the mean±SEM of 15 mice. *$p<0.05$ and **$p<0.001$, when compared with late adolescent SI mice at the same time point.

The basal levels of aggressive behavior were determined in both late and early SI mice starting from the first week of isolation, by testing resident-intruder interactions once a week for 6 weeks (FIG. 1). It was observed that early isolation, which was started at PND 21, induced a more rapid and severe development of aggression compared to late social isolation, which was started at PND 45. Two-way ANOVA repeated measures revealed a significant effect of "onset of isolation" [F(1.140) D 42.23; p<0.0001], an effect of "time of test" [F(5.140) D 16.67; p<0.0001], but no interaction between factors [F(5.140) D 0.763; p D 0.578]. Bonferroni post hoc test showed a significant difference in the aggressive behavior between late and early SI mice in every week tested except week 6 (FIG. 1). Aggression levels were studied only in SI mice given that group-housed conditions do not account for relevant levels of aggression (Pinna et al., 2003, 2005).

S-FLX More Potently Improves Aggression in Late than Early SI Mice.

Figure 2A:
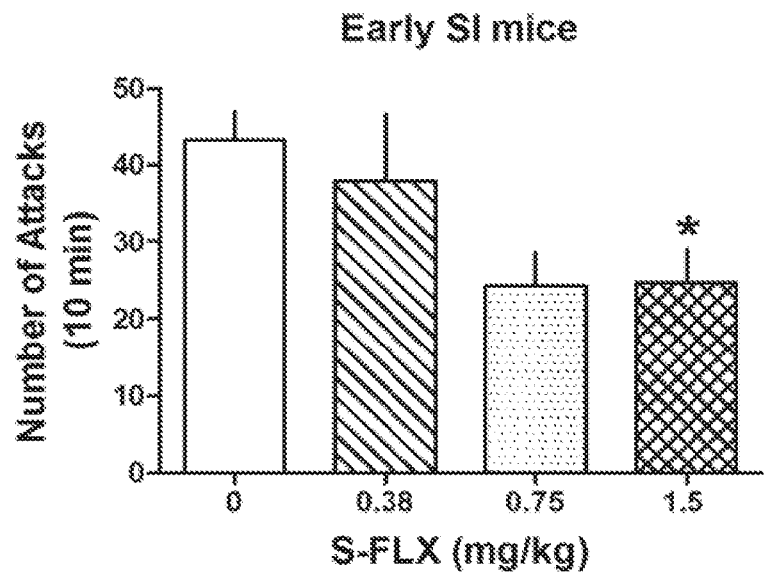
FIGS. 2A-2B show graphs that can demonstrate S-fluoxetine (S-FLX) can decrease aggressive behavior in early and late adolescent SI mice. S-FLX at the doses of 0.375, 0.75, and 1.5 mg/kg, i.p., was administered both to early (FIG. 12A) and late (FIG. 12B) adolescent SI mice 60 min before the resident-intruder test. In late adolescent SI mice, S-FLX reduced aggression at the dose of 0.75 mg/kg with an EC50 dose of 0.85 mg/kg, while in early adolescent SI mice, S-FLX induced a decrease of aggression with an EC50 dose of >1.5 mg/kg. Data represent the mean±SEM of 13-18 mice. *$p<0.05$; $p<0.01$; *$p<0.001$, when compared with basal control levels of aggression.
Figure 2B:
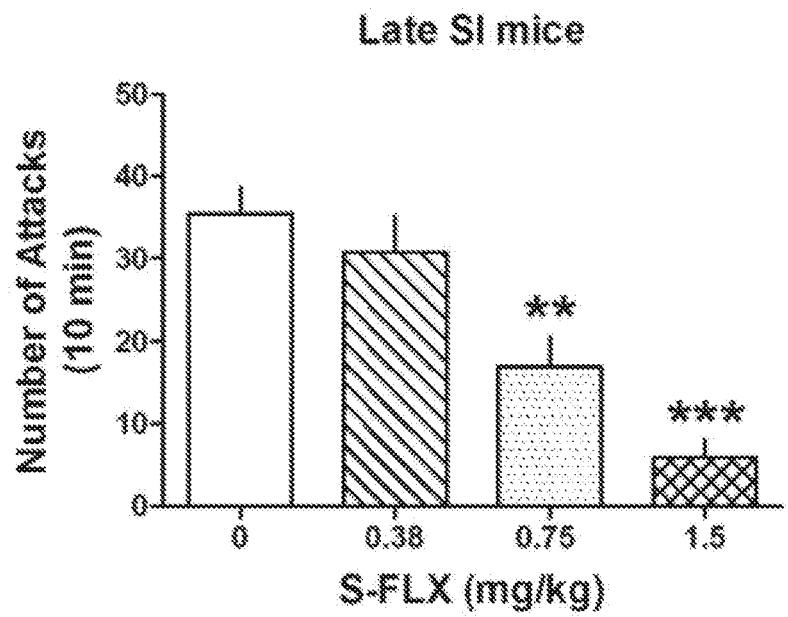

Administration of several doses of the SSRI, S-FLX (0.375, 0.75, and 1.5 mg/kg, i.p.) resulted in a stronger dose-dependent decrease of aggression in late than in early SI resident mice toward a same-sex intruder. One-way ANOVA showed that S-FLX reduced aggression in both late [F(3.84) D 13.08; p<0.0001] and early SI mice [F(3.91)= 3.823; p=0.013] (FIGS. 2A-2B). Bonferroni post hoc test showed a significant reduction in the number of attacks at the dose of 0.75 mg/kg (−52%, p<0.01, n=13) as well as 1.5 mg/kg (−83%, p<0.001, n=17) in late SI mice ($EC_{50}$ dose=0.85 mg/kg), but only at the highest dose (1.5 mg/kg) in early SI mice (−43% vs. basal value, p<0.05, n=18) ($EC_{50}$ dose>1.5 mg/kg). The S-FLX dose of 1.5 mg/kg was more potent in late [+316%, t(33) D 3.761, p=0.0007] than early SI mice.

GNX, BR351, and BR297 Decrease Aggression in Early and Late SI Mice.

Figure 3A:
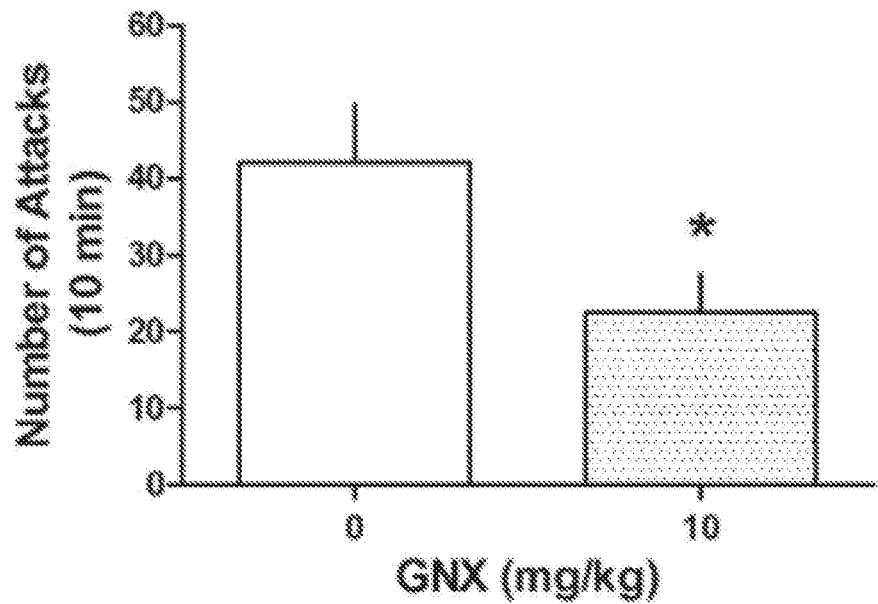
FIGS. 3A-3B shows graphs that can demonstrate that an analog of Allo, ganaxolone (GNX) can ameliorate aggressive behavior in early and late adolescent SI mice. GNX (10 mg/kg, $EC_{50}$ dose) was administered both to early (FIG. 3A) and late (FIG. 3B) adolescent SI mice 60 min before the exposure to a resident-intruder test. Equal doses of GNX showed a more powerful improvement in social isolation-induced aggression of late adolescent SI mice. Data represent the mean±SEM of 12-13 mice. *$p<0.05$; **$p<0.01$, when compared with basal control levels of aggression.
Figure 3B:
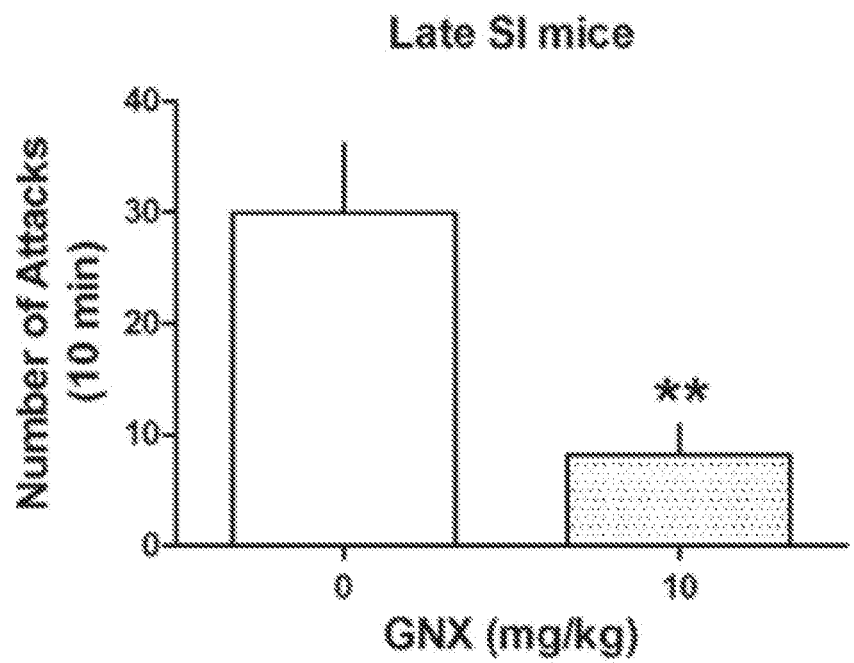

Administration of GNX at the $EC_{50}$ dose (10 mg/kg, i.p.; previously established in Pinna and Rasmusson, 2014) decreased aggression both in early and late SI mice [PND 21: −72%, t(24)=3.208, p=0.0038, n=13; PND 45: −46%, t(28)=2.164, p=0.039, n=12] (FIGS. 3A-3B]). The effect of GNX was observed to be stronger in late compared with early SI mice [+197%, t(22)=2.389, p=0.026].

Figure 4A:
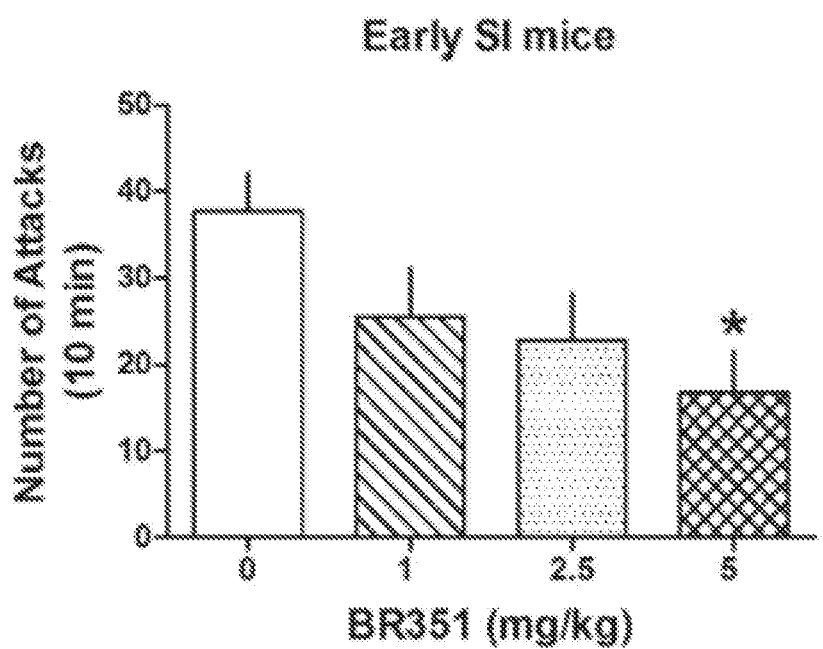
FIGS. 4A-4D show graphs that can demonstrate that the analogs of Allo, BR351 and BR297 decrease aggressive behavior in early and late adolescent SI mice. BR351 at the doses of 1, 2.5, and 5 mg/kg was administered both to early (FIG. 4A) and late (FIG. 4B) adolescent SI mice 60 min before the exposure to a resident-intruder test. The dose of 5 mg/kg was observed to improve aggression of SI mice with higher potency in late ($EC_{50}$=3.75 mg/kg) than early ($EC_{50}$=4.5 mg/kg) adolescent SI mice. BR297 at the doses of 0.3125, 0.625, and 2.5 mg/kg was administered both to early (FIG. 4C) and late (FIG. 4D) adolescent SI mice 60 min before the exposure to a resident-intruder test. Dose-response data analyses showed that BR297 was equally potent in decreasing aggression of early and late adolescent SI mice with an $EC_{50}$ dose of 0.25 mg/kg. Data represent the mean±SEM of 10-16 mice. *$p<0.05$; $p<0.01$; *$p<0.001$, when compared with basal control levels of aggression.
Figure 4B:
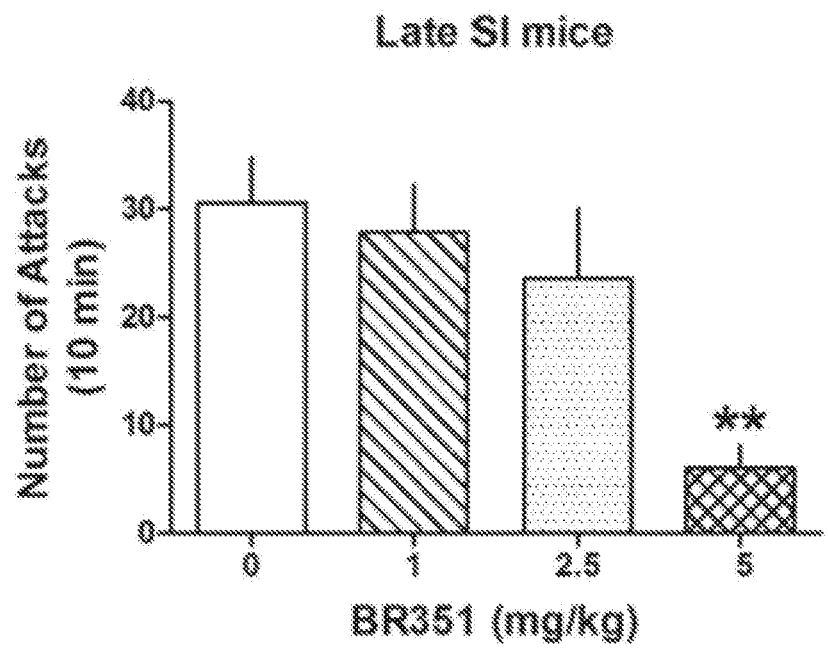

BR351 (1, 2.5, and 5 mg/kg) reduced aggression in late [F(3.62)=4.458; p=0.0067] and early SI mice [F(3.70)= 3.5303; p=0.0192] (FIGS. 4A-4B) only at the highest dose. Bonferroni analyses showed a reduction of attacks in late SI mice at the dose of 5 mg/kg (−80% vs. basal value, p<0.01, n=12) ($EC_{50}$ dose=3.75 mg/kg), and in the early SI mice at the dose of 5 mg/kg (−56%, p<0.05, n=16) ($EC_{50}$ dose=4.5 mg/kg). There was a trend showing a higher potency of BR351 (5 mg/kg) in late compared to early SI mice [+179%, t(26)=1.821, p=0.0801].

Figure 4C:
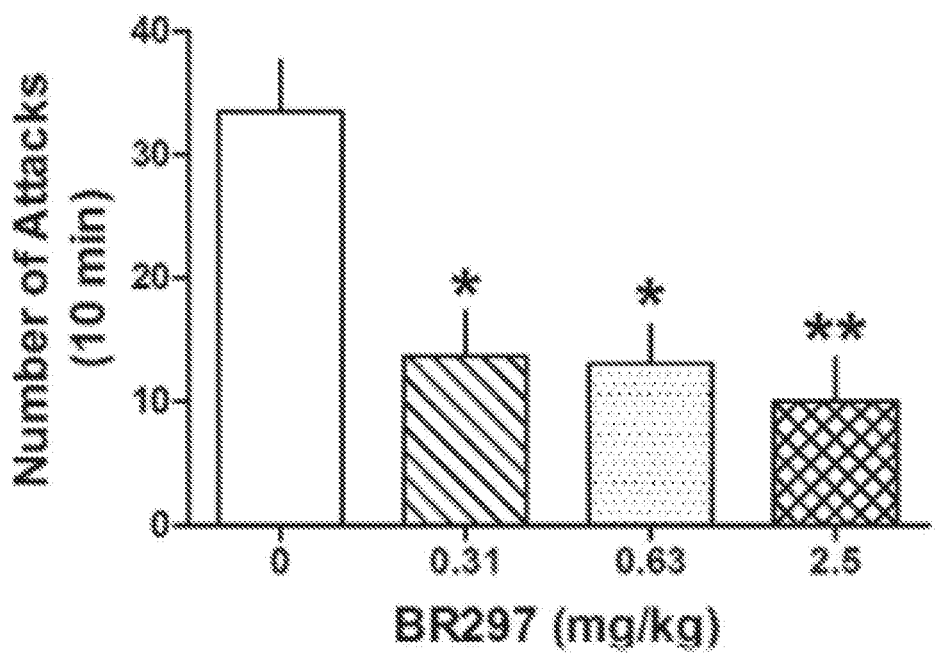
Figure 4D:
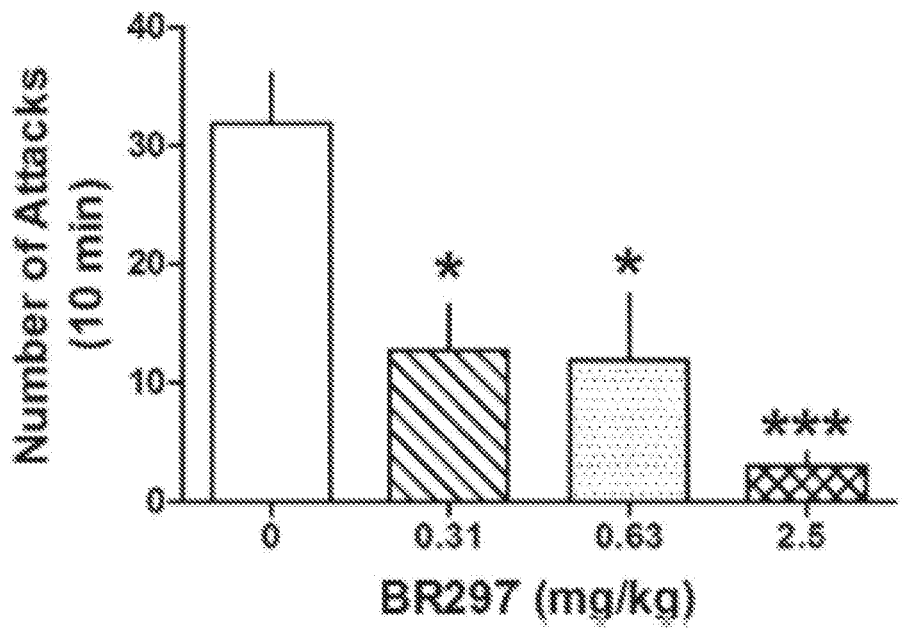
Figure 5A:
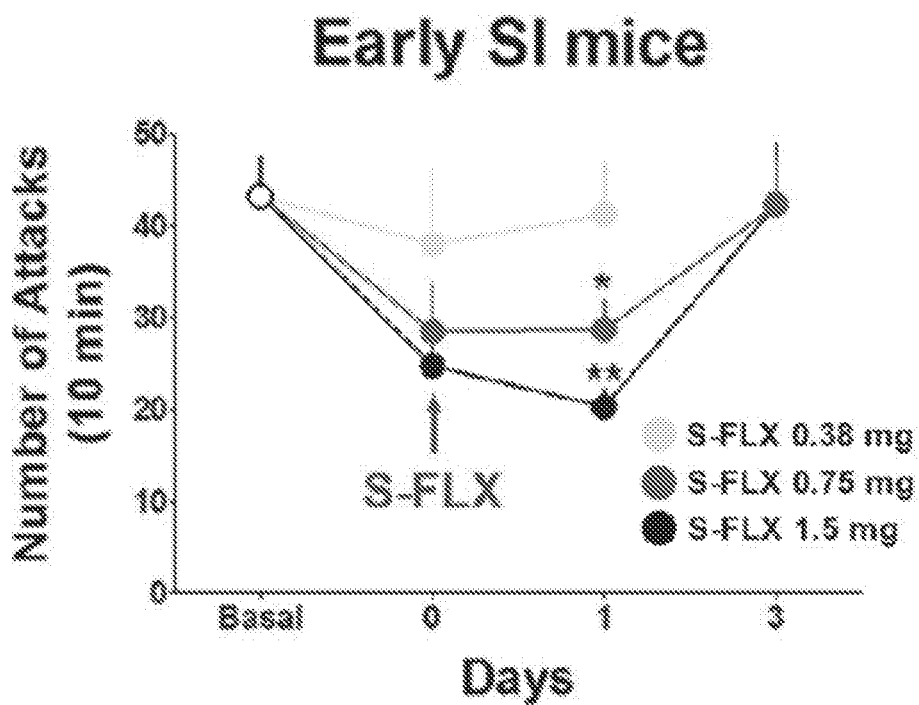
FIG. 5A-5H shows graphs that can demonstrate drug-induced time-dependent anti-aggressive effect in late and early adolescent SI mice. Graphs represent the gradual reinstatement of aggressive behavior both in early (FIG. 5A) and late (FIG. 5B) adolescent SI mice during the period following the single dose administration of S-FLX (Day 0). Aggression rapidly rebounded after 3 days from S-FLX administration in both groups of mice. After an $EC_{50}$ dose of GNX aggressive behavior was observed to rebound to basal values only after 1 day in early adolescent (FIG. 5C) SI mice and after 5 days in late adolescent (FIG. 5D) SI mice. The gradual time-dependent reinstatement of aggressive behavior lasted 5 days in early (FIG. 5E) and late (FIG. 5F) adolescent SI mice after the administration of BR351 at the dose of 2.5 mg/kg; the duration of BR351 effect was 5 days also at the dose of 5 mg/kg in late SI mice, and 3 days in early SI mice. The anti-aggressive effect of a single dose administration of BR297 was long-lasting and required 7 days in early SI mice (FIG. 5G), and 9 days in late SI mice (FIG. 5H) to return to basal values. Data represent the mean±SEM of 7-18 mice. *$p<0.05$; **$p<0.01$, when compared with basal control levels of aggression.
Figure 5B:
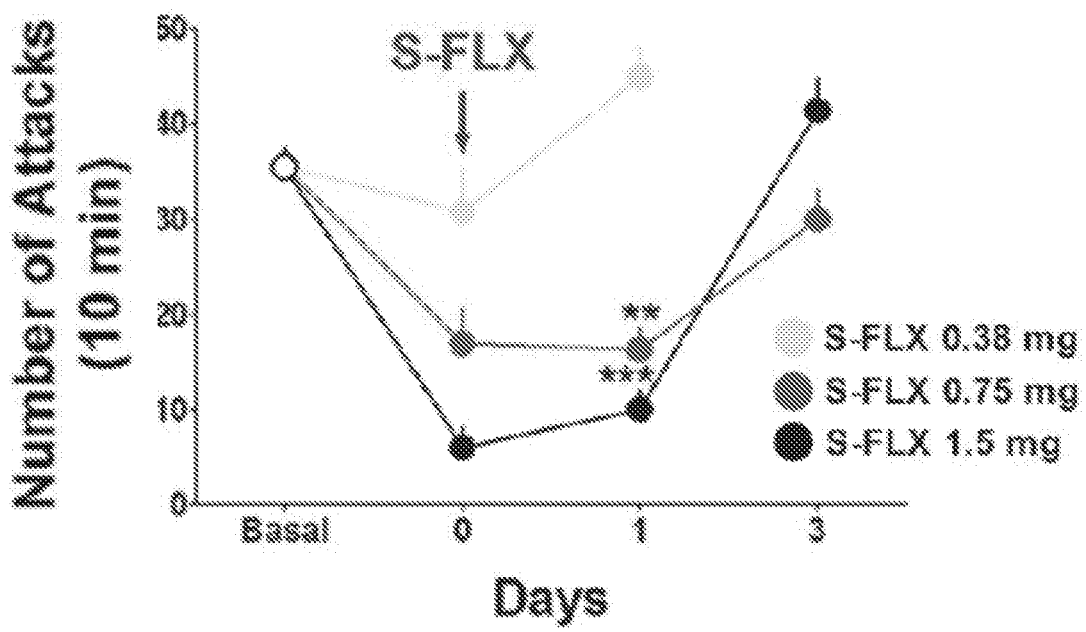
Figure 5C:
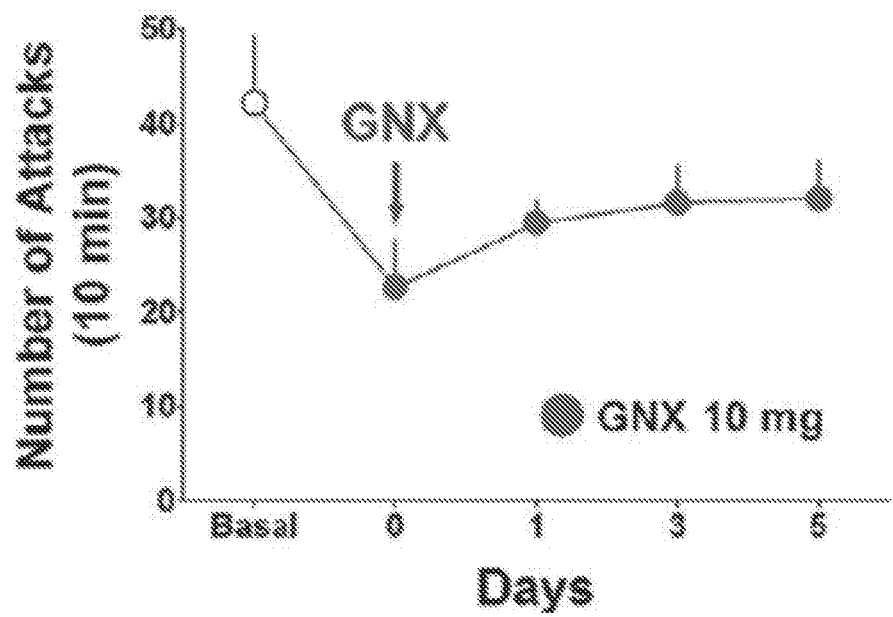
Figure 5D:
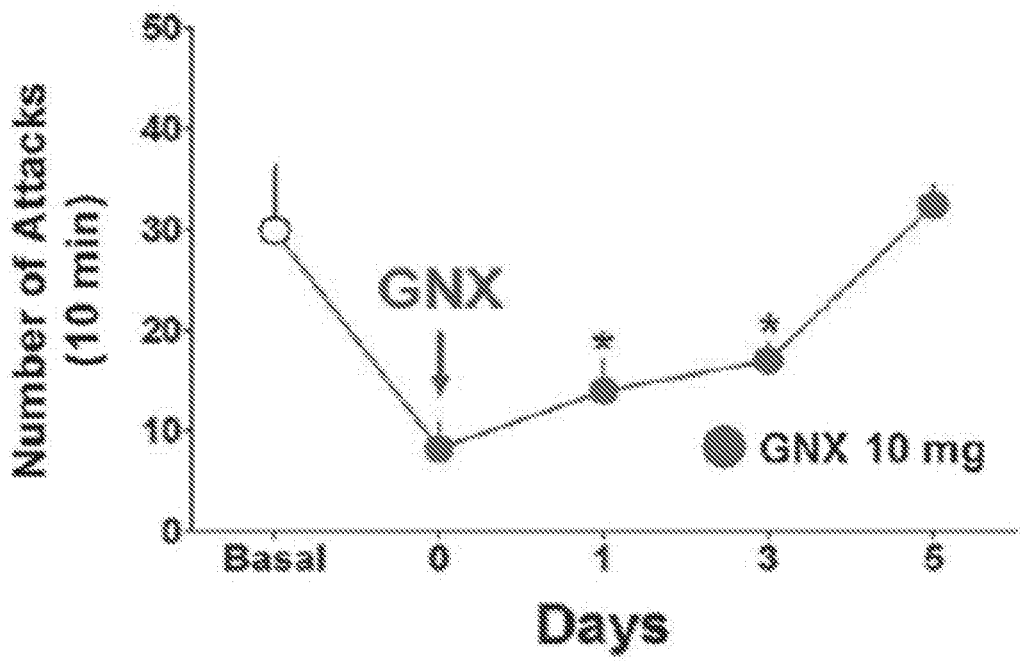
Figure 5E:
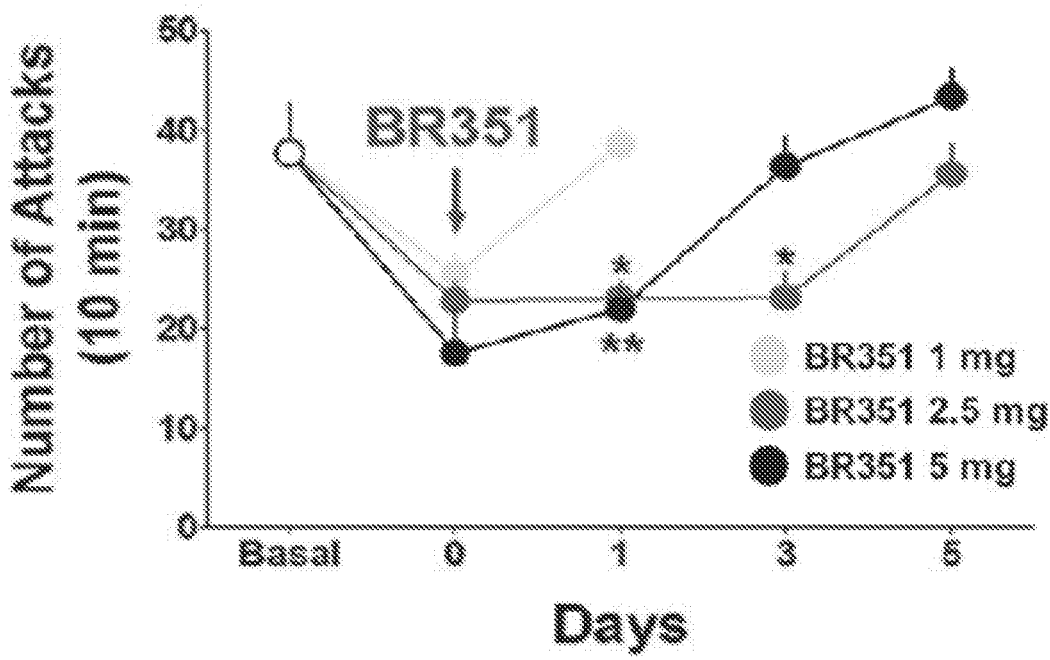
Figure 5F:
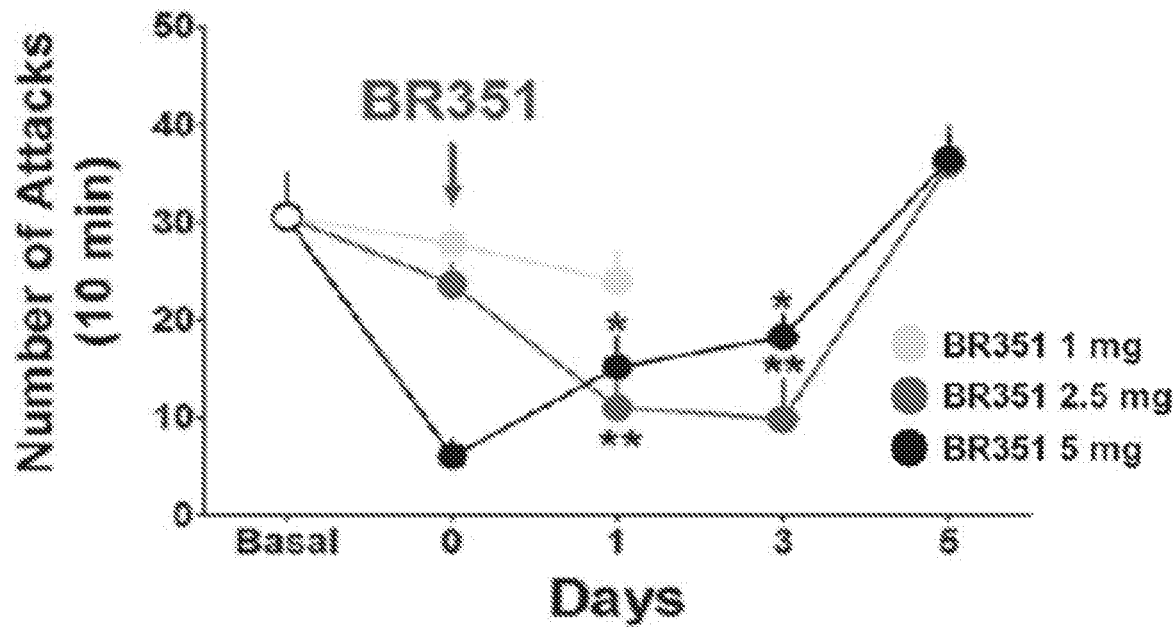
Figure 5G:
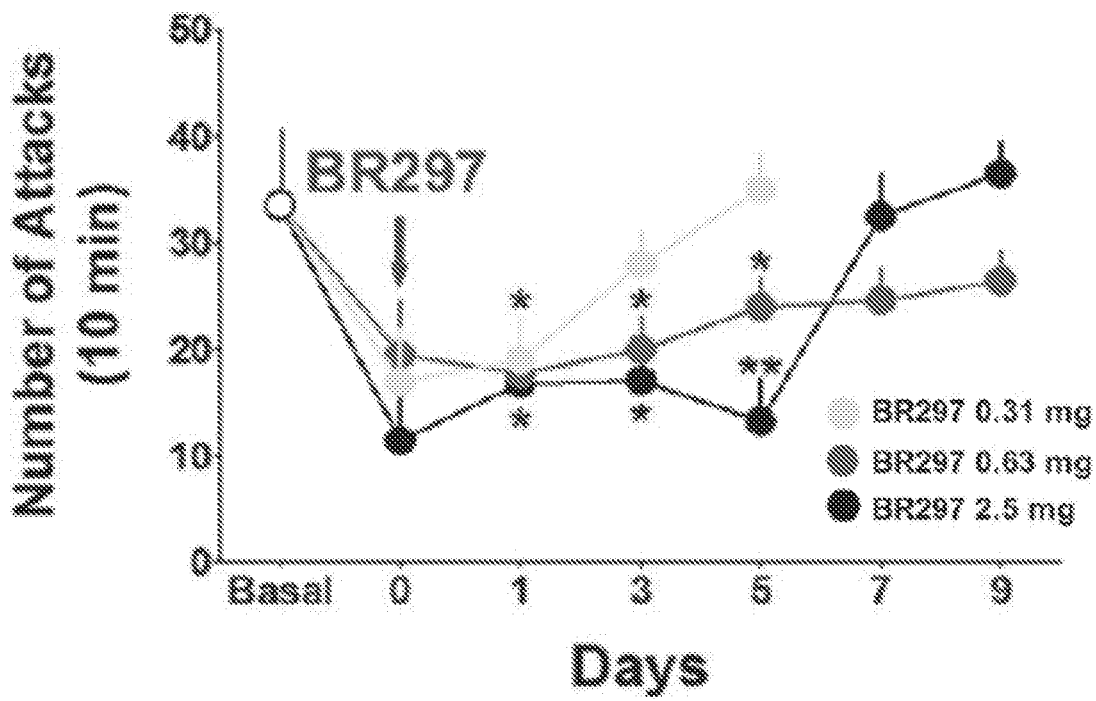
Figure 5H:
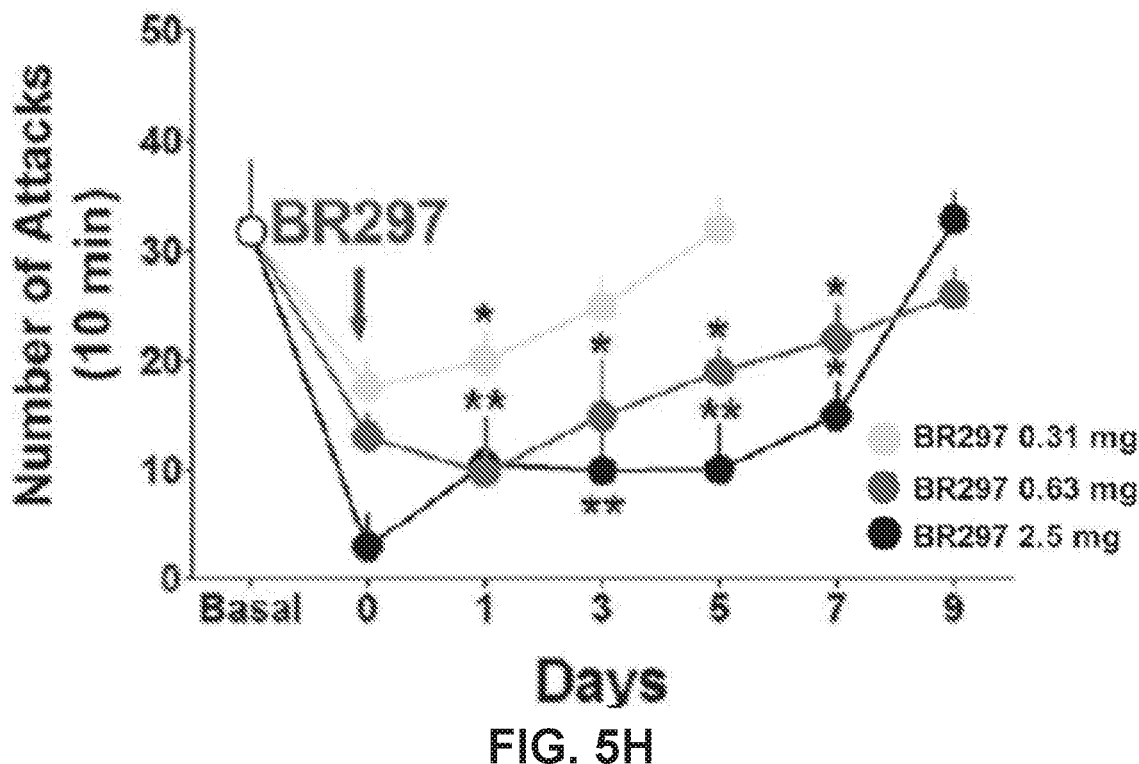
Figure 6A:
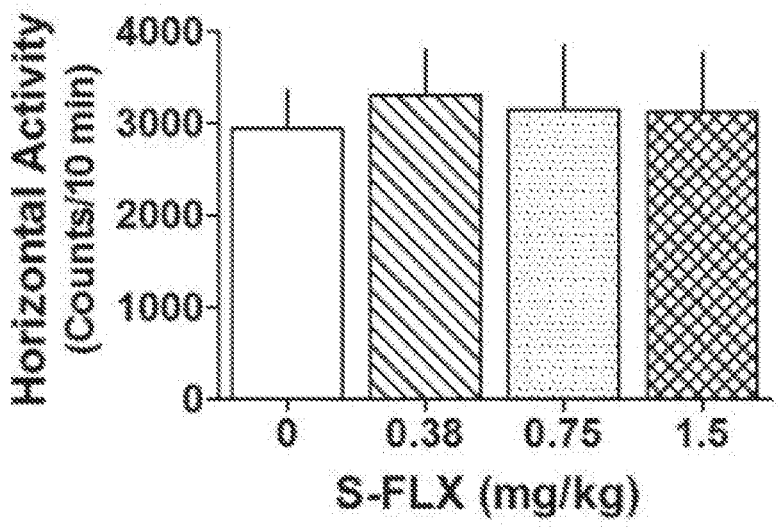
FIGS. 6A-6H show graphs that can demonstrate the effect of different drug treatments on locomotor activity both in late and early adolescent SI mice. S-FLX (FIGS. 6A-6B), GNX (6C-6D), BR351 (6E-6F), and BR297 (6G-6H), were administered to early and late adolescent SI mice 60 min before the exposure to the locomotor activity test. All drugs at the dose tested failed to alter locomotion patterns of SI mice. Data represent the mean±SEM of 7-18 mice.
Figure 6B:
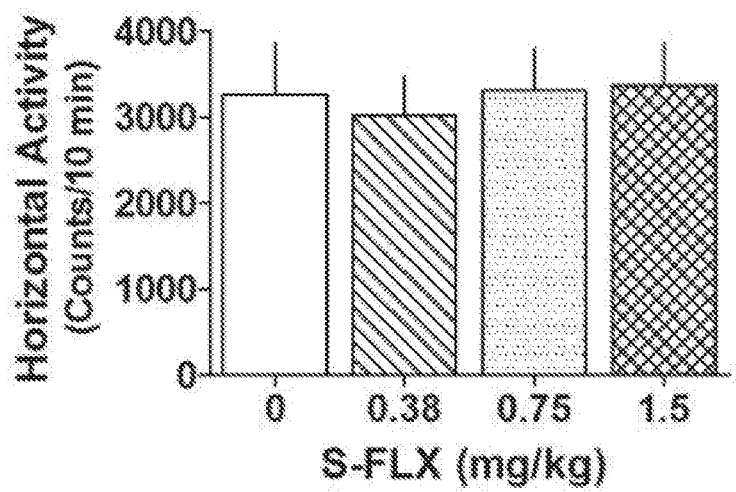
Figure 6C:
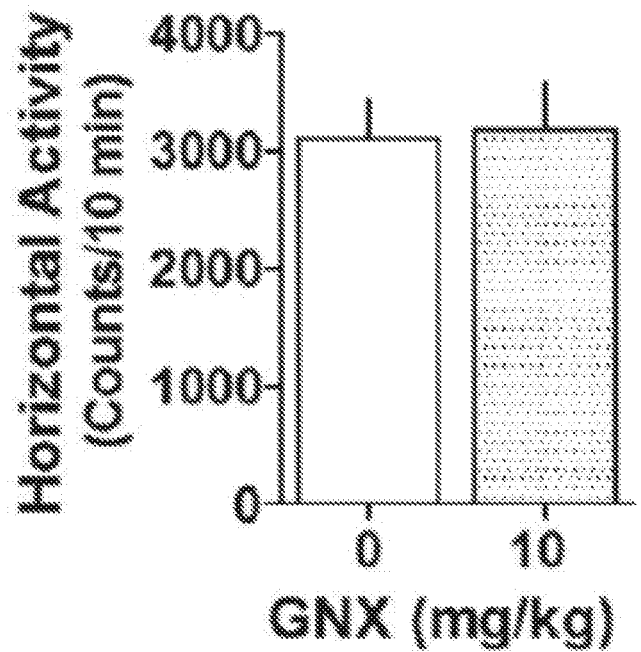
Figure 6D:
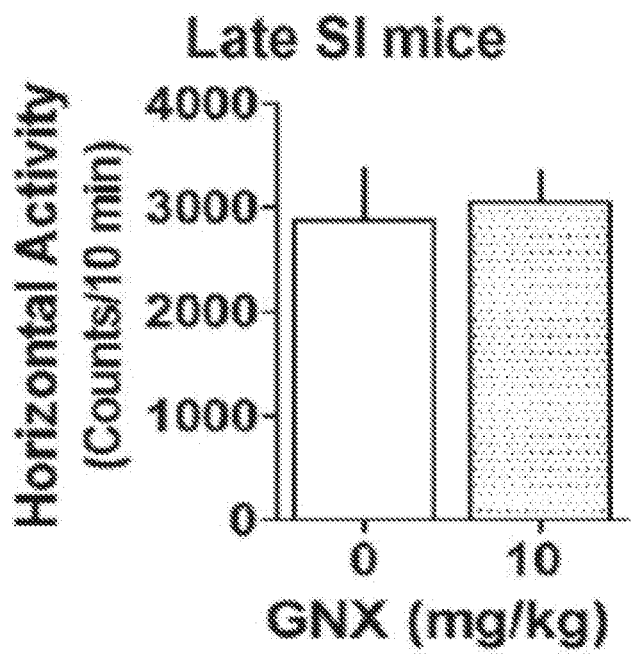
Figure 6E:
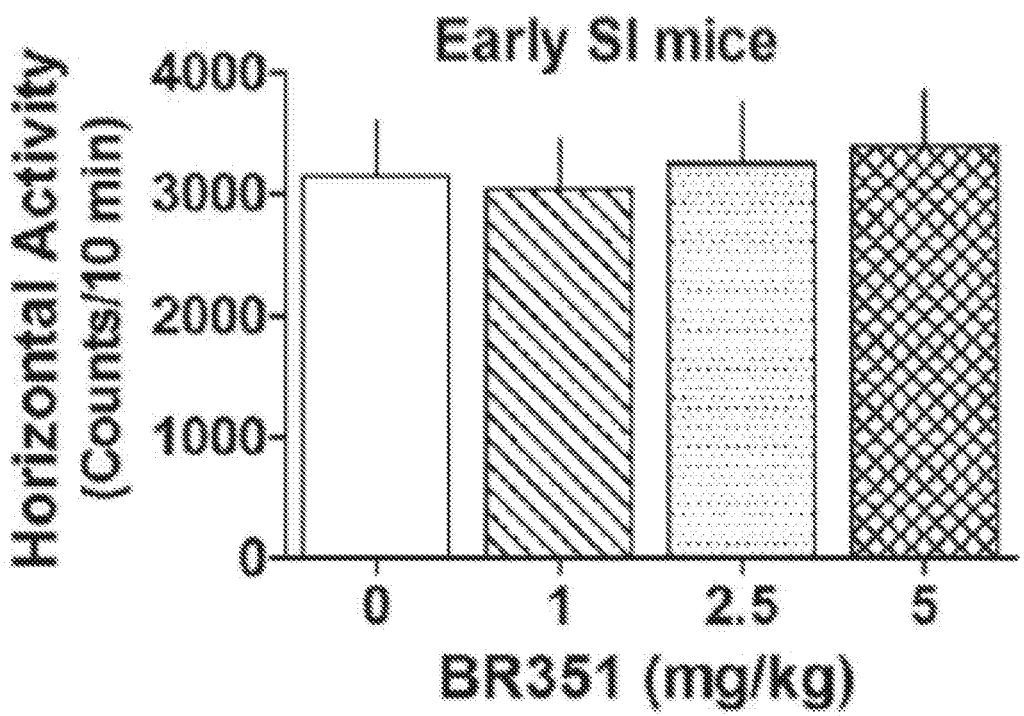
Figure 6F:
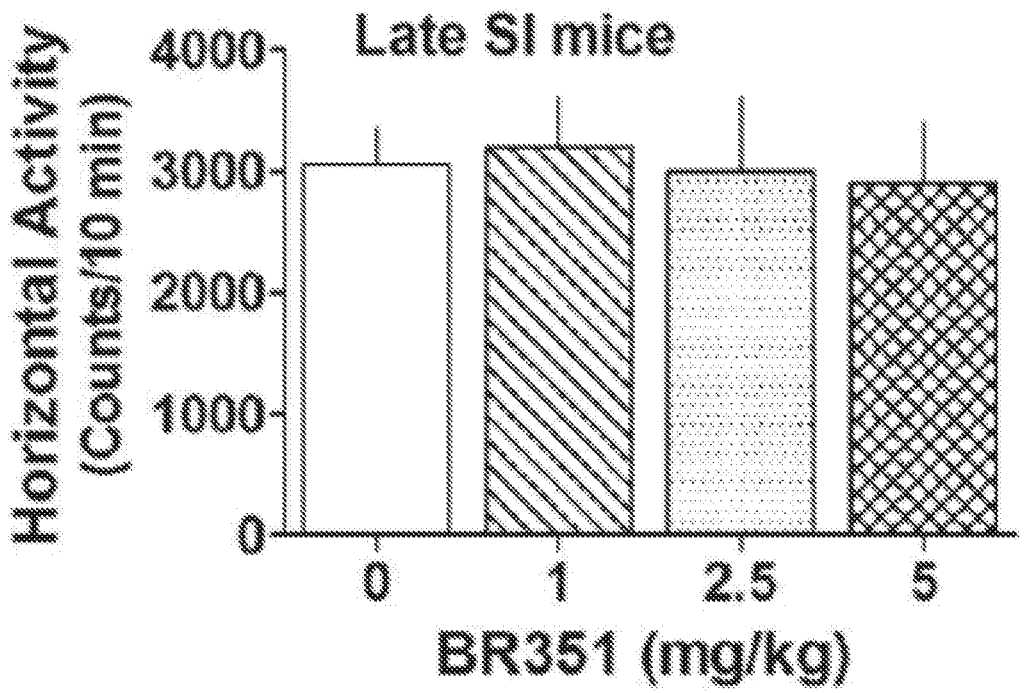
Figure 6G:
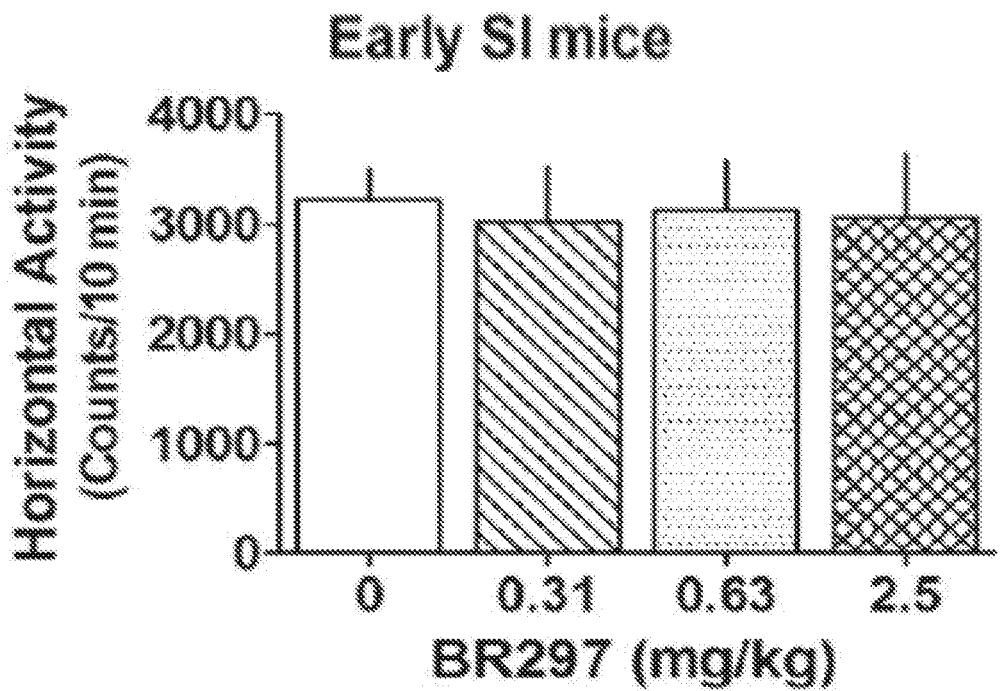
Figure 6H:
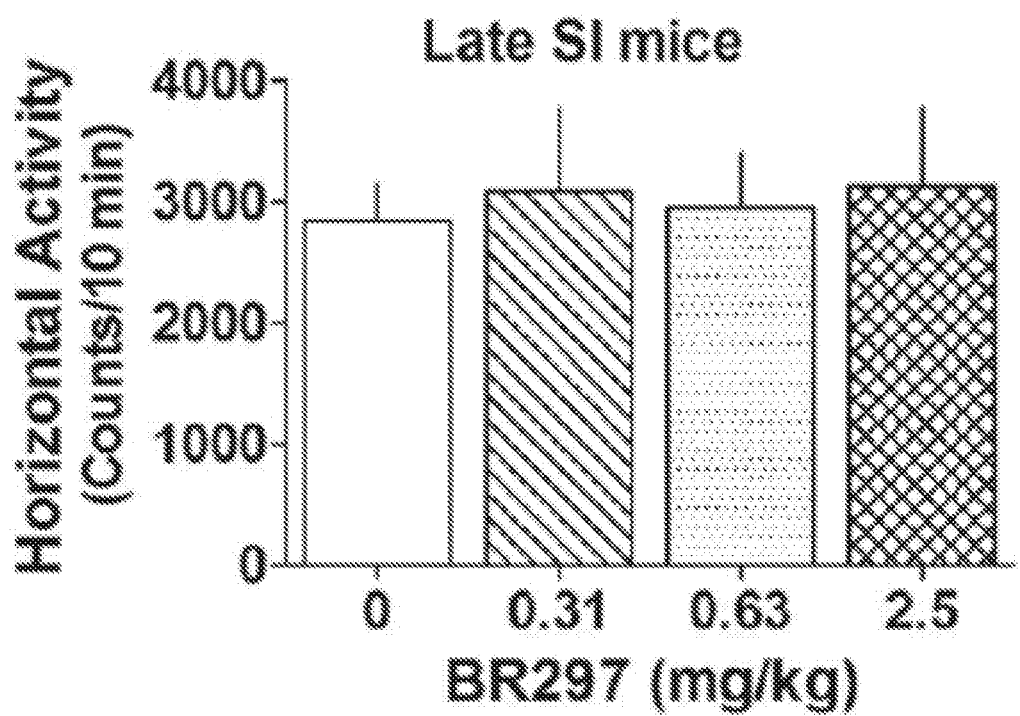

BR297 (0.3125, 0.625, and 2.5 mg/kg) robustly reduced aggression in late [F(3.62)=8.213; p<0.0001] and early SI mice [F(3.74)=7.512; p=0.0002] (FIGS. 4C-4D). Bonferroni showed a reduction of aggression at all the doses tested in the late (0.3125 mg/kg: −60%, p<0.05, n=11; 0.625 mg/kg: −63%, p<0.05, n=11; 2.5 mg/kg: −91%, p<0.001, n=12) ($EC_{50}$ dose=0.25 mg/kg) and in early SI mice (0.3125 mg/kg: −59%, p<0.05, n=10; 0.625 mg/kg: −61%, p<0.05, n=14; 2.5 mg/kg: −70%, p<0.01, n=16) ($EC_{50}$ dose=0.25 mg/kg). The effect of BR297 (2.5 mg/kg) showed a trend to lower potency in the early SI mice [+235%, t(26)=1.66, p=0.108].

Duration of Drug-Induced Anti-Aggressive Effects in Early and Late SI Adolescent Mice.

The duration of the anti-aggressive effect for each drug was assessed in a follow-up study after a single dose administration (FIGS. 5A-5H). Aggression rapidly rebounded after 1 day of S-FLX (0.375 mg/kg) administration and after 3 days at the dose of 0.75 mg/kg [PND 21, day 1: t(62)=2.087, p=0.041; PND 45, day 1: t(58)=3.444, p=0.0011] and 1.5 mg/kg [PND 21, day 1: t(63)=3.122, p=0.0027; PND 45, day 1: t(59)=3.59, p=0.0007] both in early and late adolescent SI mice.

GNX anti-aggressive effect (10 mg/kg) lasted 5 days in late SI mice [day 1: t(27)=2.408, p D 0.0232; day 3: t(27)=2.069, p=0.0482]; the same trend was observed in early SI mice without significant effect.

Aggression was restored 1 day after BR351 at the dose of 1 mg/kg, and after 5 days at the doses of 2.5 mg/kg [day 1: t(51)=2.979, p=0.0044; day 3: t(47)=3.034, p=0.0039] and 5 mg/kg [day 1: t(47)=2.263, p=0.0283; PND 45, day 3: t(48)=2.083, p=0.0426] in late SI mice. Moreover, BR351 anti-aggressive effect rapidly extinguished at the dose of 1 mg/kg, after 5 days at the dose of 2.5 mg/kg [day 1: t(42)=2.299, p=0.0266; day 3: t(42)=2.038, p=0.0479], and after 3 days at the dose of 5 mg/kg [day 1: t(42)=2.188, p=0.0343].

BR297 at 0.625 mg/kg [day 1: t(46)=3.395, p=0.0014; day 3: t(41)=2.195, p=0.0339; day 5: t(42)=2.269, p=0.0285; day 7: t(47)=2.413, p=0.0198] and 1.5 mg/kg doses [day 1: t(46)=3.320, p=0.0018; day 3: t(47)=3.441, p=0.0012; day 5: t(46)=3.552, p=0.0016; day 7: t(46)=2.511, p=0.0156] inhibited aggression for 9 days in late SI mice. Furthermore, BR297 dose of 0.3125 mg/kg significantly reduced aggressive behavior for 3 days in the same experimental group [day 1: t(50)=2.154, p=0.0361]. The long-term effect of BR297 in early SI mice was similar to that observed in late SI mice but not identical. The duration of the effect was 3 days at the dose of 0.3125 mg/kg [day 1: t(52)=2.175, p=0.0342], and 7 days at the dose of 0.625 mg/kg [day 1: t(52)=2.234, p=0.0298; day 3: t(55)=2.083, p=0.0419; day 5: t(58)=2.038, p=0.0461] and 2.5 mg/kg [day 1: t(53)= 2.518, p=0.0149; day 3: t(53)=2.386, p=0.0206; day 5: t(53)=3.159, p=0.0029].

Drug Non-Response Rate in Early and Late SI Mice.

The rate of SI mice that did not respond to the drugs' pharmacological action was assessed by a decrease of aggression of less than or equal to 30%. Generally, a higher rate of non-response was assessed in early vs. late SI mice (see Table 2, for details). The percentage of non-responders to S-FLX at the higher dose of 1.5 mg/kg was 11.64 and 22.22% in late and early SI mice, respectively. Both in the late and early SI mice, the non-response rate at the highest doses tested of BR351 (5 mg/kg) was 8.33 and 13.33%, respectively, and at the BR297 dose of 2.5 mg/kg; 0 and 6.25%, respectively. Finally, the non-response rate at the EC50 dose of GNX (10 mg/kg) for both late and early SI mice was 15.38 and 25%, respectively.

TABLE 2

Rate of adolescent SI mice that show resistance to the single administration of S-fluoxetine (S-FLX) and PEA

| Drug Treatment | "Non-responders" Late SI mice (%) | "Non-responders" Late SI mice (n) | "Non-responders" Early SI mice (%) | "Non-responders" Early SI mice (n) |
|---|---|---|---|---|
| S-FLX 0.375 mg | 64.3 | 9/14 | 64.3 | 9/14 |
| S-FLX 0.75 mg | 23.1 | 3/13 | 53.3 | 8/15 |
| S-FLX 1.5 mg | 11.8 | 2/17 | 22.2 | 4/18 |
| GNX 10 mg | 15.4 | 2/13 | 25.0 | 3/12 |
| BR351 1 mg | 54.6 | 6/11 | 50.0 | 8/16 |
| BR351 2.5 mg | 40.0 | 4/10 | 20.0 | 3/15 |
| BR351 5 mg | 8.3 | 1/12 | 13.3 | 1/16 |
| BR297 0.3125 mg | 18.2 | 2/11 | 30.0 | 3/10 |
| BR297 0.625 mg | 18.2 | 2/11 | 21.4 | 3/14 |
| BR297 2.5 mg | 0 | 0/12 | 6.3 | 1/16 |

Effects of Different Drug Treatments on Locomotor Activity in Early and Late SI Mice.

A summary of the locomotor activity after all drug tested is shown in FIGS. 6A-6H. S-FLX did not reduce exploratory activity in late and early SI mice at all doses tested. Similarly, exploratory activity was not altered by a single dose treatment with PEA at all doses tested.

Discussion

This Example focused on the aggression expressed by SI mice because it is easy to reproduce, reliable to measure, and fails to decrease after multiple tests (Pinna et al., 2003, 2004; Matsumoto et al., 2005; Nelson and Pinna, 2011). Basal levels of aggression were determined in three resident-intruder tests before performing each of the drug-treated aggression experiment during which, aggression levels for each mouse were monitored before, during and after drug treatment. The effects induced by different classes of drugs, e.g., SSRIs at steroidogenic doses that act as SBSSs, and endocannabinoids that induce neurosteroidogenesis were compared, on the aggression of mice socially isolated in early (PND 21) and late (PND 45) adolescence. These data can demonstrate that: (1) social isolation in early adolescence results in faster development of and a more persistent aggression than isolation in late adolescence (FIG. 1); (2) early isolation was associated with a higher treatment resistance rate Table 2); and (3) a lower duration of the drugs' antiaggressive effects (FIGS. 5A-5H). A single dose of the Allo analogue BR297 induced a dose-dependent robust anti-aggressive effect (FIGS. 4A-4D) and the anti-aggressive effect of BR297 was long-lasting.

These effects were compared to S-FLX's potency, duration of effects and non-response rate. BR297 appeared to be more efficacious as an anti-aggressive agent than S-FLX in both early and late adolescent isolation. Mice isolated at PND21 developed a more severe and persistent aggressive behavior when compared to those isolated at PND45; second, this effect is associated with a higher "non-response" rate toward the drugs tested and a weaker response to S-FLX; third, there was a reduced temporal improvement of behavior following a drug's single dose administration.

One of the best characterized behavioral dysfunctions following protracted social isolation in rodents is the development of aggressive behavior (Valzelli, 1969; Pinna et al., 2003). In SI mice, aggression co-occurs with other emotional behavioral deficits, including enhanced contextual fear and impaired fear extinction, and anxiety-like behavior, which are associated with reduced corticolimbic Allo levels and subsequent GABAergic neurotransmission dysfunction (Dong et al., 2001; Pinna et al., 2003, 2006b; Serra et al., 2006; Matsumoto et al., 2007; Zhang et al., 2014). Remarkably, patients with MDD and PTSD also show a CSF and brain Allo level down-regulation which is correlated with the severity of symptoms (Romeo et al., 1998; van Broekhoven and Verkes, 2003; Uzunova et al., 1998, 2006; Agis-Balboa et al., 2014). These findings suggest that the SI mouse may offer a suitable model to assess the effect of compounds and/or drugs to treat endophenotypic expressions of behavioral deficits that translate into symptoms of psychiatric disorders, including MDD and PTSD. Reduced corticolimbic Allo levels can be upregulated in humans by treatment with SSRIs that also correlates with improved symptoms (Romeo et al., 1998; Uzunova et al., 2006; Agis-Balboa et al., 2014). Further, patients who fail to show behavioral improvements also fail to show CSF Allo level upregulation (Uzunova et al., 1998, 2006). In SI mice, a single low dose of S-FLX, which is devoid of serotoninergic effects, by acting as a SBSSs, e.g., selectively stimulating brain Allo biosynthesis, is associated with reduced aggression and improvement of other emotional behaviors (Pinna et al., 2003, 2009; Pibiri et al., 2008; Nin et al., 2011a). BR297 was a strong anti-aggressive agent and the non-response rate of early adolescent SI mice that were treated with BR351 or BR297 was significantly lower than those receiving the higher dose of S-FLX. The other Allo' analog tested, GNX was also efficient in reducing aggression in early SI mice. BR297 and BR351 were observed to have an anti-aggressive action in SI mice. These results can evidence the benefit of neurosteroid and their analogues as anti-aggressive agents and can provide benefits in treating neuropsychiatric disorders characterized by impulsive aggression, including but not limited to, PTSD and MDD.

Clinical findings show that only 50% of depressed patients respond to first-line therapy antidepressants, while more than one third of responders develop resistance to antidepressants (Kemp et al., 2008). It is generally accepted that early traumatic experiences cause a poor response to SSRI treatments later in adulthood, representing one of main causes for pharmaco-resistance. For example, abuse in general but—most notably—abuse occurring at 7 years of age or younger predicted a lower response to 8 weeks of SSRI antidepressants (Williams et al., 2016). Likewise results from this Example can show that behavioral deficits are more difficult to improve or modulate in mice subjected to early social isolation than mice who are socially isolated later in adolescence using the same drug doses. Furthermore, these preclinical findings together with clinical observations of high incidence of resistance to current prescribed SSRI medication at supposedly steroidogenic doses can suggest that the deficits in the activity of enzymes that are involved in Allo biosynthesis may not be fully counteracted by SSRIs in a portion of depressed and PTSD patients.

The results showed that an alternative and valid strategy to overcome behavioral deficits might be to directly modulate $GABA_A$ receptors with analogs of Allo. GNX, BR351, or BR297 can be a suitable future approach for patients for whom an SSRI/SBSS is ineffective because of their inability to overcome impairment in neurosteroidogenesis (Gulinello et al., 2003). Other studies not shown here showed that a single dose administration with GNX given to SI mice blocked reconsolidation of fear memories and reduced contextual fear and facilitated fear extinction, which failed to re-emerge via "spontaneous recovery" (Pinna and Rasmusson, 2014). While not being bound by theory, reinforcing the impact of a neurosteroid-based therapy for PTSD and depression are recent studies showing that remission of post-partum depression was induced in 70% of patients treated with a two-day course of intravenous Allo compared to 10% who received placebo. This symptom improvement was rapid (60 h) and lasted for 30 days (Herper, 2016; Meltzer-Brody, 2016; Kanes et al., 2017).

REFERENCES FOR EXAMPLE 1

Agid, O., et al. (1999). Mol. Psychiatry 4, 163-172.
Agis-Balboa, et al. (2014) Psychopharmacology 231, 3569-3580.
Berton, O., and Nestler, E. J. (2006). Nat. Rev. Neurosci. 7, 137-151.
Bremner, J. D., et al. (2000). Am. J. Psychiatry 157, 1120-1126.
Choudary, et al. (2005). Proc. Natl. Acad. Sci. U.S.A. 102, 15653-15658.
Coplan, J. D., et al. (2014). Front. Behav. Neurosci. 8:189.
Dong, E et al. (2001). Proc. Natl. Acad. Sci. U.S.A. 98, 2849-2854.
Dube, S. R., et al. (2001). JAMA 286, 3089-3096.
El-Hage, W., et al. (2013). Front. Pharmacol. 4:146.
Famularo, R., et al. (1992). J. Am. Acad. Child Adolesc. Psychiatry 31, 863-867.
Fatemi, S. H., et al. (2013). Transl. Psychiatry 3:e303.
Felitti, V. J., et al. (1998) Am. J. Prev. Med. 14, 245-258.
Ferri, F. F. (2016). Ferri's Clinical Advisor 2017: 5 Books in 1. Amsterdam: Elsevier.
Geuze, E., et al. (2008). Mol. Psychiatry 13, 74-83.
Golden, R. N., et al. (2002). J. Clin. Psychiatry 63, 577-584.
Gulinello, M., et al. (2003). Neuroreport 14, 43-46.
Heim, C., and Nemeroff, C. B. (2001). Biol. Psychiatry 49, 1023-1039.
Herper, M. (2016). Available at: www.forbes.com
Ipser, J. C., and Stein, D. J. (2012 Int. J. Neuropsychopharmacol. 15, 825-840.
Kanes, S., et al. (2017). Lancet 390, 480-489. doi:
Kemp, A. H., et al (2008). CNS Spectr. 13, 1066-1086.

Kendler, K. S., Kuhn, J. W., and Prescott, C. A. (2004). Psychol. Med. 34, 1475-1482.
Kessler, R. C. (1997). Annu. Rev. Psychol. 48, 191-214.
Kessler, R. C., et al. (2005). Arch. Gen. Psychiatry 62, 593-602.
Klempan, T. A., et al. (2009). Mol. Psychiatry 14, 175-189.
Lanquillon, S., et al. (2000). Neuropsychopharmacology 22, 370-379.
Locci, A., and Pinna, G. (2017a). Br. J. Pharmacol.
Locci, A., and Pinna, G. (2017b). Soc. Neurosci. Abstr. 2017:13420.
Luscher, B., Shen, Q., and Sahir, N. (2011). Mol. Psychiatry 16, 383-406.
Matsumoto, K., et al. (2005). Stress 8, 85-93.
Matsumoto, K., et al. (2007). Stress 10, 3-12.
McCauley, J., et al. (1997). JAMA 277, 1362-1368.
Meltzer-Brody, S. (2016). A Study to Evaluate SAGE-547 in Patients With Severe Postpartum Depression. ClinicalTrials.gov identifier: NCT02614547 70.M. Thousand Oaks, Calif.: Sage.
Merali, Z., et al. (2004). J. Neurosci. 24, 1478-1485.
Nanni, V., Uher, R., and Danese, A. (2012). Am. J. Psychiatry 169, 141-151.
Nelson, M., and Pinna, G. (2011). Neuropharmacology 60, 1154-1159.
Nemeroff, C. B. (2008). Neuron 59, 185-186.
Nin, M. S., et al. (2011a). Front. Endocrinol. 2:73.
Nin, M. S., et al. (2011b). Trab. Inst. Cajal 83, 215-216.
Pibiri, F., et al. (2008). Proc. Natl. Acad. Sci. U.S.A. 105, 5567-5572.
Pinna, G., et al. (2004). Proc. Natl. Acad. Sci. U.S.A. 101, 6222-6225.
Pinna, G., et al. (2005). Proc. Natl. Acad. Sci. U.S.A. 102, 2135-2140.
Pinna, G., et al. (2006a). Proc. Natl. Acad. Sci. U.S.A. 103, 4275-4280.
Pinna, G., Costa, E., and Guidotti, A. (2006b). Psychopharmacology 186, 362-372.
Pinna, G., Costa, E., and Guidotti, A. (2009). Curr. Opin. Pharmacol. 9, 24-30.
Pinna, G., et al. (2003). Proc. Natl. Acad. Sci. U.S.A. 100, 2035-2040.
Pinna, G., et al. (1997). Proc. Natl. Acad. Sci. U.S.A. 94, 2719-2723.
Pinna, G., and Rasmusson, A. M. (2014). Front. Cell. Neurosci. 8:256.
Prigerson, H. G., et al. (2001). J. Nerv. Ment. Dis. 189, 99-108.
Rasmusson, A. M., et al. (2017). Neurosci. Lett. 649, 156-163.
Romeo, E., et al. (1998). Am. J. Psychiatry 155, 910-913.
Rush, A. J., et al. (2006). Biol. Psychiatry 59, 493-501.
Sasso, O., et al. (2012). Pain 153, 33-41.
Sequeira, A., et al. (2009). PLoS ONE 4:e6585.
Serra, M., et al. (2006). J. Neurochem. 98, 122-133.
Shamseddeen, W., et al. (2011). J. Am. Acad. Child Adolesc. Psychiatry 50, 293-301.
Tallarida, R. J., and Murray, R. B. (1987). Manual of Pharmacologic Calculations with Computer Programs, 2nd Edn. New York, N.Y.: Springer.
Uzunova, V., et al. (2006). Psychopharmacology 186, 351-361.
Uzunova, V., et al. (1998). Proc. Natl. Acad. Sci. 95, 3239-3244.
Valzelli, L. (1969). "Aggressive behavior induced by isolation," in Aggressive Behavior, eds S. Garattini and S. B. Sigg (Amsterdam: Excerpta Medica Foundation), 70-76.
van Broekhoven, F., and Verkes, R. J. (2003). Psychopharmacology 165, 97-110.
Volpi-Abadie, J., Kaye, A. M., and Kaye, A. D. (2013). Ochsner J. 13, 533-540.
Walderhaug, E., et al. (2010). Pharmacopsychiatry 43, 45-49.
Westenberg, H. G. (1996). J. Affect Disord. 40, 85-93.
Whiteford, H. A., et al. (2013). Lancet 382, 1575-1586.
Wiersma, J. E., et al. (2009). J. Clin. Psychiatry 70, 983-989.
Williams, L. M., et al. (2016). Transl. Psychiatry 6:e799.
Willner, P., et al. (2013). Biobehav. Rev. 37(10 Pt 1), 2331-2371.
Zhang, L. M., et al. (2014). Int. J. Neuropsychopharmacol. 17, 1659-1669.
Zlotnick, C., et al. (1997). J. Consult. Clin. Psychol. 65, 333-336.

Example 2

Introduction.

Figure 7:
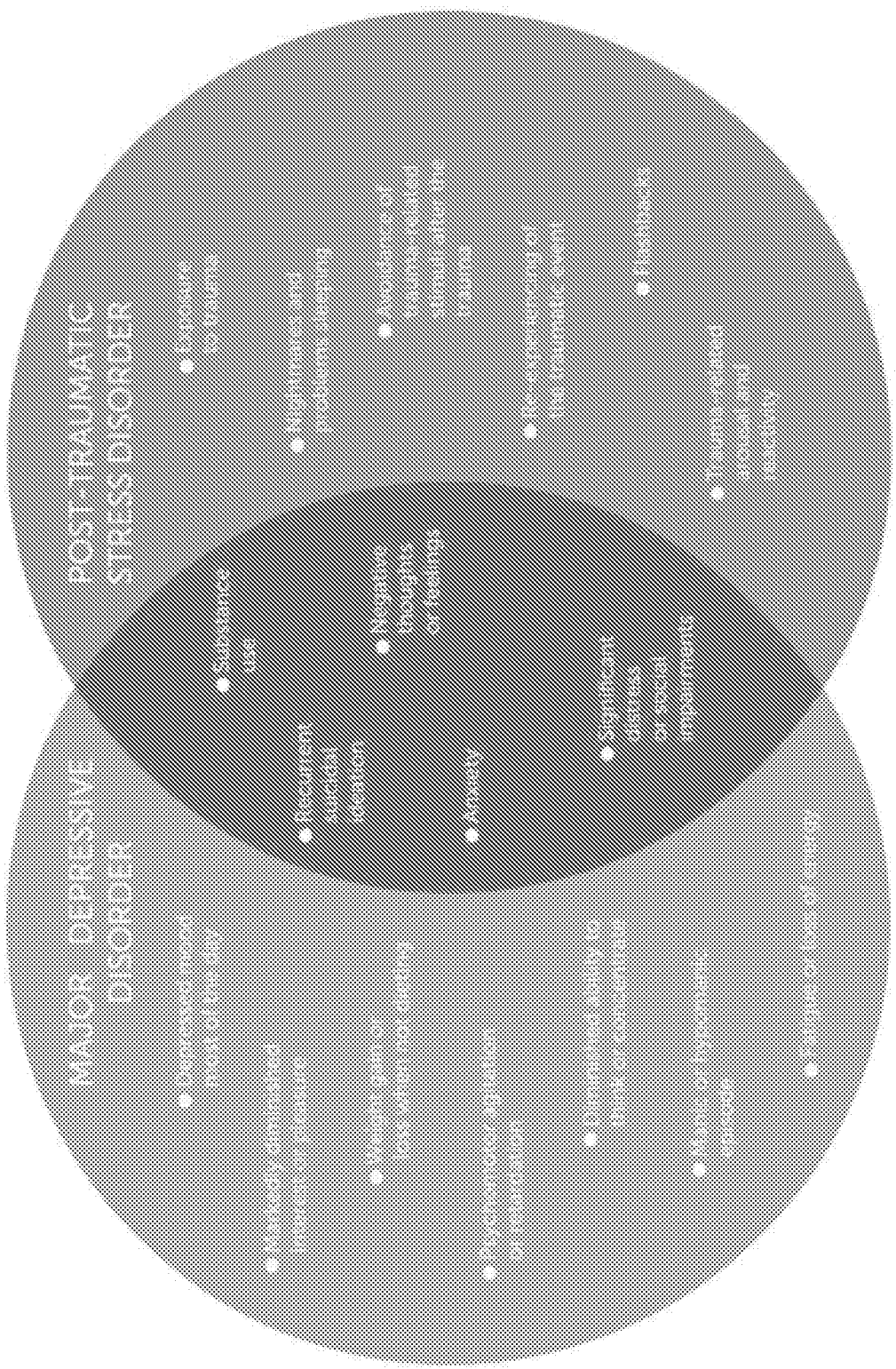
FIG. 7 shows a schematic that can demonstrate symptoms of MDD and PTSD as described by DSM-5. The DSM-5 describes the criteria to diagnose psychiatric disorders such as MDD and PTSD. The left blue circle lists the core symptoms of MDD, while, the right circle lists the core symptoms of PTSD. The intersection represents the shared symptoms of these two disorders.

The ability to cope with stress and negative life experience is an essential survival function not only in humans, but in all living organisms. Environmental factors play a role in the development of behavioral alterations. The ability to adapt to changed environmental conditions or the lack thereof, could play a key role in the onset of mood disorders. While adversities are very frequent during the lifetime of an individual, ranging from 50% to 84% in the general population [1, 2], the majority of people are resilient to adverse life events [3] but still, a large portion (about 10%) fails to develop resilience, and instead develop mood disorders such as major depressive disorder (MDD) and/or post-traumatic stress disorder (PTSD) [4]. MDD and PTSD have been dramatically increasing in the past decade [5]. Depression is a profound multifaceted neurobiological disorder of mood and emotions, which is often the result of different psychological stressors. It has a prevalence of 8-12% [6], and is the cause of impairment in different neuropsychological functions, like attention, learning and memory [7]. The DSM-5 describes a multitude of symptoms for MDD, including sadness, anhedonia, disturbed concentration, significant changes in body weight (loss or gain), that highlight the complexity of this neuropsychopathology [8]. PTSD is a stress-induced psychiatric disorder that emerges in individuals after the exposure to a trauma and is characterized by an altered ability to cope with stress. The core symptoms of this psychiatric disorder are re-experiencing symptoms, nightmares about the trauma, changes in arousal and reactivity, avoidance of trauma-related reminders and alterations of mood [8]. PTSD and MDD share numerous overlapping symptoms and comorbidity and often MDD symptoms in PTSD patients are a progression of the disorder [9]. Both PTSD and MDD are characterized by high incidence of suicidality with a prevalence of 9.5% of patients with MDD that attempted suicide over an 18 month period [10]. Predictors for suicide in MDD patients are the male gender, family history of psychiatric disorders, more serious depressive symptoms and comorbidity with other disorders, such as anxiety spectrum disorders and substance use disorder (SUD) [11]. The core and overlapping symptoms of MDD and PTSD are presented in FIG. 7.

Moreover, both of these pathologies show a gender-related dimorphism with females more affected than males [12, 13]. In both PTSD and MDD, the prevalence in women is more than double that observed in males [14] pointing to a role of sexual hormones in the development and maintenance of the disorder. While, imbalance in sexual hormones synthesis could play an important role, they cannot explain the basic psychobiological mechanisms. Recently, it has become clearer that the convergence of multiple factors, such as biological aspects and socio-psychological environmental conditions, play a role in MDD and PTSD [15, 16, 17, 18]. Likewise, a multiplicity of factors, including genetic vulnerability, immunological alterations, epigenetic mechanisms, neurohormones, neurotransmitter systems, neuropeptides and endocannabinoids and their receptors, seem to play a role both in the manifestation and the maintenance of mood disorders.

Despite advances in the neurobiological and pathophysiological aspects, the current diagnosis for MDD and PTSD is based on patients' self-reported interviews and on the clinician's observation. These methods to diagnose psychiatric disorders is quite subjective and far from optimal because of the consistent heterogeneity not only of the symptoms, but also of the etiology [19]. Furthermore, patients with mood disorders frequently are not able to adequately characterize the symptoms of the pathology [20] and the scoring systems are often discordant [21]. Thus, it becomes urgent to develop objective biological diagnostic tools based on neurobiological deficits to obtain early diagnosis, monitor individuals at risk, instruct individualized treatments, follow-up on treatment success and possibly prevent future relapse [22, 23]. This may bring a disruption in the diagnosis of psychiatric disorders as we know of, based on symptoms characterized by the DSM-5 to regroup disorders based on their neurobiological characteristics. The progress in the diagnosis and treatment of psychiatric disorders based on biomarker assessment, rather than by symptoms classification, is long needed. Contrary to other neuroscience fields, such as the neurodegenerative disorders, progress in the assessment of valid biomarkers has been rather slow [24].

This Example discusses several biomarkers in PTSD and MDD. Tests can provide a useful tool for treatment and patient selection and to monitor treatment outcomes; ensuring patients receive the most appropriate and efficient treatment for a better chance to promptly recover.

Mood Disorders and Biomarkers.

The identification of biomarkers in clinical psychiatry can give a measurable indicator of the neurobiological condition of an individual independent of a DSM-5-based diagnosis, of its predisposition to develop psychiatric disorders or the current presence of a behavioral dysfunction. A genetic predisposition for PTSD or MDD has been shown in familial or twin studies [25], which highlights the role of genetic polymorphisms in some psychiatric disorders. In particular, some polymorphisms of the dopaminergic and serotoninergic circuits have been found. A polymorphism for the dopamine D2 receptor seems to contribute to PTSD predisposition [26], while, the serotonin transport gene is linked with more depressive symptoms and suicidal ideations [27]. Furthermore, a functional polymorphism of the BDNF gene has been associated with deficient hippocampal cognitive function [28], and a polymorphism in 5α-reductase type 2 informed susceptibility for PTSD or depressive symptoms during pregnancy [29].

Figure 8:
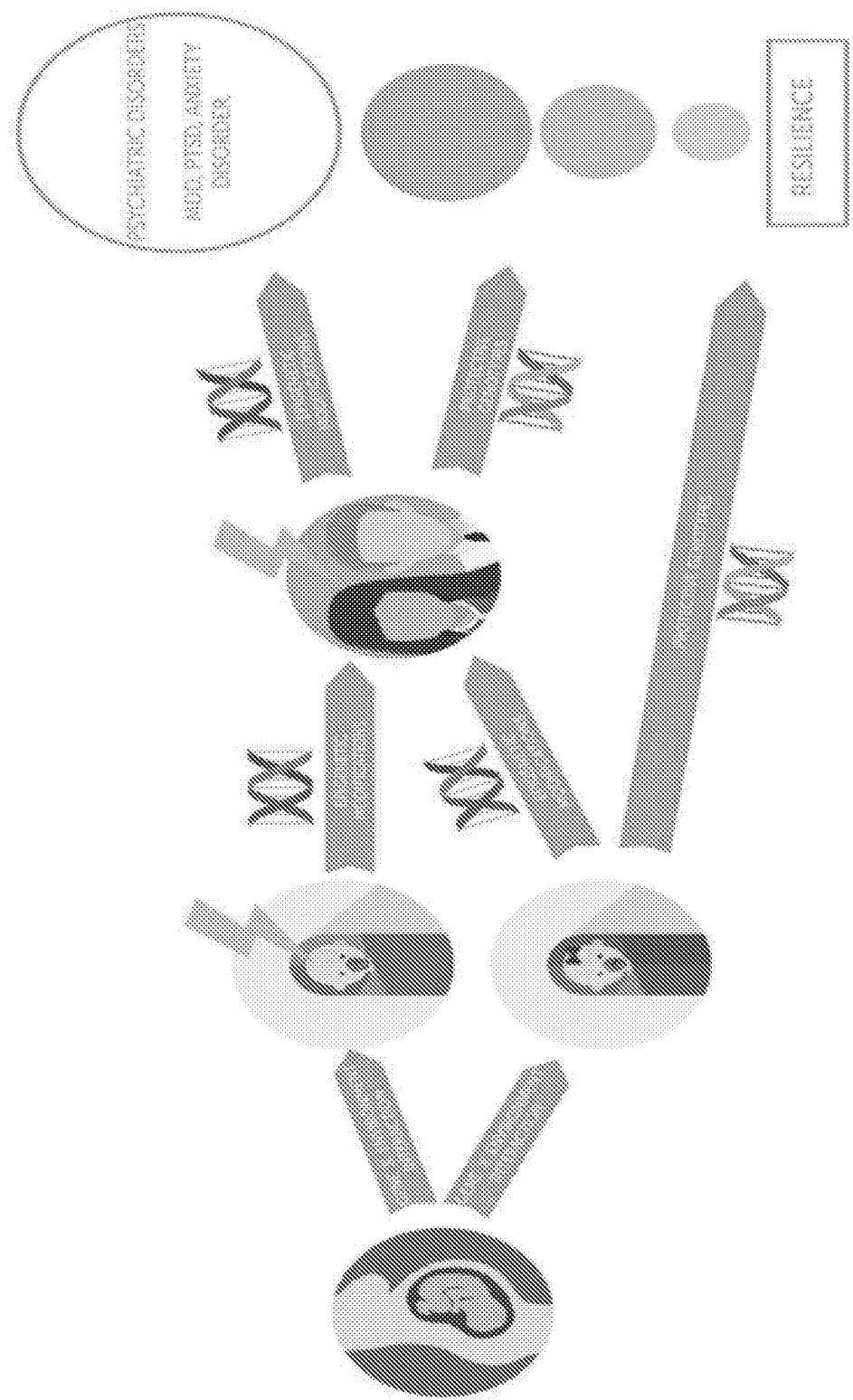
FIG. 8 shows a representation of genomic and epigentic roles in the development of neuropsychiatric disorders. The early life experiences, particularly early life adversities, may lead to epigenetic alterations. In absence of traumas and stressful conditions there is an increased possibility of developing resilience in adult life. The exposure to early life adversities in childhood may result in a phenotype that is more susceptible to psychiatric disorders following a more recent exposure to a stressor. Nevertheless, even trauma-exposed adults who have not experienced adversities during early life may develop PTSD or MDD.

In PTSD and MDD, exposure to a trauma can epigenetically impact neuronal function and affect the physiological and the behavioral mechanisms of stress adaptation [30]. Understanding the genetic vulnerability of factors that contribute to psychiatric illness may enable identification of individuals which fail to cope with traumatic events. For instance, the exposure to early-life traumas is very frequent in the psychiatric patients' history [31, 32]. During childhood, the programming of the neurobiological system and the most relevant epigenetic alterations take place [33]. Thus, an early adverse experience, like child abuse and neglect, dramatically enhance an individual predisposition to develop depression or other psychiatric disorders later in life. Trauma clearly induces epigenetic changes with short- and long-term effects on neuronal function, brain plasticity and behavioral modifications [30, 34, 35]. Epigenetic alterations can be reversible and are potential biomarker candidates for the development of new treatments for psychiatric disorders, as demonstrated by studies in rodents [36] (depicted in FIG. 8).

One of the principal neuronal deficits, which was firstly pointed as a primary deficit in depression was the serotoninergic neurotransmission although this hypothesis has never found to be convincing scientific evidence [37]. A fundamental evidence for the original hypothesis of serotonin's role in depression is derived from the mechanism of tricyclic antidepressant (TCA) on the reuptake of serotonin. This gave rise to develop a number of antidepressants, such as the selective serotonin reuptake inhibitors (SSRIs), which can enhance the activity of serotonin in depressed patients' brain, improving their depressive symptoms [38,39]. However, SSRIs only help 50% of MDD and PTSD patients [40] and this result highlights that more and better biomarkers need to be discovered. Given PTSD and MDD are multifactorial disorders, it is important to assess a number of other biomarkers and treatment targets so that patients can be classified based on their specific biochemical deficits. Furthermore, this could lead to stratification in patients' population that allows the design of better clinical trials and, later, the design of better treatments. Therefore, if a patient has a deficit in a specific neuroactive steroid level, the possible therapy will supplement that neuroactive steroid or its surrogate but will not provide a serotonergic molecule that may not help and may only result in unwanted side effects.

In the previous years, biomarker discovery for MDD and PTSD has suggested a number of neurochemical deficits in preclinical and clinical settings, including HPA alterations in response to stress, variations of immune response or signaling and dysregulation of the endocannabinoid and neurosteroid systems, which will be examined in further details herein.

Biomarkers in PTSD and MDD.

Chronic Stress and HPA Axis Role.

Aside from a genetic vulnerability, one of the major causes of depression is exposure to chronic stress. Prolonged stress leads to alteration of behavior and physiology of both humans and rodent models of depression [41, 42]. The stress response is mediated by the hypothalamus-pituitary-adrenal (HPA) axis; the role of this axis in MDD and PTSD has been demonstrated [43]. Alterations of the corticotropin-releasing hormone (CRH) function have been reported and enhanced levels of CRH have been found in the cerebrospinal fluid (CSF) of depressed patients [44]. The increased release of CRH results in a greater secretion of adrenocorticotropic hormone (ACTH) and in increased glucocorticoids synthesis, in particular cortisol, which has an inhibitory feedback on CRH and ACTH through the glucocorticoid receptor (GR) and the mineralocorticoid receptor (MR). Of note, patients with MDD and PTSD show enhanced levels of cortisol in saliva, plasma and urine, and an increased size and activity of pituitary and adrenal glands [45]. The receptor subtype for CRH, CRHR1, seems to have important effects on anxiety and depression, even if the results are somewhat inconclusive [46]. Papiol and colleagues found a SNP in the CRHR1 gene, rs 110402, and showed that homozygous patients for TT in this SNP present an earlier onset of the disease than other patients [47].

Several studies investigated the possible alteration of the HPA axis by stimulating the GR by the administration of the synthetic glucocorticoid, dexamethasone (dex). They demonstrated that depressed patients fail to show a negative feedback induced by an oral dose of dex; while, in healthy individual, a low dose of dex leads to an inhibition of the HPA axis and to decreased cortisol levels for up to 24 hours [48, 49, 50, 51]. Nevertheless, the glucocorticoid system is a potential target for MDD and PTSD therapeutics. For example, GR sensitivity is regulated by FKA binding protein 51 (FKBP5) and depressed patients exhibit decreased GR sensitivity with a substantial reduction of FKBP5 mRNA expression. The FKBP5 gene transcription is dependent on GR activation with a feedback modulation that regulates GR sensitivity. After an administration of dex, depressed patients showed a GR-mediated alteration in gene expression compared with healthy controls [52]. However, the FKBP5 gene appears to play a primary role in psychiatric pathologies. For example, polymorphisms associated with early traumatic events, like childhood abuse, predict adult major depression and PTSD [53]. A study of Binder and colleagues revealed that 3 polymorphisms of this gene are significantly associated with an enhanced FKBP5 expression, which regulates the HPA axis functionality. Patients with these polymorphisms show less hyperactivity of the axis during depression and, specifically rs1360780 was strongly associated with antidepressant effects in patients with a slower response in homozygotes [54].

The interaction between early traumas and polymorphisms determines the methylation state of the gene and regulates the sensitivity of FKBP5 to GR regulation [55]. Remarkably, the severity of PTSD is associated with the level of FKBP5 gene expression; low expression of this gene is linked to low plasma cortisol [56]. Of note, adversities during childhood influence the transcriptional activity and the state of the HPA axis genes implicated in the response to stress. Moreover, the onset of PTSD after trauma exposure is associated with pre-traumatic biomarkers, which reveal the level of sensitivity to stress [57].

Two possible stable epigenetic biomarkers for PTSD: GR and the FKBP5 gene methylation were observed. The different methylation of these genes is associated, respectively, with prognosis and with symptom severity. The GR exon 1F promoter methylation predicted the outcome of the treatment, while, the cytosine methylation of FKBP5 promoter seemed to be associated with recovery [58]. GR gene methylation does not change over time signifying that early environmental experiences cause a durable epigenetic modification of this gene [59]. In animal studies, it is clear that variations in maternal care leads to a different methylation pattern of GR gene with lasting effects on GR responsiveness in adults [60]. In humans, child abuse is linked to enhanced methylation of GR exon 1F promoter in leukocytes and in the hippocampus obtained post-mortem [61]. Thus, the GR promoter methylation in hippocampus seems to be affected by maternal care, which may alter the inhibiting feedback regulation of glucocorticoids on CRF expression and on HPA axis ability to cope with stressors [62].

The early-life experiences have a strong impact on gene expression and adversity during the early phase can influence both GR and FKBP5 methylation. In PTSD, the GR promoter methylation induces an enhanced GR sensitivity with low levels of glucocorticoids, which decrease FKBP5 gene expression. This diminished FKBP5 gene expression could sustain the increased sensitivity of GR. Thus, the methylation of the FKBP5 promoter leads to an increase of this gene expression and, consequently, to a reduced GR sensitivity. Coincidently, patients who respond to treatment show a decrease methylation of the FKBP5 promoter and of GR sensitivity.

Methylation or demethylation of a number of other genes and their expression patterns are due to glucocorticoids effects. This includes genes linked to the synthesis of the brain-derived neurotrophic factor (BDNF), which affects neurogenesis, of neuropeptides, such as neuropeptide Y and α-MSH, or of enzymes involved in biosynthesis of neurohormones, such as the GABAergic neuroactive steroids [63, 64, 65].

The Immune System Modulation of Stress Response.

The HPA axis and the immune systems are interconnected; however, it is poorly understood or research how they regulate each other in PTSD and MDD. Some preclinical research highlights the role of immune factors, such as pro-inflammatory cytokines (interleukin IL-6, IL-1 and TNF-α) in the regulation of memory and neurogenesis, and their interaction with glutamate and GABA signaling or changes in long term potentiation (LTP) [66, 67].

The most promising inflammatory biomarkers in serum of subjects with psychiatric disorders are pentraxin C-reactive protein (CRP), tumor necrosis factor alpha (TNF-α), and IL-1 and IL-6 [68]. CRP, an acute-phase protein produced by the liver, is found in plasma in response to inflammation, and could be an important biomarker for psychiatric disorders, in addition to participating in inflammatory processes [69]. An increased CRP level was shown in patients with PTSD or in suicidal patients [70, 71]. Some recent studies showed that patients with CRP levels above 10 mg/l responded better to treatment with TCAs or SSRIs than to psychotherapy [72] and that patient with low CRP levels (<1 mg/l) showed more consistent treatment response to escitalopram than to nortriptyline [73]. Taken together, these findings suggest that CRP may be an intriguing predictor of treatment outcomes that could lead to a personalized treatment approach.

In depressed patients, an increased level of plasma CRP and IL-6 [74], and the serum or plasma levels of IL-1β and IL-6 are often related to antidepressant treatment, given that their levels inversely correlated with treatment response [75].

The investigation of mRNA levels of cytokines in MDD patients showed an increase of several inflammatory factors, such as IL-1β, IL-6 and TNF-α. Furthermore, two SNPs of IL-1β gene, rs16944 and rs1143643, were strongly associated with decreased responsiveness to antidepressants and the fMRI-analysis showed reduced amygdala hyperactivity to emotional stimuli [76]. A SNP was also discovered for the IL-6 gene, rs1800795, which is associated with enhanced levels of plasma IL-6. Furthermore, its interaction with additional stressors increases the risk of MDD development [77, 78].

A study by Sukoff Rizzo and colleagues, in rodents, demonstrated that an increased IL-6 level in the brain results in development of depressive-like behavior and the activation of IL-6, inhibits the antidepressant effect of SSRIs [79]. This finding may explain why some antidepressants fail to induce beneficial pharmacological effects in patients with MDD and PTSD.

Another cytokine that is increased in the plasma of depressed patients is TNF-α, and failure to normalize its levels also correlated with failed response to SSRIs [80, 81]. In particular, recent studies suggested that responders to antidepressants showed a lower expression of TNF-α. Lower expression of this cytokine (30%) was observed after successful treatment with escitalopram [82]. These findings collectively suggest that pro-inflammatory markers may be more useful to predict treatment outcomes rather than for diagnosis of the pathology. Whether the enhancement of pro-inflammatory markers reflects a neural dysfunction or whether these molecules play a role in the pathogenesis of psychiatric disorders is unclear, however, their alteration may be used as a marker to determine the most appropriate treatment. The complex interconnection between the immune and the neuroendocrine systems allows an appropriate adaptive reaction to a variety of stressors with a logical role in the development of the disorder.

Neuroplasticity.

PTSD and MDD are associated with low levels of neurotrophins, like BDNF, which play a fundamental role in neuronal growth, synaptic maturation and plasticity [83]. Hence, BDNF is fundamental for the development of the nervous system and decreased serum levels of this neurotrophin and/or of its receptor, TrkB, may be a useful predictor for dysfunctional behavior and in particular for suicidal ideations [70]. Studies in rodent models show a decreased BDNF mRNA expression in the hippocampus during chronic and acute stress, with a consequent effects on hippocampal neurogenesis [84]. The reduction of BDNF mRNA expression has been associated with increased IL-6 expression [85]. Importantly, both glucocorticoids and pro-inflammatory cytokines have been often linked to a reduction of BDNF levels and to a diminished neurogenesis resulting in dendritic atrophy [86, 87]. The mechanism by which pro-inflammatory cytokines could affect BDNF expression is still unclear. However, animal studies showed that IL-1β down-regulates BDNF expression in rat hippocampus, probably by an indirect mechanism that relates to regulation of glucocorticoids [88].

Depressed patients show a reduction of BDNF mRNA expression, with increased levels that correlated with symptom improvement in antidepressant-responders [89]. A recent meta-analysis investigation has suggested that BDNF is a promising biomarker for MDD patients relevant to predict clinical improvement [90].

Contrary to what is observed in MDD patients, the BDNF levels in the serum of subjects with PTSD are controversial. Some researchers reported that it increases in PTSD and it is even higher after traumatic events [91], while others showed lower levels [92]. Berger and colleagues found that serum BDNF level is a good predictor of the treatment outcome in PTSD: lower serum BDNF is a good marker for an appropriate response to escitalopram in patients. They explained this apparent contradictory result, discussing the role of BDNF in the mesolimbic dopamine pathway, where high levels of this neurotrophin is necessary to maintain, in mice, social avoidance behavior, which is a fundamental symptom of PTSD in humans. So, the inhibition of BDNF activity could have mood-regulatory activity in some animal models, which suggests a biphasic concentration-dependent activity of BDNF [93].

Polymorphisms of the BDNF gene have also been investigated, the rs6265, resulting from a substitution of Val66Met, is frequently linked to a higher risk of developing affective disorders [94, 95]. This SNP influences hippocampal volume and memory and seems to increase the susceptibility to both depression and PTSD [96]. Furthermore, the frequency of Met is two times higher in PTSD patients than in healthy control [97]. Stress and Met-allele seem to interact; a study of healthy European volunteers suggested that this interaction can result in developing depression and anxiety [98].

The NPY implications in Resilience. An important mediator in the regulation of the stress responses is the neuropeptide Y (NPY) [99]. NPY and its receptors play a fundamental role in the response to stressors and a decreased fear, anxiety, and also improve memory processes [100, 101]. NPY participates in the regulation of HPA axis by interacting with the paraventricular nucleus (PVN) of the hypothalamus and with the action of CRH [102]. Stimulation of NPY Y1 receptors in the hippocampus of rodents appears to inhibit the HPA axis, although some studies have reported different results [103, 104, 105]. Evidence demonstrates that NPY is relevant in PTSD and MDD pathophysiology. Clinical studies showed that NPY concentration in the CSF and plasma is reduced in patients with PTSD [106, 107, 108]. In particular, a study by Ramusson et al. showed a lowered level of plasma NPY in PTSD subjects, but NPY level was also reduced in combat-exposed individuals without PTSD, showing that the trauma itself alters NPY concentration [107]. However, later studies observed opposite results, showing both trauma-exposed PTSD patients with no alterations of NPY levels [109] and combatexposed veterans without PTSD with a higher NPY expression [110]. Sah and colleagues showed that combat-exposed veterans with PTSD have lower NPY levels in the CSF in comparison to trauma-exposed veterans without PTSD [108]. Thus, the abnormalities in NPY concentrations are of interest because NPY seems to promote resilience and prevent the development of trauma-induced PTSD. Genetic evidence supports this role of NPY: Individuals with low expression of NPY genotype present exaggerated amygdala reactivity, which reflects an over-reaction to stress [111]. However, direct associations between NPY gene polymorphisms with PTSD have not been observed. Several SNPs of the NPY gene have been studied and the most promising is rs16147 for its role in stress responsiveness. The NPY SNP rs16147 is highly related to the variation of the NPY levels and is associated with a reduction of NPY expression [111]. Thus, NPY could have therapeutic implications, because it is stress-related, linked to trauma exposure, and it could facilitate resilience decreasing the possibility to develop PTSD [112].

The Role of Endocannabinoids and Allopregnanolone in MDD and PTSD.

The biosynthesis of Neuroactive Steroids. Neurosteroids, allopregnanolone (Allo) and its stereoisomer, pregnanolone (PA), are synthesized in glutamatergic corticolimbic neurons, including cortical and hippocampal pyramidal neurons, and pyramidallike neurons of the basolateral amygdala [113, 114]. They rapidly modulate neuronal excitability by acting as potent positive allosteric modulators of the action of GABA at GABAA receptors and they are responsible for the fine-tuning of the receptor for GABAmimetic, agonists and positive allosteric modulators [115, 116, 117, 118]. Recent finding in the field have suggested that the sulfated congeners of these neurosteroids, e.g., PA sulfate, act as inhibitors of tonic rather than phasic NMDA-mediated neurotransmission [119].

Downregulation of neurosteroid biosynthesis, which includes Allo and PA levels and their biosynthetic enzyme 5α-reductase type I and 3α-hydroxisteroid dehydrogenesis (3α-HSD), are strongly associated with major depression and PTSD (for a review please see [120, 121]). Specifically, patients with depression show serum, plasma, CSF, and brain reductions of Allo levels and/or biosynthesis [122, 123, 124, 125]. Likewise, depression and anxiety symptoms in both anorexic and obese females or during pregnancy and postpartum are associated with downregulated Allo levels [126, 127]. The levels of Allo in the CSF are 40-60% decreased in patients with unipolar major depression and premenopausal women with PTSD [124]. The lowest levels were found in the PTSD patients with comorbid depression [128]. Altered Allo levels have been observed both in serum and CSF in several other neuropathologies, including postpartum depression and drug addiction [124, 129]. Women with PTSD show lower Allo concentration in the CSF and serum, while progesterone and the immediate Allo precursor, 5α-DHP fail to change, pointing to a possible deficit in the enzyme 3α-HSD [130]. Likewise, in PTSD males, the CSF Allo levels decrease. Without being bound by theory, this may be due to deficits of 5α-reductase type 1, and were negatively correlated with PTSD symptoms [131]. Moreover, a SNP in the 5α-reductase type II gene is linked to enhanced risk for PTSD in men [132]. 5α-reductase type 2 is preferentially expressed in the periphery in the adrenal cortex [133], however, peripheral GABAergic neuroactive steroids, including THDOC are changed during stress and may access and influence corticolimbic circuitry [134]. Thus, the concentration and, in particular, the ratio of Allo with other neuroactive steroids levels and deficits in the enzymatic pathway may unveil sex-related biomarkers for PTSD and MDD as well as therapeutic properties in MDD and PTSD patients. Studies in depressed patients with low Allo concentrations in CSF and plasma showed that after SSRI treatment, increased Allo level correlated with improvement of depressive symptoms [123, 124].

The plasma levels of the $GABA_A$ antagonist and neuroactive steroids, dehydroepiandrosterone (DHEA) and its sulfate derivatives, DHEA sulfate (DHEAS) are currently being investigated as potential biomarkers for anxiety, MDD and PTSD. DHEA facilitated excitatory NMDA receptor function and plays a role in the inactivation of cortisol in its metabolite cortisone [135]. The DHEAS concentration and the ratio DHEAS to cortisol seems to predict the severity of symptoms of PTSD and depression in patients [136]. In the CSF of women with PTSD, correlation between the ratio of DHEA to Allo levels and their symptoms was observed [128]. This suggests a role in the balance between excitatory and inhibitory neurotransmission and the severity of the pathology.

In mouse models of depression, induced by protracted social isolation stress, a downregulation of Allo levels in corticolimbic neurons was observed and resulted from a decreased expression of 5α-reductase type I [137]. Furthermore, socially isolated (SI) mice show increased aggression, anxiety-like behavior and exaggerated contextual fear responses [138, 139]. In another model of PTSD, the single prolonged stress (SPS) mouse, downregulated cortical Allo levels was associated with enhanced anxiety-like behavior and enhanced contextual fear responses. Importantly, like in PTSD patients [140], stress in SI mice induces changes in $GABA_A$ receptor subunit composition with increased expression of α4 and δ subunits [129] that are: 1) mainly expressed in the extra-synaptic $GABA_A$ receptor, 2) show an increased sensitivity for neurosteroids, and, importantly, 3) fail to bind benzodiazepines, and therefore result in inefficacy to respond to their pharmacological action. These findings are strikingly consistent with dysfunctions observed in PTSD patients. PET studies show PTSD patients have decreased benzodiazepine binding sites and lack of response to benzodiazepines [140]. Collectively, PTSD like MDD shows a sex-related downregulation of Allo biosynthesis, however, this and its interface with changes in GABAA receptor subunit expression and lack of response to benzodiazepines points to a biomarker axis (FIG. 9), which may be specific for PTSD (discussed in [120]).

In SI mice, administration of Allo or its analogs (ganaxolone, BR351 and BR297) reduces behavioral dysfunction [120, 141]. Furthermore, SSRIs given at low non-serotonergic doses, act as selective brain steroidogenic stimulants (SBSSs), up-regulate Allo levels and improve fear responses, anxiety-like behavior and aggression in Allo-deficient SI mice [142]. Likewise, the 18 kDa translocator protein (TSPO), which gates the entry of cholesterol from the cytosol into the inner mitochondrial membrane to initiate neurosteroidogenesis, resulted in a useful PTSD therapeutic target [143]. Drugs that act at TSPO stimulate downstream Allo levels in the brain of SPS mice and rescue behavioral dysfunctions [144]. In recent clinical trials, allopregnanolone (brexanolone) efficacy against symptoms of postpartum depression (PPD) was superior to that of placebo [145]. PPD patients who received intravenous infusions of allopregnanolone showed a rapid and long lasting remission of depressive symptoms in 70% of treated vs only 9% of placebotreated patients.

The Endocannabinoid System.

The endocannabinoid system (eCBS) is involved in HPA activation and its interaction with glucocorticoids is useful to cope with stress. Furthermore, the endocannabinoids (eCBs) modulate fear memory and other memory processes, like reconsolidation and extinction, which are a core feature of PTSD [146]. In a mouse model of depression, the hippocampal suppression of the eCB signaling leads to depressive-like behavior [147, 148], thus suggesting it may play a role in PTSD and MDD.

The endocannabinoid receptor type 1 (CB1) has received growing attention in mood disorders. A positron emission tomography study showed enhanced expression in individuals with PTSD but not in trauma-exposed healthy controls [149]. Furthermore, this study found diminished peripheral level of the endocannabinoid, anandamide (AEA), which suggest that the enhanced CB1 receptor expression, and probably sensitivity, may be in part due to lower levels of AEA [149]. Likewise, a post-mortem study revealed higher expression of CB1 in depressed suicide victims [150]. However, genetic studies support the hypothesis that impairment in CB1 may increase the risk to develop depression and other psychiatric pathologies. SNPs in the CB1 gene can increase the vulnerability to develop depressive episode after trauma exposure and in patients with mood disorders when the frequency of SNPs increases [151, 152]. Moreover, AEA and the congener, 2-arachidonoylglycerol (2-AG) serum concentration is lower in the plasma of depressed women than in matched control subjects [153]. These endocannabinoids in depressed women are a focus of investigation and several considerations of whether they may be valuable markers are being drawn. Rodent models of PTSD and depression show decreased levels of AEA and 2-AG [154]. Other endocannabinoids that activate the peroxisome proliferator-activated receptor alpha (PPAR-α) such as N-oleoyldopamine (OEA) and N-palmitoylethanolamine (PEA) may be involved in the pathophysiology of PTSD and MDD [155]. PPAR-α activation has been shown to mediate the responses to stressful conditions [156]. In healthy adults, PEA significantly increase in clinical stress tests in connection with an increase of cortisol levels [157]. PEA levels also when healthy subjects experience a short-term depressed mood [158]. On the other hand, PEA in PTSD, MDD, and impulsive aggression are decreased [159]. Of note, PEA adjunctive therapy to citalopram improves depressed symptoms [160] and intense physical activity increases PEA and OEA levels while improving depression and PTSD symptoms [161]. The relationship between PPAR-α and emotional regulation is further highlighted by its role as an anti-neuroinflammatory target [162, 163, 164, 165, 166].

It has been demonstrated that that stimulation of PPAR-α by PEA or synthetic agonists increased corticolimbic allopregnanolone levels in hippocampus, amygdala, and prefrontal cortex, which resulted in decreased contextual fear extinction and fear extinction retention, improved aggression and anxiety-like behavior in SI mice [120, 167]. PEA also induces antidepressant-like effects in SI mice [120]. Furthermore, this behavioral improvement by PEA or other PPAR-α synthetic agonists, which was associated with normalized allopregnanolone levels, was blunted by antagonism at PPAR-α, inhibition of allopregnanolone biosynthetic enzymes, and in PPAR-α KO mice. Other rodent studies have reported that exposure to predator stressors downregulates PEA and OEA levels (Holman et al., 2014), but elevating PEA and OEA levels results in antidepressant-like effects [168, 169, 170].

Altogether, these reports originating by preclinical and clinical studies support an emerging role of PPAR-α in MDD and PTSD. Furthermore, this new discovered interaction between PPAR-α activation and allopregnanolone levels may unveil biomarker axis uniquely altered at the interface of the endocannabinoid and the neurosteroid systems (FIG. 9).

Blood-Based Biomarker Axis.

Peripheral Biomarkers. All biomarkers discussed in this Example have been studied in animal models and in humans, with a focus on the CNS and CSF, serum and plasma [171, 172]. Noninvasive peripheral biomarkers are more useful and functional for diagnosis of disorders of mood and emotions. CSF reflects more closely the alterations of the brain but the procedure is stressful and results in pain and discomfort in the patients [173, 174]. Blood draws can also be stressful for some patients, putting at risk a precise diagnosis or may even turn patients away from testing. However, most studies are currently assessing serum- or plasma-based diagnostic tests [175], considering different biomarkers and several methods, including metabolomics (neurohormones, neuroactive steroids, endocannabinoids) or genomics and proteomics. The techniques used for the proteomics are immunoassays (ELISAs), but the mass spectrometry (MS)-coupled with 2D electrophoresis is now applied for the analysis of several proteins in biological tissues [176, 177]. While immunoassays present some limitations, principally due to large volume of sample required and limited amount of proteins that can be analyzed, the MS is making its way into proteomics as it provides unsurpassed structure selectivity. An advantage of this technique is the quantification of several biomarkers simultaneously in small samples; while, the disadvantages include very low reproducibility and the need of targeted analyses to discover a potential biomarker. In our laboratory, with the goal of assessing biomarkers, we employ the gas chromatography-mass spectrometry (GC-MS) to determine neuroactive steroids in CSF, serum and plasma of MDD and PTSD patients but also in mouse models of these disorders.

Figure 9:
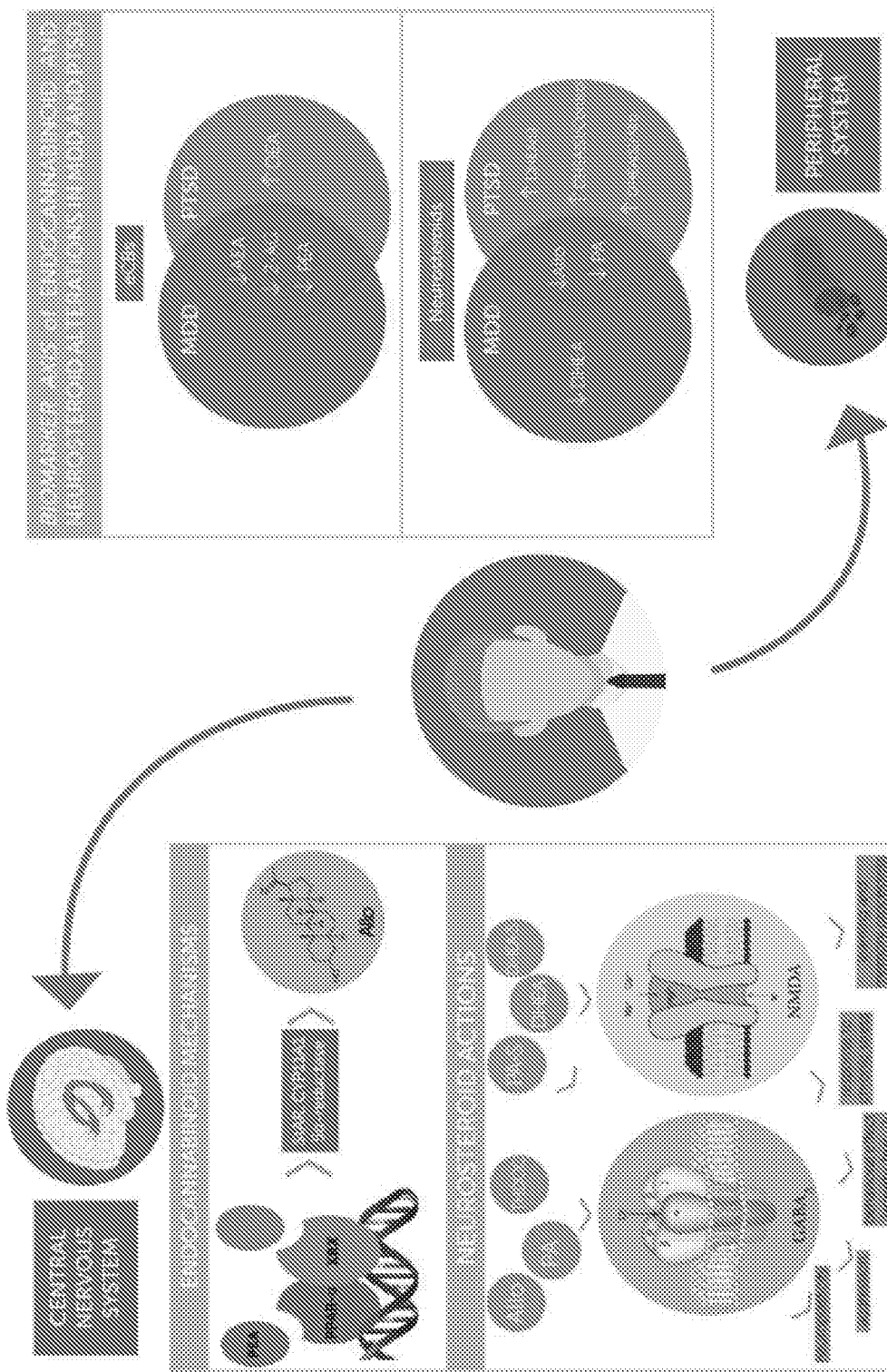
FIG. 9 shows a schematic that can demonstrate the role of endo cannabinoids and neurosteroids in a biomarker axis. The schematic representation shows the role of endocannabinoids (eCBs) and neurosteroids in the central nervous system (left panel), and their altered level in the peripheral tissue of PTSD and MDD patients (right panel). The eCBs, such as PEA and OEA activate the intracellular peroxisome proliferator-activated receptor (PPAR)-α, which heterodimerize with the retinoid X receptor (RXR). The PPAR-α and RXR complex binds to the consensus regions on the target gene promoters and initiates transcription. PEA, through the activation of PPAR-α, can enhance the induction of corticolimbic allopregnanolone (Allo) biosynthetic enzymes, including CYPIIAI and 5α-reductase, resulting in an enhanced neurosteroid synthesis (e.g., Allo). PEA levels and probably expression of PPAR-a are influenced by stress, which may negatively affect Allo's biosynthetic enzyme expression and allopregnanolone levels.

These results have identified specific changes in the axis of neuroactive steroid biosynthesis and their relation with neurotransmitter systems, including GABAA receptors [120] (FIG. 9). Several protocols that consider not one, but several biomarkers are advantageous and have been recently proposed [178, 179]. These panels provide the evaluation of several biomarkers together: for example, Papakostas and colleagues proposed a test based on neuropeptides that gives an adequate sensitivity to distinguish MDD from non-depressed subjects [180]. Other studies considered a panel of blood transcriptomic biomarkers to predict early-onset MDD [181] and to identify depressed patients in remission or predict response to therapy [179]. Transcriptomics, including FAM46A, MARCKS and RAPH1 seem to be particular promising. Evaluation of blood-based tests also showed that candidate biomarker transcripts are promising for psychiatric disorders [179, 181, 182, 183]. Also, functional genomics tests have been proposed, analysis genes involved in several functions from myelination to growth factor signaling [178].

A consistent number of studies are currently working on assessing biomarker tests for MDD and PTSD, to provide a pre-clinical screening, a precise and accurate analytical validation of the marker, and a clinical validation. The process for a test-assessment based on biomarkers, from discovery to validation, is represented in FIG. 10.

REFERENCES FOR EXAMPLE 2

1. Benjet C, Bromet E, Karam E G, et al. Psychol Med. 2016 January; 46(2):327-43.
2. Breslau N, Kessler R C, Chilcoat H D, et al. Arch Gen Psychiatry. 1998 July; 55(7):626-32.
3. Bonanno G A, Diminich E D. 2013 April; 54(4):378-401.
4. White J, Pearce J, Morrison S, et al. Epidemiol Psychiatr Sci. 2015 June; 24(3):249-57.
5. Whiteford H A, Degenhardt L, Rehm J, et al. 2010. Lancet. 2013 Nov. 9; 382(9904):1575-86.
6. Demyttenaere K, Bruffaerts R, Posada-Villa J, et al. JAMA. 2004 Jun. 2; 291(21):2581-90.
7. Snyder H R. Psychol Bull. 2013 January; 139(1):81-132.
8. American Psychiatric Association. Diagnostic and Statistical Manual of Mental Disorders. 5th ed. Washington, D.C. 2013.
9. Bleich A, Koslowsky M, Dolev A, et al. British Journal of Psychiatry. 2018; 170(5):479-482.
10. Holma K M, Haukka J, Suominen K, et al. Bipolar Disord. 2014 September; 16(6):652-61.
11. Hawton K, Casanas I C C, Haw C, et al. J Affect Disord. 2013 May; 147(1-3):17-28.
12. Kokras N, Dalla C, Sideris A C, et al. Neuropharmacology. 2012 January; 62(1):436-45.
13. Pitychoutis P M, Nakamura K, Tsonis P A, et al. Neuroscience. 2009 Apr. 10; 159(4):1216-32.
14. Breslau N. Trauma Violence Abuse. 2009 July; 10(3):198-210.
15. De Bellis M D, Thomas L A. Current Psychiatry Reports. 2003 Apr. 1; 5(2):108-117.
16. Fu Q, Heath A C, Bucholz K K, et al. Psychological Medicine. 2002; 32(1):11-24.
17. Gill J, Vythilingam M, G. P G. Journal of Traumatic Stress. 2008; 21(6):530-539.
18. Koenen K C, Fu Q J, Ertel K, et al. Journal of Affective Disorders. 105(1):109-115.
19. Gottesman, I I, Gould T D. Am J Psychiatry. 2003 April; 160(4):636-45.
20. Carter J D, Frampton C M, Mulder R T, et al. J Affect Disord. 2010 July; 124(1-2):202-6.
21. Riedel M, Moller H J, Obermeier M, et al. J Psychiatr Res. 2010 November; 44(15):1063-8.
22. Altamura A C, Buoli M, Albano A, et al. Int Clin Psychopharmacol. 2010 May; 25(3):172-9.
23. Huerta-Ramirez R, et al. J Affect Disord. 2013 Sep. 25; 150(3):1247-50.
24. Lakhan S E, Vieira K, Hamlat E. Int Arch Med. 2010 Jan. 12; 3:1.

25. Koenen K C, Harley R, Lyons M J, et al. J Nerv Ment Dis. 2002 April; 190(4):209-18.
26. Voisey J, Swagell C D, Hughes I P, et al. Depress Anxiety. 2009; 26(1):28-33.
27. Caspi A, Sugden K, Moffitt T E, et al. Science. 2003 Jul. 18; 301(5631):386-9.
28. Yulug B, et al. J Neuropsychiatry and Clinical Neurosciences. 2010; 22(1):123.e5-123.e6.
29. Hellgren C, Comasco E, Skalkidou A, et al. Hormones and Behavior. 2017
30. Zannas A S, West A E. Neuroscience. 2014 2014/04/04/; 264:157-170.
31. Meena Vythilingam, et al. American Journal of Psychiatry 2002; 159(12):2072-2080.
32. Nemeroff C B, Heim C M, Thase M E, et al. PNAS 2003; 100(24):14293-14296.
33. Teicher M H, et al. Neuroscience & Biobehavioral Reviews. 2003 2003/01/01/; 27(1):33-44
34. Provencal N, Binder E B. Curr Opin Neurobiol. 2015 February; 30:31-7.
35. Rampp C, Binder E B, Provencal N. Prog Mol Biol Transl Sci. 2014; 128:29-50.
36. Kwapis J L, Wood M A. Trends Neurosci. 2014 December; 37(12):706-20.
37. Cowen P J. Trends in Pharmacological Sciences. 2008 2008/09/01/; 29(9):433-436.
38. Anderson I M. Depress Anxiety. 1998; 7 Suppl 1:11-7.
39. Cowen P J. Pharmacol Ther. 1990; 46(1):43-51.
40. Kemp A H, Gordon E, Rush A J, et al. CNS Spectr. 2008 December; 13(12):1066-86
41. Lupien S J, McEwen B S, Gunnar M R, et al. Nat Rev Neurosci. 2009 June; 10(6):434-45.
42. Katz R J, Roth K A, Carroll B J. Neurosci Biobehav Rev. 1981 Summer; 5(2):247-51.
43. Holsboer F. Neuropsychopharmacology. 2000 November; 23(5):477-501.
44. Waters R P, Rivalan M, Bangasser D A, et al. Neurosci Biobehav Rev. 2015 November; 58:63-78.
45. Nemeroff C B, Vale W W. J Clin Psychiatry. 2005; 66 Suppl 7:5-13.
46. Koob G F, Zorrilla E P. Neuropsychopharmacology. 2012 January; 37(1):308-9.
47. Papiol S, Arias B, Gasto C, et al. J Affect Disord. 2007 December; 104(1-3):83-90.
48. Casat C D, Powell K. J Clin Psychiatry. 1988 October; 49(10):390-3.
49. Pariante C M. J Psychopharmacol. 2006 July; 20(4 Suppl):79-84.
50. Kalin N H, Cohen R M, Kraemer G W, et al. Neuroendocrinology. 1981 February; 32(2):92-5.
51. Miller A H, Spencer R L, Pulera M, et al. Biol Psychiatry. 1992 Nov. 15; 32(10):850-69.
52. Menke A, Arloth J, Putz B, et al. Neuropsychopharmacology. 2012 May; 37(6):1455-64.
53. Zannas A S, Binder E B. Genes Brain Behav. 2014 January; 13(1):25-37.
54. Binder E B, Salyakina D, Lichtner P, et al. Nat Genet. 2004 December; 36(12):1319-25.
55. Klengel T, Mehta D, Anacker C, et al. Nat Neurosci. 2013 January; 16(1):33-41.
56. Yehuda R, Cai G, Golier J A, et al. Biol Psychiatry. 2009 Oct. 1; 66(7):708-11.
57. Yehuda R. Psychiatry. 1999 February; 44(1):34-9.
58. Yehuda R, Daskalakis N P, Desarnaud F, et al. Front Psychiatry. 2013; 4:118.
59. Meaney M J, Ferguson-Smith A C. Nat Neurosci. 2010 November; 13(11):1313-8.
60. Zhang T Y, Labonte B, Wen X L, et al. Neuropsychopharmacology. 2013 January; 38(1):111-23.
61. McGowan P O, Sasaki A, D'Alessio A C, et al. Nat Neurosci. 2009 March; 12(3):342-8.
62. Hellstrom I C, et al. Philos Trans R Soc Lond B Biol Sci. 2012 Sep. 5; 367(1601):2495-510.
63. Di S, Maxson M M, Franco A, et al. J Neurosci. 2009 Jan. 14; 29(2):393-401.
64. Gourley S L, et al. Neuropsychopharmacology. 2009 February; 34(3):707-16.
65. Higuchi H, Yang H Y, Sabol S L. J Biol Chem. 1988 May 5; 263(13):6288-95.
66. Tambuyzer B R, Ponsaerts P, Nouwen E J. J Leukoc Biol. 2009 March; 85(3):352-70.
67. Yirmiya R, Goshen I. Brain Behav Immun. 2011 February; 25(2):181-213.
68. Liu Y, Ho R C, Mak A. J Affect Disord. 2012 August; 139(3):230-9.
69. Pepys M B, Rowe I F, Baltz M L. Int Rev Exp Pathol. 1985; 27:83-111.
70. Priya P K, Rajappa M, Kattimani S, et al. Clin Chim Acta. 2016 Jun. 1; 457:41-5.
71. Spitzer C, Barnow S, Volzke H, et al. J Psychiatr Res. 2010 January; 44(1):15-21.
72. Harley J, Luty S, Carter J, et al. J Psychopharmacol. 2010 April; 24(4):625-6.
73. Uher R, Tansey K E, Dew T, et al. Am J Psychiatry. 2014 Dec. 1; 171(12):1278-86.
74. Wium-Andersen M K, et al. JAMA Psychiatry. 2013 February; 70(2):176-84.
75. Hannestad J, DellaGioia N, Bloch M. Neuropsychopharmacology. 2011 November; 36(12):2452-9.
76. Baune B T, Dannlowski U, Domschke K, et al. Biol Psychiatry. 2010 Mar. 15; 67(6):543-9.
77. Kovacs D, et al. J Neural Transm (Vienna). 2016 May; 123(5):541-8.
78. Zakharyan R, Petrek M, Arakelyan A, et al. Tissue Antigens. 2012 August; 80(2):136-42.
79. Sukoff Rizzo S J, Neal S J, Hughes Z A, et al. Transl Psychiatry. 2012 Dec. 4; 2:e199.
80. Dowlati Y, Herrmann N, Swardfager W, et al. Biol Psychiatry. 2010 Mar. 1; 67(5):446-57.
81. Eller T, et al. Prog Neuropsychopharmacol Biol Psychiatry. 2008 Feb. 15; 32(2):445-50.
82. Powell T R, et al. Eur Neuropsychopharmacol. 2013 September; 23(9):1105-14.
83. Huang E J, Reichardt L F. Annu Rev Neurosci. 2001; 24:677-736.
84. Murakami S, Imbe H, Morikawa Y, et al. Neurosci Res. 2005 October; 53(2):129-39.
85. Mondelli V, Cattaneo A, Murri M B, et al. J Clin Psychiatry. 2011 December; 72(12):1677-1684.
86. Kikusui T, Ichikawa S, Mori Y. Psychoneuroendocrinology. 2009 June; 34(5):762-72.
87. Sousa N, Madeira M D, Paula-Barbosa M M. Brain Res. 1998 Jun. 1; 794(2):199-210.
88. Barbany G, Persson H. Eur J Neurosci. 1992; 4(5):396-403.
89. Cattaneo A, et al. Int J Neuropsychopharmacol. 2010 February; 13(1):103-8.
90. Fernandes B S, Berk M, Turck C W, et al. Mol Psychiatry. 2014 July; 19(7):750-1.
91. Hauck S, et al. Progress in Neuro-Psychopharmacology and Biological Psychiatry. 2010
92. Dell'Osso L, et al. Progress in Neuro-Psychopharmacology and Biological Psychiatry. 2009 2009/08/01/; 33(5):899-902.

93. Berger W, et al. Prog Neuropsychopharmacol Biol Psychiatry. 2010 Oct. 1; 34(7):1279-84.
94. Lisiecka D M, O'Hanlon E, Fagan A J, et al. J Affect Disord. 2015 Sep. 15; 184:239-44.
95. Notaras M, Hill R, van den Buuse M. Mol Psychiatry. 2015 August; 20(8):916-30.
96. Brooks S J, Nilsson E K, Jacobsson J A, et al. PLoS One. 2014; 9(1):e82707.
97. Harrisberger F, et al. Neuroscience & Biobehavioral Reviews. 2014 2014/05/01/; 42:267-278.
98. Gatt J M, Nemeroff C B, Dobson-Stone C, et al. Mol Psychiatry. 2009 July; 14(7):681-95.
99. Hassan A M, Jain P, Reichmann F, et al. Front Behav Neurosci. 2014; 8:386.
100. Heilig M. Neuropeptides. 2004 August; 38(4):213-24.
101. Thorsell A, Carlsson K, Ekman R, et al. Neuroreport. 1999 Sep. 29; 10(14):3003-7.
102. Cavagnini F, et al. Int J Obes Relat Metab Disord. 2000 June; 24 Suppl 2:S77-9.
103. Baldock P A, Lin S, Zhang L, et al. J Bone Miner Res. 2014 October; 29(10):2238-49.
104. Bertocchi I, et al. Proc Natl Acad Sci USA. 2011 Nov. 29; 108(48):19395-400.
105. Schmidt M V, Liebl C, Sterlemann V, et al. J Endocrinol. 2008 May; 197(2):421-7.
106. Morgan C A, 3rd, Wang S, Southwick S M, et al. Biol Psychiatry. 2000 May 15; 47(10):902-9.
107. Rasmusson A M, Hauger R L, Morgan C A, et al. Biol Psychiatry. 2000 Mar. 15; 47(6):526-39.
108. Sah R, et al. Psychoneuroendocrinology. 2014 February; 40:277-83.
109. Nishi D, Hashimoto K, Noguchi H, et al. Neurosci Res. 2014 June; 83:8-12.
110. Yehuda R, Brand S, Yang R K. Biol Psychiatry. 2006 Apr. 1; 59(7):660-3.
111. Zhou Z, Zhu G, Hariri A R, et al. Nature. 2008 Apr. 24; 452(7190):997-1001.
112. Brothers S P, Wahlestedt C. EMBO Mol Med. 2010 November; 2(11):429-39.
113. Agis-Balboa R C, et al. Proc Natl Acad Sci USA. 2006 Sep. 26; 103(39):14602-7.
114. Baulieu E E, Robel P. J Steroid Biochem Mol Biol. 1990 Nov. 20; 37(3):395-403.
115. Belelli D, Peden D R, Rosahl T W, et al. J Neurosci. 2005 Dec. 14; 25(50):11513-20.
116. Pinna G, Uzunova V, Matsumoto K, et al. Neuropharmacology. 2000 Jan. 28; 39(3):440-8.
117. He J, Hoffman S W, Stein D G. Restor Neurol Neurosci. 2004; 22(1):19-31.
118. Smith S S, Waterhouse B D, Chapin J K, et al. Brain Research. 1987
119. Vyklicky V, Smejkalova T, Krausova B, et al. J Neurosci. 2016 Feb. 17; 36(7):2161-75.
120. Locci A, Pinna G. British Journal of Pharmacology. 2017; 174(19):3226-3241.
121. Zorumski C F, Mennerick S. JAMA Psychiatry. 2013 July; 70(7):659-60.
122. Agis-Balboa R C, Fischer A. Cell Mol Life Sci. 2014 January; 71(1):21-42.
123. Romeo E, Strohle A, Spalletta G, et al. American Journal of Psychiatry.
124. Uzunova V, Sheline Y, Davis J M, et al. P Natl Acad Sci USA. 1998; 95(6):3239-3244.
125. van Broekhoven F, Verkes R J. Psychopharmacology. 2003; 165(97).
126. Dichtel L E, et al. Neuropsychopharmacology. 2018 May; 43(6):1436-1444.
127. Nemeroff C B. Neuron. 2008 Jul. 31; 59(2):185-6.
128. Rasmusson A M, Pinna G, Paliwal P, et al. Biol Psychiatry. 2006 Oct. 1; 60(7):704-13.
129. Pinna G, Costa E, Guidotti A. Psychopharmacology (Berl). 2006 June; 186(3):362-72.
130. Rasmusson A M, Pinna G, Paliwal P, et al. Biological Psychiatry. 60(7):704-713.
131. Rasmusson A. P450 enzyme blocks in the progesterone GABAergic neuroactive steroid synthesis pathway in PTSD: sex differences. 2nd Neurosteroid Congress; Apr. 6-8 (2016); Durham, N.C. 2016.
132. Gillespie C F, et al. Am J Med Genet B Neuropsychiatr Genet. 2013 April; 162B(3):283-292.
133. Eicheler W, Tuohimaa P, Vilja P, et al. J Histochem Cytochem. 1994 May; 42(5):667-75.
134. Purdy R H, et al. Proc Natl Acad Sci USA. 1991 May 15; 88(10):4553-7.
135. Chalbot S, Morfin R. Drug Metabol Drug Interact. 2006; 22(1):1-23.
136. Pitman R K, et al. Nat Rev Neurosci. 2012 November; 13(11):769-87.
137. Dong E, et al. Proc Natl Acad Sci USA. 2001 Feb. 27; 98(5):2849-54.
138. Nin M S, Martinez L A, Pibiri F, et al. Front Endocrinol (Lausanne). 2011; 2:73.
139. Pibiri F, et al. Proc Natl Acad Sci USA. 2008 Apr. 8; 105(14):5567-72.
140. Geuze E, et al. Mol Psychiatry. 2008 January; 13(1):74-83, 3.
141. Pinna G, Rasmusson A M. Front Cell Neurosci. 2014; 8:256.
142. Pinna G, Dong E, Matsumoto K, et al. P Natl Acad Sci USA. 2003; 100(4):2035-2040.
143. Schule C, Eser D, Baghai T C, et al. Neuroscience. 2011 Sep. 15; 191:55-77.
144. Zhang L-M, et al. International J Neuropsychopharmacology. 2014; 17(10):1659-1669.
145. Kanes S J, et al. Human Psychopharmacology: Clinical and Experimental. 2017; 32(2).
146. Morena M, et al. P Natl Acad Sci USA. 2014 Dec. 23; 111(51):18333-18338.
147. Hill M N, Gorzalka B B. Behav Pharmacol. 2005 September; 16(5-6):333-52.
148. Valverde O, Torrens M. Neuroscience. 2012 Mar. 1; 204:193-206.
149. Neumeister A, et al. Mol Psychiatry. 2013 September; 18(9):1034-40.
150. Hungund B L, Vinod K Y, Kassir S A, et al. Mol Psychiatry. 2004 February; 9(2):184-90.
151. Juhasz G, Chase D, Pegg E, et al. Neuropsychopharmacology. 2009 July; 34(8):2019-27.
152. Monteleone P, Bifulco M, Maina G, et al. Pharmacol Res. 2010 May; 61(5):400-4.
153. Hill M N, Miller G E, Carrier E J, et al. Psychoneuroendocrinology. 2009 September; 34(8):1257-62.
154. Hill M N, Carrier E J, McLaughlin R J, et al. J. Neurochemistry. 2008; 106(6):2322-2336.
155. Hauer D, Schelling G, Gola H, et al. PLoS One. 2013; 8(5):e62741.
156. Hillard C J. Neuropsychopharmacology. 2018; 43(1):155.
157. Dlugos A, Childs E, Stuhr K L, et al. Neuropsychopharmacology. 2012; 37(11):2416.
158. Darmani N A, Izzo A A, Degenhardt B, et al. Neuropharmacology. 2005; 48(8):1154-1163.
159. Sabelli H C, Javaid J I. Neurosciences. 1995; 7:6-14.

160. Ghazizadeh-Hashemi M, et al. J Affect Disord. 2018 May; 232:127-133.
161. Heyman E, et al. Psychoneuroendocrinology. 2012 June; 37(6):844-51.
162. Rolland B, Deguil J, Jardri R, et al. Current drug targets. 2013; 14(7):724-732.
163. Esmaeili M A, Yadav S, Gupta R K, et al. Human molecular genetics. 2015; 25(2):317-327.
164. Racke M K, Drew P D. PPARs in neuroinflammation. PPAR research. 2008; 2008.
165. Jeon S W, Kim Y K. World journal of psychiatry. 2016 Sep. 22; 6(3):283-93.
166. O'Leary A. Psychological bulletin. 1990; 108(3):363.
167. Locci A, Geoffroy P, Miesch M, et al. Front Cell Neurosci. 2017; 11:208.
168. Adamczyk P, Golda A, McCreary A C, et al. J Physiol Pharmacol. 2008 June; 59(2):217-28.
169. Melis M, Scheggi S, Carta G, et al. J Neuroscience. 2013; 33(14):6203-6211.
170. Umathe S N, Manna S S, Jain N S. Behav Brain Res. 2011 Sep. 30; 223(1):125-34.
171. Stahl S M. The human platelet: Archives of General Psychiatry. 1977; 34(5):509-516.
172. Su T, Zhang L, Chung M, et al. J. Psychiatric Research. 2009; 43(13):1078-1085.
173. Holzman I R. Traumatic Lumbar Punctures. Pediatrics. 2004; 113(1):172-172.
174. Kaushal H S, Kathleen M R, Sarah N, et al. Emergency Medicine. 2003; 10(2):151-154.
175. Glass L. Nature. 2001 Mar. 8; 410(6825):277-84.
176. Hrabak J, et al. Clinical Microbiology Reviews. 2013 Jan. 1, 2013; 26(1):103-114.
177. Lagace-Wiens P R S, et al. J. Clin Microbiol. 2012 Oct. 1, 2012; 50(10):3324-3328.
178. Le-Niculescu H, Kurian S M, Yehyawi N, et al. Mol Psychiatry. 2009 February; 14(2):156-74.
179. Redei E E, Andrus B M, Kwasny M J, et al. Transl Psychiatry. 2014 Sep. 16; 4:e442.
180. Papakostas G I, Shelton R C, Kinrys G, et al. Mol Psychiatry. 2013 March; 18(3):332-9.
181. Pajer K, Andrus B M, Gardner W, et al. Transl Psychiatry. 2012 Apr. 17; 2:e101.
182. Mehta-Raghavan N S, Wert S L, Morley C, et al. Transl Psychiatry. 2016 Mar. 29; 6:e770.
183. Redei E E, Mehta N S. Annals of the New York Academy of Sciences. 2015; 1344(1):37-49.

Example 3

In the search for reliable and, possibly, specific biomarkers for neuropsychiatric disorders, growing evidence has demonstrated that biosynthesis of neuroactive steroids and the endocannabinoid system are involved in the neuropathology of post-traumatic stress disorder (PTSD) and major depressive disorder (Rasmusson et al., 2006, Uzunova et al., 1998, Locci and Pinna, 2017α) (FIG. 11).

Although, undisputable progress has been made to assess validity of biomarkers for psychiatric disorders, the topic still remains underdeveloped as compared to other fields of neuroscience (Fernandes et al., 2017). The diagnosis of psychiatric disorders still relies on subjective measures centered on the DSM-5 criteria which have several shortcomings (Brewin et al., 2017). Psychiatric conditions are poorly understood and there is a wide heterogeneity in how illness manifests in several individuals. Furthermore, self-assessment of one's own feelings can be biased, ill-defined, and difficult, making psychological diagnoses unreliable and may lead to treatment inefficacy. Thus, searching for potential biomarkers to guide precision medicine in the treatment of PTSD, and to increase the success of clinical trials and prompt the development of novel and specific treatments, is required. To aid this search, more sophisticated methodological tools and validated animal models has also become essential to reliably correlate a behavioral changes with neurochemical alterations (reviewed in Ngounou Wetie et al., 2013).

The overlap of symptoms and the comorbidity with other psychiatric disorders such as major depressive disorder, anxiety spectrum disorders, and even suicidal ideation (Franklin et al., 2018), suggest a biosignature for PTSD should include numerous biomarkers (Locci and Pinna, 2017α). A refined approach to more specifically "bio-define" PTSD can be to establish a biomarker axis or in other words, to assess the relation of numerous biomarkers as opposed to only a few (Loci and Pinna, 2017α), which fluctuate in concert and correlate uniquely with PTSD-like behavioral modifications. Insofar, a biomarker axis may provide a higher accuracy in the diagnosis of the disorder with benefits for prediction in PTSD treatment response and relapse (Pinna and Izumi, 2018; Locci et al., 2018). As a matter of fact, the gold standard treatment for PTSD and depression, the selective serotonin reuptake inhibitors (SSRIs), improve only half of the treatment-seeking patients and they are associated with severe side-effects (reviewed in Bernardy and Friedman, 2017; Bernardy and Friedman, 2015; Golden, et al., 2002; Rush et al., 2006; Kemp et., 2008). This also suggests these psychiatric disorders are complex, multifaceted diseases arising from multiple and diverse neurobiological backgrounds and therefore, symptoms may not always recapitulate to a serotonergic deficit and administering SSRIs may not improve symptoms. Unveiling reliable biomarkers is also a necessity for patient stratification in treatment selection as well as for drug development through clinical trials.

Working with the gas chromatography-mass spectrometry (GC-MS) can provide reliable information based on a powerful technology with high sensitivity and unsurpassed structure selectivity (Uzunov et al., 1996; Pinna et al., 2000). Hence, by applying the GC-MS measurements of neuroactive steroids in serum, plasma, CSF and post-mortem brain, in the past decade, we have shed light in the fundamental role of neuroactive steroids in patients with neuropsychiatric disorders (Rasmusson et al., 2006; 2016; 2017; Pineles et al., 2018m Locci and Pinna, 2017α).

The biosynthesis of allopregnanolone, a positive allosteric modulator of GABA's action at $GABA^A$ receptors has been found deficient in a number of neuropsychopathologies, including epilepsy (eg., PHDH19), major depression, PTSD, perceived social isolation, post-partum depression, premenstrual syndrome, and anorexia nervosa or obesity complicated by anxiety and depression symptoms in women (Trivisano et al., 2017; Uzunova et al., 1998; Romeo et al., 1998; Rasmusson et al., 2006; Nemerof et al., 2008; Lovick, 2013; Dichtel et al., 2018, Pineles et al., 2018). Therapeutic measures aimed at reinstating normal allopregnanolone levels in deficient-patients correlates with improved symptoms (Kane et al., 2017). The question arises as to whether allopregnanolone biosynthesis per se is a reliable biomarker to predict, diagnose and instruct treatment selection of patients or whether its relation with neurotransmitter systems ($GABA_A$ and NMDA receptors), stimulation of neurotropic factors (e.g., BDNF), and/or crosstalk with the endocannabinoid system (e.g., PPAR-α) may provide a valuable biomarker axis with a higher disorder selectivity.

This analysis includes both neurosteroids that are positive allosteric modulators of $GABA_A$ receptors (Pinna et al., 2000; Belelli and Lambert, 2005), such as allopregnanolone and pregnanolone and their sulfated forms that are inhibitors of NMDA-mediated tonic neurotransmission (Vyklicky et al., 2016), which can result in neuroprotection. The unforeseen behavioral and neurosteroidogenic function of PPAR-α, formally known to regulate pathophysiological functions, including inflammation and oxidative stress, opens the field for potential biomarkers for PTSD.

This Example will discuss a biomarker role for allopregnanolone biosynthesis and the endocannabinoid system for stress-induced disorders. The strategy of assessing a biomarker axis, which can indicate the relation of various inter-related neurobiological deficits for one disorder (FIG. 12), may help for diagnosis accuracy and for designing successful individualized treatments.

The unforeseen behavioral and neurosteroidogenic function of PPAR-α, formally known to regulate pathophysiological functions, including inflammation and oxidative stress, opens the field for potential biomarkers for PTSD.

Neurosteroid Action at $GABA_A$ and NMDA Receptors. Sulfated or unconjugated neuroactive steroids modulate ionotropic amino acid neurotransmitter receptors, including $GABA_A$ and NMDA receptors. The $GABA_A$ receptor offers two binding residues that express affinity for allopregnanolone and unconjugated congeners (e.g., pregnanolone) that act as potent positive allosteric modulators of the action of GABA at $GABA_A$ receptors. One is located at the interface of the α/β subunits, and the other is within the cavity of a subunits (Hosie et al., 2006). The α,β,γ $GABA_A$ receptor subtype is the most frequent synaptic configuration and is highly sensitive to benzodiazepines but shows lower sensitivity to GABA and neurosteroids (Nusser and Mody, 2002). The α,β,δ GABAA receptor subtype expressed in the extrasynaptic region is benzodiazepine-insensitive, show low efficacy for GABA, but neurosteroids increase its agonist efficacy (Stell et al., 2003; Shu et al., 2012). This receptor combination shows high efficacy for neurosteroids (Brown et al., 2002; Nusser and Mody, 2002; Wohlfarth et al., 2002). See e.g. FIG. 11.

Sulfated neurosteroids such as pregnenolone sulfate, dehydroepiandrosterone sulfate, pregnanolone sulfate and allopregnanolone sulfate may function as endogenous neuromodulators by inhibiting $GABA_A$ receptors, or pending on the receptor conformation and the sulfated neuroactive steroid examined, by activating or inhibiting NMDA-mediated neurotransmission (Park-Chung et al., 1999). Sulfation at $C_3$ is essential to reverse the direction of modulation from positive to negative in $GABA_A$ receptors. Steroid negative and positive modulators act through distinct sites, which implies that steroid negative and positive modulators can act independently or coordinately to modulate the flavor of GABAergicmediated inhibitory neurotransmission (reviewed in Smith et al., 2014). While, micromolar concentrations of pregnenolone sulfate negatively modulate $GABA_A$ receptors, pregnenolone sulfate can negatively or positively modulate NMDA receptors, depending on the subunits expressed (Malayev et al., 2002; Smith et al., 2014). For instance, pregnenolone sulfate potentiates NMDA receptors that contain NR2A and NR2B subunits, but negatively modulates NR2C and NR2D-containing receptors (Malayev et al., 2002).

Recent studies showed that pregnanolone sulfate has a potent inhibitory action at tonic rather than synaptically-activated NMDA receptors, which provides neuroprotection and possibly improves emotional behavior and cognition (Vyklicky et al., 2016). This feature is relevant for developing a novel class of steroid-based NMDA inhibitors devoid of the psychotomimetic effects that characterize classical NMDA receptor inhibitors, including ketamine.

While $GABA_A$ receptor subunit expression during protracted stress has been previously investigated (discussed below), the role and action of sulfated pregnanolone, pregnenolone, allopregnanolone, and the expression of NMDA receptor subunit in PTSD patients and in rodent stress models, still warrants elucidation.

The Neurosteroid and Endocannabinoid Corsstalk.

Intriguingly, studies conducted in cell cultures, brainstem and spinal cord showed the endocannabinoid, N-palmitoylethanolamine (PEA) binding at the ligand-activated nuclear receptor, peroxisome proliferator-activated receptor (PPAR-α) stimulates allopregnanolone biosynthesis and potentiates pentobarbital-induced sedation (Sasso et al., 2010, 2012; Raso et al., 2012). These observations suggest that PPAR-α may play a role in the regulation of emotions by inducing neurosteroidogenesis in corticolimbic neurons following binding with its endogenous ligand, PEA, or synthetic agonists.

Whereas, the cannabinoid receptor type 1 (CB1) has been shown to regulate emotions and stress responses, PPAR-α's role on emotions remains poorly understood (Häring et a., 2012; Riebe and Wotjak, 2011). The relevance of the endocannabinoid system in behavior is highlighted by expression of CB1 and PPAR-α in glutamatergic neurons of emotion-relevant areas that are important for PTSD (amygdala, hippocampus, frontal cortex) (Katona, 2009; Moreno et al., 2004; Lo Verme et al., 2005; Petrosino et al., 2017; D'Agostino et al. 2009). Moreover, evidence suggests CB1 disruption, leads to impaired fear extinction (Reich et al., 2008), depressive- and anxiety-like behavior, while agonists, like AEA, induce anxiolysis and improves fear responses (Hill and Patel, 2013). Current thought suggests that the effects of AEA at CB1 account for the majority of anti-fear effects (Jacob et al., 2012; Viveros et al., 2005; Kamprath et al., 2006; Thiemann et I., 2008; Marsicano et al., 2002), however this view seems no longer tenable (Pistis and Melis, 2010). In addition to these cell-surface cannabinoid receptors, there is growing evidence that PPAR-α's activation represents a novel mechanism by which cannabinoids modulate behavior. Stimulation of PPAR-α by PEA or synthetic agonists was recently shown to elevate corticolimbic allopregnanolone levels in hippocampus, amygdala, prefrontal cortex and in olfactory bulb, which correlated with improvement of PTSD-like behavior in socially isolated mice (Locci and Pinna, 2017α). PEA facilitates contextual fear extinction and fear extinction retention and induces anti-aggressive, anxiolytic, and antidepressant-like effects in socially isolated mice (Locci et al., 2017, Locci and Pinna, 2017b). PPAR-α synthetic agonists normalized allopregnanolone levels and improved behavior, whereas antagonism at PPAR-α, inhibition of allopregnanolone biosynthetic enzymes, or PPAR-αKO mice prevented both PEA-induced behavior and its neurosteroidogenic effects (Locci and Pinna, 2017b).

While the role of PPAR-α in neuropsychiatric disorders is just emerging, studies in the field suggest serum PEA and OEA levels increase after acute social stressor (Dlugos et al., 2012) and decrease after recovery (Hill et al., 2009α). Stress evokes fast induction of FAAH, which reduces PEA levels (Patel et al., 2005; Hill et al., 2009b). In PTSD patients, symptoms are inversely correlated with reduced hair levels of PEA, OEA and SEA in both males and females (Wilker et al., 2016). PEA adjunctive therapy to citalopram improves symptoms in depressed patients (Ghazizadeh-Hashemi et al., 2018). Furthermore, intense workouts increase PEA and OEA levels and improve depression and PTSD (Heyman et al., 2012). In rodents, exposure to predator stressors reduces PEA and OEA levels (Holman et al., 2014), but, antidepressant-like effects are induced by increasing PEA and OEA (Adamczyk et al., 2008; Umathe et al., 2011; Melis et al., 2013).

Collectively, the crosstalk between the endocannabinoid system and neurosteroid biosynthesis during stress may unveil biomarker axis uniquely altered in specific stress-induced mood disorders.

Biomarkers and Treatment Options for PTSD at the Interface of the Endocannabinoid and Neurosteroid Axis.

Neuropsychiatric disorders, such as PTSD, are not currently amenable to objective neurobiological determinations as is routine practice in the diagnosis and treatment of other medical conditions. This is likely due to the general complexity and multifactorial origins of these disorders and the difficulty to establish a consistent bio-signature. No biomarkers for PTSD have to date been firmly assessed with diagnostic validity. Biomarker candidates for PTSD have been proposed but often they share overlaps with other psychiatric disorders with similar symptoms and that are currently treated with the same drugs, Indeed, the first-choice pharmacological treatments for PTSD, the SSRIs, act through multiple molecular mechanisms other than by inhibiting serotonin reuptake. These mechanisms include the stimulation of neurosteroid and endocannabinoid biosynthesis and neurotrophic factors, such as BDNF, which are found deficient in PTSD. Increasing allopregnanolone levels is also associated with increased BDNF expression (Nin et al., 2011). Collectively, these findings have contributed to improve our understanding of the psychobiological abnormalities associated with PTSD and promote the development of novel targeted treatment options. For instance, the correlation between the impairment of neurosteroid biosynthesis and behavioral modifications in neuropsychiatric disorders has been the focus of several studies (van Broekhoven and Verkes, 2003; Agis-Balboa et al., 2014; reviewed in Pinna, 2014 and Locci & Pinna, 2017a). A reduction in the content of the GABAergic modulator allopregnanolone and its equipotent isomer pregnanolone was reported in cerebrospinal fluid (CSF) and serum of major depression and PTSD patients (Uzunova et al., 1998; Romeo et al., 1998; Rasmusson et al., 2006; 2016; Pineles et al., 2018). A negative correlation between CSF allopregnanolone levels and PTSD symptoms was more recently confirmed in male patients (Rasmusson et al., 2018). Other clinical studies support the significance of allopregnanolone biosynthesis as a biomarker of mood disorders (Uzunova et al., 1998; Agis-Balboa et al., 2014; reviewed in Zorumski et al., 2013, Schule, 2014; and Locci and Pinna, 2017) with finding showing decreased allopregnanolone levels in postpartum depression (Nemeroff, 2008), under treatment with finasteride, an allopregnanolone biosynthetic enzyme blocker (Altomare, & Capella, 2002; Caruso et al., 2015; Welk et al., 2017), and with anorexia nervosa or obese complicated by anxiety and depression (Dichtel et al., 2018). Intriguingly, SSRI treatments normalize plasma, CSF, and brain allopregnanolone content in association with improvement of symptoms (Romeo et al., 1998; Uzunova et al., 1998; Agis-Balboa et al., 2014). These findings are in support of the role of allopregnanolone in the mechanisms of SSRIs' anxiolytic effects (Pinna, 2015).

The downregulation of neurosteroid levels found in PTSD and depressed patients can be modeled in rodents exposed to protracted of stress, including the socially-isolated mouse. Allopregnanolone is produced in brain corticolimbic neurons and (FIG. 11) a reduction of its levels by prolonged social isolation (Agis-Balboa et al., 2006; 2007) or exposure to single prolonged stressors, result in development of anxiety-like behavior, aggression and enhanced contextual fear conditioning responses associated with impairment of fear extinction and elevated spontaneous fear responses at recall (Dong et al., 2001; Pibiri et al., 2008; Zhang et al., 2014; Pinna and Rasmusson, 2014). These preclinical studies further support allopregnanolone as a putative biomarker for stress-induced emotional modification, such as exaggerated fear responses and impaired fear extinction, a core feature of PTSD (Pinna et al., 2008; Pibiri et al, 2008; Pinna and Rasmusson, 2011). This evidence also suggests that new therapeutic approaches should counteract the downregulation of neurosteroid biosynthesis to improve symptoms in PTSD patients. In a recent phase 3 clinical trial, intravenous allopregnanolone (brexanolone or SAGE-547) or an oral analog (SAGE-217) showed a rapid and long-lasting remission of post-partum depression symptoms and major depressive disorder symptoms (Kanes et al., 2017). Stress tremendously affects the expression of GABAA receptor subunits (reviewed in Locci and Pinna, 2017).

After social isolation, the $\alpha 4$, $\alpha 5$ and $\delta$ subunit expression was increased, and the $\alpha 1$, $\alpha 2$ and $\gamma 2$ was significantly decreased in corticolimbic areas (Pinna et al., 2006b; Pibiri et al., 2008). These changes result in decreased benzodiazepine recognition sites and lower pharmacological response to benzodiazepines (Pinna et al., 2006b; Nin et al., 2011a). Remarkably, protracted stress favors a $GABA_A$ receptor composition with high sensitivity for allopregnanolone and its analogs (Locci et al., 2017). Clinical findings support lower benzodiazepine recognition sites in brain of PTSD patients in association with benzodiazepine-insensitivity (Geuze et al., 2008). Altogether, these findings suggest that isolation stress results in: i) changes in $GABA_A$ receptor subunit composition; ii) downregulated neurosteroidogenesis; and iii) lack of response to benzodiazepines, which may provide a unique biomarker axis for PTSD (FIG. 12).

The pharmacological profile of SSRIs on stimulation of neurotropic factors, including the brain derived neurotrophic factor (BDNF), via stimulation of allopregnanolone biosynthesis is an additional mechanism to consider when establishing biomarkers for PTSD. BDNF expression decrease in PTSD patients is associated with symptom severity. In the socially isolated mouse, fluoxetine improves behavior by elevating the corticolimbic levels of allopregnanolone and BDNF expression, independently from the action of these drugs on serotonin reuptake inhibition.

Biomarkers that instruct which treatment would be most effective for a patient is expected to considerably reduce non-responders and non-completers rate. Following activation of PPAR-α, undoubtedly their cross-talk offers a unique opportunity to assess a biomarker axis that encompasses these two systems (FIG. 12). Both endocannabinoids and neurosteroids can be measured by GC-MS, however, presently there is no method that can determine them simultaneously in the same samples.

FIG. 11 can demonstrate the regulation of emotional behavior via endocannabinoid and neurosteroid systems cross-talk. The neurosteroid, allopregnanolone (Allo) and its equipotent isomer pregnanolone (PA) are primarily synthesized in glutamatergic neurons and upon secretion, they may act at $GABA_A$ receptors located on cell bodies or dendrites of distal pyramidal neurons (Arrow 1, FIG. 11). They may also act at $GABA_A$ receptors located on glutamatergic neurons' dendrites or cell bodies by an autocrine mechanism (Arrow 2, FIG. 11), or may access and act at the intracellular sites of GABAA receptors located in glutamatergic neurons that produced allopregnanolone itself (Arrow 3, FIG. 11) (Agis-Balboa et al., 2006; 2007; Pinna et al., 2008). Allopregnanolone can play a central neuromodulatory role in facilitating the action of GABA at $GABA_A$ receptors (a primary target of anxiolytics) and in the fine-tuning of the receptor for agonists and GABA mimetic agents (Pinna et al., 2000). The finding that allopregnanolone facilitates the efficacy of $GABA_A$ receptor allosteric modulators substantiates its endogenous physiological relevance (Pinna et al., 2000; 2008; Guidotti et al., 2001). $GABA_A$ receptors composed by $\alpha,\beta,\gamma$ subunits are the most common configuration in the synaptic membranes and they are responsible for the inhibitory phasic currents. These receptors are benzodiazepine-sensitive but show lower sensitivity to GABA and allopregnanolone (Nusser and Mody, 2002). The $GABA_A$ receptors including $\alpha,\beta,\delta$ subtypes are mostly extrasynaptic and mediate inhibitory tonic currents. They are not sensitive to benzodiazepines and show low efficacy for GABA, however, allopregnanolone increase their efficacy (Stell et al., 2003; Shu et al., 2012). The efficacy of GABAergic neurosteroids is greatly enhanced for this receptor combination (Brown et al., 2002; Nusser and Mody, 2002; Wohlfarth et al., 2002). Remarkably, protracted stress favors a $GABA_A$ receptor composition with high sensitivity for allopregnanolone and its analogs (Locci and Pinna, 2017$\alpha$).

Following the action of sulphotransferase, allopregnanolone and pregnanolone can be transformed into allopregnanolone sulfate (Allo-S) and pregnanolone sulfate (PAS). These sulfated steroids can be measured by gas chromatography-mass spectrometry in serum, CSF, and brain of patients or rodents in concentrations consistent with a physiological role in modulating neurotransmitter systems (Smith et al., 2014; Locci and Pinna, 2017b). Recently, pregnanolone sulfate has been shown to inhibit NMDA receptors. Pregnanolone sulfate can accumulate in plasma membranes and may accesses binding sites that are located at NMDA receptors (Borovska et al., 2012). Pregnanolone sulfate, and probably allopregnanolone sulfate, is highly potent at inhibiting tonic rather than synaptically mediated NMDA receptor neurotransmissions. While synaptic NMDA receptors play a pivotal role in synaptic plasticity, learning and memory, as well as in synaptogenesis, tonic-mediated NMDA receptor neurotransmission is mostly involved with excitotoxicity. Thus, the effects of pregnanolone sulfate negative modulation of tonic-mediated NMDA receptor neurotransmission have relevance for neuroprotection (Vyklicky et al., 2016). By this mechanism, these allopregnanolone and pregnanolone sulfated derivatives may play a role in the regulation of cognitive processes and of emotional behavior (reviewed in Locci and Pinna, 2017$\alpha$).

There is growing evidence that the intracellular peroxisome proliferator-activated receptor (PPAR-$\alpha$), members of the ligand-activated nuclear steroid receptor superfamily (O'Sullivan, 2007; Forman et al., 1996), is also a cannabinoid target. PPAR-$\alpha$ heterodimerize with the retinoid X receptor (RXR) and binds to the consensus regions on the target gene promoters and initiates transcription (Neumeister, 2013). Given that endocannabinoids activate PPAR-$\alpha$ (Marsicano et al., 2002; Pistis and Melis, 2010), the activation of these nuclear receptors represents a novel mechanism by which cannabinoids may modulate behavior. The endocannabinoid, N-palmitoylethanolamine (PEA) is a PPAR-$\alpha$ agonists, which is found decreased in PTSD patients (Wilker, S. et al., 2016). Recent preclinical findings showed that supplementing PEA in rodent PTSD models improves emotional behavior by enhancing allopregnanolone biosynthesis in corticolimbic glutamatergic neurons. This effect is mimicked by PPAR-$\alpha$ agonists and prevented by allopregnanolone biosynthetic enzyme blockers and by deletion of the PPAR-$\alpha$ gene (Locci and Pinna, 2017). Thus, anxiolytic, anti-aggressive and anti-fear effects of PEA and other synthetic cannabinoids that act as PPAR-$\alpha$ agonists may relate to an induction of corticolimbic allopregnanolone's biosynthetic enzymes, including CYP11A1 and 5$\alpha$-reductase. This may result in potentiation of $GABA_A$ receptor signal transduction and improved behavioral dysfunction (represented in the bottom panel). Stress effects on PEA levels and probably expression of PPAR-$\alpha$ may result in the downregulation of allopregnanolone's biosynthetic enzyme expression and allopregnanolone levels. The interface of the endocannabinoid and neurosteroid systems may provide an important biomarker axis to selectively predict, diagnose, and establish the best individualized treatment selection for PTSD patients.

FIG. 12 shows a schematic demonstrating the biomarker axis at the interface of the endocannabinoid and neurosteroid systems. In animal models of PTSD, protracted stress results in the downregulation of allopregnanolone biosynthetic enzymes (e.g., 5$\alpha$-reductase type I, 5$\alpha$-RI) and allopregnanolone concentrations in corticolimbic glutamatergic neurons of the frontal cortex, hippocampus, and basolateral amygdala. This allopregnanolone decrease correlates with behavioral dysfunction, such as increased aggression, enhanced contextual fear responses and anxiety-like behavior (Pinna et al., 2003; Pibiri et al., 2008). Supplying allopregnanolone or stimulating its biosynthesis decreases anxiety-like behavior, aggression and fear responses (Pinna, 2014; Pinna and Rasmusson, 2014). Stress may also result in changes in $GABA_A$ receptor subunit expression (Pinna et al., 2006; reviewed in Locci and Pinna, 2017$\alpha$) with increased $\alpha 4$, $\alpha 5$ and $\delta$ subunits and decreased $\alpha 1$, $\alpha 2$ and $\gamma 2$, which result in down-regulated benzodiazepine binding sites and inefficacy of benzodiazepine pharmacological action (Pinna et al., 2006; Nin et al., 2011b). Protracted stress results in increased $GABA_A$ receptor subunits, including $\alpha_{4-6},\beta,\delta$, highly sensitivity for allopregnanolone (Locci and Pinna, 2017$\alpha$). Both allopregnanolone biosynthesis downregulation and decreased benzodiazepine binding sites have been reported in PTSD patients (Rasmusson et al., 2006; 2018; Geuze et al., 2008). Thus, the combination of downregulation of allopregnanolone biosynthesis, changes in GABAA receptor subunit expression, and lack of benzodiazepine pharmacological action are peculiar changes observed in PTSD that may provide a selective biomarker axis for this disorder. Stress may affect PEA levels and expression of PPAR-$\alpha$ which in turn may downregulate allopregnanolone concentrations. Thus, the PPAR-$\alpha$-allopregnanolone axis may provide further biomarker candidates to support selection of the best individualized precision medicine for PTSD. Abbreviations: Allo, allopregnanolone; GABA, $\gamma$-aminobutyric acid; PEA, N-palmitoylethanolamine; PPAR-$\alpha$, peroxisome-proliferator activated receptor-$\alpha$StAR, steroidogenic acute regulatory protein: TSPO, 18 kDa translocator protein.

REFERENCES FOR EXAMPLE 3

Altomare, G. & Capella, G. L. (2002) *J. Dermatol.* 29, 665-9.
Adamczyk P, Golda A, Przegalinski E. (2008). *J Physiol Pharmacol.* 59:217-28.

Agis-Balboa, R C, et al. (2006) *Proc. Natl. Acad. Sci. USA* 103, 14602-7.
Agis-Balboa, R C, et al. (2007). *Proc. Natl. Acad. Sci. USA* 104, 18736-41.
Agis-Balboa R C, Guidotti A, Pinna G. (2014) *Psychopharmacology*. 231:3569-80. 2014.
Belelli, D. & Lambert, J. J. (2005) *Nat. Rev. Neurosci.* 6, 565-75.
Bernardy N C, Friedman M J. (2017) *Curr Opin Psychol.* 14:116-121.
Bernardy N C, Friedman M J (2015). *Curr Psychiatry Rep.* 17:564.
Brewin C R, et al. (2017). *Clin Psychol Rev.* 58:1-15.
Brown N, et al. (2002). *Br J Pharmacol* 136: 965-974.
Caruso, D. (2015). *J. Steroid Biochem. Mol. Biol.* 146, 74-9.
D'Agostino, G. (2007). *J. Pharmacol. Exp. Ther.* 322, 1137-43.
Dichtel L E, et al. (2018). *Neuropsychopharmacology*
Dlugos, A. (2012) *Neuropsychopharmacology* 37, 2416-27.
Fernandes B S, Williams L M, Steiner J, Leboyer M, Carvalho A F, Berk M. (2017). *BMC Med.* 15:80.
Forman B M, Chen J, Evans R M (1996) *Ann N Y Acad Sci* 804, 266-75
Franklin C L, Raines A M, et al. (2017). *Psychiatry Res.* 261:504-507.
Geuze E, et al. (2008) *Mol Psychiatry* 13, 74-83.
Ghazizadeh-Hashemi, M. (2018). *J. Affect. Disord.* 232, 127-133.
Girdler, S. S. & Klatzkin, R. (2007) *Pharmacol. Ther.* 116, 125-39.
Golden R N, et al. (2002). *J Clin Psychiatry* 63: 577-584.
Heyman, E. (2012). *Psychoneuroendocrinology* 37, 844-51.
Hill, M. N. et al. (2009a) *Psychoneuroendocrinology* 34, 1257-62.
Hill M. N. et al. (2009b) *Trends Pharmacol. Sci.* 30, 484-93.
Hill, M. N. & Patel, S. (2013) *Biol. Mood Anxiety Disord.* 3, 19.
Häring M, Guggenhuber S, Lutz B. (2012) *Neuroscience.* 1; 204:145-58.
Hosie A M, Wilkins M E, da Silva H M, Smart T G (2006). *Nature* 444: 486-489.
Kanes S, et al. (2017). Lancet. 390:480-489.
Kamprath K, et al. (2006) J Neurosci 26(25), 6677-86
Katona, I. Behav. Neurosci 1, 65-86 (2009).
Kemp A H, Gordon E, Rush A J, Williams L M (2008). C N S Spectr 13: 1066-1086.
Jacob W, et al. (2012) Neurobiol Learn Mem 98(1), 47-55.
Locci, A. & Pinna, G. Br. J. Pharmacol. 174, 3226-3241 (2017).
Locci A, Khan F, Khan M A, and Pinna G: Pinna G. & Izumi T (Editors) Nova Biomedical Publ. 2018.
Locci A, Pinna G. 165.19. 47th Annual Meeting Society for Neuroscience, Washington, D.C., USA, Nov. 11-15, 2017.
Lo Verme, J. et al. Mol. Pharmacol. 67, 15-9 (2005).
Lovick, T. J. Psychopharmacol. 27, 1180-5 (2013).
Malayev A, Gibbs T T, Farb D H (2002). Br J Pharmacol 135: 901-909.
Marsicano G, et al. (2002) Nature 418(6897), 530-4
Neumeister, A. et al. Psychoneuroendocrinology 51, 577-84 (2014).
Nemeroff C B (2008). Neuron 59: 185-186.
Nin S M, Martinez L A, Pibiri F, Nelson M and Pinna G: Front. 2011 Endocrin. 2:73.
Ngounou Wetie A G, et al. 2013 Jun. 5; 1(1):8
Nusser Z, Mody 1 (2002). J Neurophysiol 87: 2624-2628.
O'Sullivan S E (2007) Br J Pharmacol 152(5), 576-82.
Patel, S. et al. J. Lipid Res. 46, 342-9 (2005).

Park-Chung M, et al. Brain Res. 1999. 830(1):72-87.
Petrosino, S. & Di Marzo, V. Br. J. Pharmacol. 174, 1349-1365 (2017).
Pibiri, F. et al. Proc. Natl. Acad. Sci. USA 105, 5567-72 (2008).
Pineles, S. L., et al., Psychoneuroendocrinology (in press).
Pinna G and Izumi T: Pinna G. & Izumi T (Editors) Nova Biomedical Publ. 2018.
Pinna G, Rasmusson A. Front. Cell. Neurosci. 8:256.2014.
Pinna G. Targeting neurosteroidogenesis as therapy for PTSD. Front. Pharmacol. 2014
Pinna G and Rasmusson A M: J. Neuroendocrinology. 24:102-16. 2012
Pinna, G. et al. Proc. Natl. Acad. Sci. USA 100, 2035-40 (2003).
Pistis M, Melis M. (2010) Cur. Med Chem. 17:1450-67.
Rasmusson, A. M. et al. Biol. Psychiatry 60, 704-13 (2006).
Rasmusson A M, King M, Gregor K, Scioli-Salter E, Pineles S, Valovski I et al. (2016). Sex differences in the enzyme site at which GABAergic neuroactive steroid synthesis is blocked in PTSD: implications for targeting of PTSD therapeutics. 32nd Annual Meeting, International Society for Traumatic Stress Studies Dallas, Tex.
Rasmusson, A. M. et al. Neurosci. Lett. 649, 156-163 (2017).
Raso, G. M. et al. J. Neuroendocrinol 23, 591-600 (2011).
Reich C G, Mohammadi M H, Alger B E. J Psychopharmacol. 2008; 22(7):769-77.
Riebe C J, Wotjak C T. Endocannabinoids and stress. Stress. 2011. 14(4):384-97.
Romeo, E. et al. Am. J. Psychiatry 155, 910-3 (1998).
Rush A J, et al. (2006). Biol Psychiatry 59: 493-501
Sasso, O., et al. Eur. Neuropsychopharmacol. 20, 195-206 (2010).
Sasso, O. et al. Pain 153, 33-41 (2012).
Schüle, C. et al. Neuroscience 191, 55-77 (2011).
Schüle, C. et al. TProg. Neurobiol. 113, 79-87 (2014).

We claim:

1. A method of treating a neuropsychiatric disorder or a symptom thereof in a subject in need thereof, the method comprising:

administering an effective amount of a neurosteroid having a formula according to Formula BR297

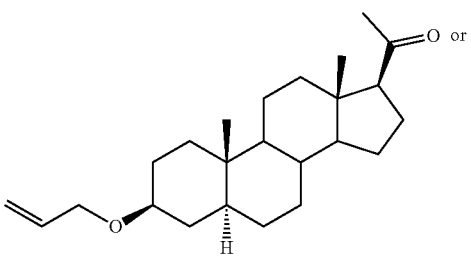

Formula BR351

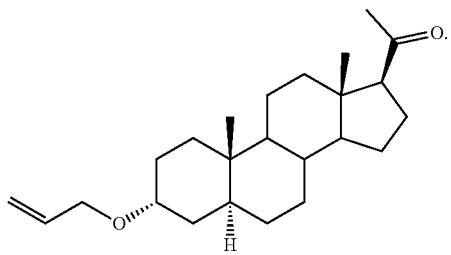

2. The method of claim 1, wherein the effective amount ranges from about 0.325 mg/kg to about 15 mg/kg.

3. The method of claim 1, wherein the neuropsychiatric disorder is an anxiety disorder.

4. The method of claim 3, wherein the neuropsychiatric disorder is post-traumatic stress disorder.

5. The method of claim 1, wherein the neuropsychiatric disorder is a depression disorder.

6. The method of claim 5, wherein the depression disorder is major depressive disorder.

7. The method of claim 1, wherein the subject in need thereof has not responded to treatment with one or more selective-serotonin reuptake inhibitors.

8. The method of claim 1, further comprising the step of detecting a biomarker for post-traumatic stress disorder (PTSD) in a sample from the subject in need thereof.

9. The method of claim 8, wherein the biomarker for PTSD is the amount of allopregnanolone in a bodily fluid sample of the subject in need thereof.

10. The method of claim 1, further comprising the step of detecting a biomarker for major depressive disorder in a bodily fluid sample of the subject in need thereof.

11. The method of claim 10, wherein the biomarker for major depressive disorder is the amount of allopregnanolone in a bodily fluid sample of the subject in need thereof.

12. The method of claim 1, wherein the neurosteroid has a formula according to Formula BR297

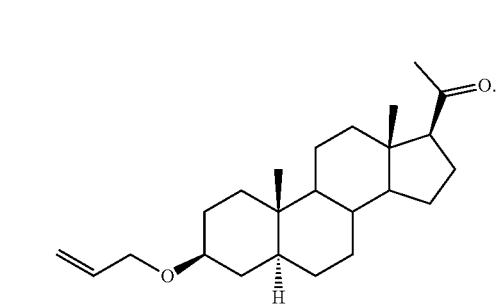

13. The method of claim 12, wherein the effective amount ranges from about 0.325 mg/kg to 2.5 mg/kg.

14. The method of claim 1, wherein the neurosteroid has a formula according to Formula BR351

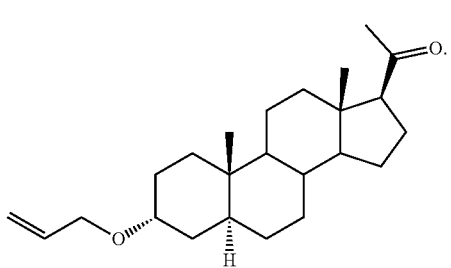

15. The method of claim 14, wherein the effective amount ranges from about 1 mg/kg to about 5 mg/kg.

* * * * *